US011865102B2

(12) United States Patent
Guy et al.

(10) Patent No.: US 11,865,102 B2
(45) Date of Patent: *Jan. 9, 2024

(54) CANNABIDIOL PREPARATIONS AND ITS USES

(71) Applicant: GW Research Limited, Cambridge (GB)

(72) Inventors: Geoffrey Guy, Cambridge (GB); Volker Knappertz, Cambridge (GB); Benjamin Whalley, Cambridge (GB); Marie Woolley-Roberts, Cambridge (GB); James Brodie, Cambridge (GB); Katarzyna Lach-Falcone, Cambridge (GB); Alan Sutton, Cambridge (GB); Royston Gray, Cambridge (GB); Rohini Rajyalaxmi Rana, Cambridge (GB)

(73) Assignee: GW Research Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/529,005

(22) Filed: Nov. 17, 2021

(65) Prior Publication Data

US 2022/0168266 A1 Jun. 2, 2022

Related U.S. Application Data

(63) Continuation of application No. 17/011,715, filed on Sep. 3, 2020, now Pat. No. 11,207,292, which is a continuation of application No. PCT/GB2019/051173, filed on Apr. 26, 2019.

(30) Foreign Application Priority Data

Apr. 27, 2018 (GB) ...................................... 1806953

(51) Int. Cl.
| | |
|---|---|
| *A61K 31/352* | (2006.01) |
| *A61P 25/08* | (2006.01) |
| *A61K 9/00* | (2006.01) |
| *A61K 9/70* | (2006.01) |
| *A61K 31/05* | (2006.01) |
| *A61K 36/185* | (2006.01) |
| *A61P 25/18* | (2006.01) |

(52) U.S. Cl.
CPC .......... *A61K 31/352* (2013.01); *A61K 9/0019* (2013.01); *A61K 9/0053* (2013.01); *A61K 9/0073* (2013.01); *A61K 9/7023* (2013.01); *A61K 31/05* (2013.01); *A61K 36/185* (2013.01); *A61P 25/08* (2018.01); *A61P 25/18* (2018.01); *A61K 2236/33* (2013.01); *A61K 2236/51* (2013.01)

(58) Field of Classification Search
CPC .... A61K 31/352; A61K 31/05; A61K 36/185; A61K 2236/33; A61K 2236/51
See application file for complete search history.

(56) References Cited

U.S. PATENT DOCUMENTS

| | | | |
|---|---|---|---|
| 2,304,669 | A | 12/1942 | Adams |
| 6,383,513 | B1 | 5/2002 | Watts et al. |
| 7,025,992 | B2 | 4/2006 | Whittle et al. |
| 8,673,368 | B2 | 3/2014 | Guy et al. |
| 9,023,322 | B2 | 5/2015 | van Damme et al. |
| 9,259,449 | B2 | 2/2016 | Raderman |
| 9,474,726 | B2 | 10/2016 | Guy et al. |
| 9,492,438 | B2 | 11/2016 | Pollard |

(Continued)

FOREIGN PATENT DOCUMENTS

| | | |
|---|---|---|
| EP | 2 311 475 A2 | 4/2011 |
| GB | 2 002 754 A | 2/1979 |

(Continued)

OTHER PUBLICATIONS

Elsohly, M. & Gul, W., "Constituents of Cannabis Sativa," Chapter 1, Handbook of Cannabis, Roger Pertwee, (Ed.) (2017); doi:10.1093/acprof:oso/9780199662685.001.0001, 21 pages.
Gallily, R. et al., "Overcoming the Bell-Shaped Dose-Response of Cannabidiol by Using *Cannabis* Extract Enriched in Cannabidiol," Pharmacology & Pharmacy, 6:75-85 (2015).
Lewis, M. M. et al., "Chemical Profiling of Medical Cannabis Extracts," ACS Omega, 2:6091-6103 (2017).
Billakota et al., "Cannabinoid therapy in epilepsy," Curr Opin Neurol, 32:220-226 (2019).
Dravet, C., "The core Dravet syndrome phenotype," Epilepsia. 52 Suppl 2:3-9. doi: 10.1111/j.1528-1167.2011.02994.x. (2011).

(Continued)

*Primary Examiner* — Sahar Javanmard
(74) *Attorney, Agent, or Firm* — COOLEY LLP

(57) ABSTRACT

Cannabidiol (CBD) is a cannabinoid designated chemically as 2-[(IR,6R)-3-Methyl-6-(1-methylethenyl)-2-cyclohexen-1-yl]-5-pentyl-1,3-benzenediol. Its empirical formula is $C_{21}H_{30}O_2$ and its molecular weight is 314.46. CBD is a cannabinoid that naturally occurs in the *Cannabis sativa* L. plant. CBD is a white to pale yellow crystalline solid which is insoluble in water and soluble in organic solvents. The present invention encompasses the surprising recognition that certain CBD preparations which are prepared from a botanical origin are more effective in treating diseases or disorders than preparations of CBD which are synthetic or purified to the extent no other impurities in the form of other cannabinoids are present. Prior CBD compositions have been prepared such that no psychoactive components, e.g., tetrahydrocannabinol (THC), remain in the final CBD preparation. Surprisingly, the absence of such minor impurities reduces the efficacy of CBD treatment. Such CBD preparations are characterized by chemical components and/or functional properties that distinguish them from prior CBD compositions. One or more components of the preparations described herein provide an unexpectedly synergistic effect when utilized in combination.

30 Claims, 19 Drawing Sheets

(56) References Cited

U.S. PATENT DOCUMENTS

| | | | |
|---|---|---|---|
| 9,630,941 B2 | 4/2017 | Elsohly et al. | |
| 9,949,936 B2 | 4/2018 | Guy et al. | |
| 9,949,937 B2 | 4/2018 | Guy et al. | |
| 9,956,183 B2 | 5/2018 | Guy et al. | |
| 9,956,184 B2 | 5/2018 | Guy et al. | |
| 9,956,185 B2 | 5/2018 | Guy et al. | |
| 9,956,186 B2 | 5/2018 | Guy et al. | |
| 10,092,525 B2 | 10/2018 | Guy et al. | |
| 10,111,840 B2 | 10/2018 | Guy et al. | |
| 10,137,095 B2 | 11/2018 | Guy et al. | |
| 10,583,096 B2 | 3/2020 | Guy et al. | |
| 10,603,288 B2 | 3/2020 | Guy et al. | |
| 10,709,671 B2 | 7/2020 | Guy et al. | |
| 10,709,673 B2 | 7/2020 | Guy et al. | |
| 10,709,674 B2 | 7/2020 | Guy et al. | |
| 10,765,643 B2 | 9/2020 | Guy et al. | |
| 10,807,777 B2 | 10/2020 | Whittle | |
| 10,849,860 B2 | 12/2020 | Guy et al. | |
| 10,918,608 B2 | 2/2021 | Guy et al. | |
| 10,966,939 B2 | 4/2021 | Guy et al. | |
| 11,065,209 B2 | 7/2021 | Guy et al. | |
| 11,065,227 B2 | 7/2021 | Stott et al. | |
| 11,096,905 B2 | 8/2021 | Guy et al. | |
| 11,147,776 B2 | 10/2021 | Stott et al. | |
| 11,147,783 B2 | 10/2021 | Stott et al. | |
| 11,154,516 B2 | 10/2021 | Guy et al. | |
| 11,154,517 B2 | 10/2021 | Wright et al. | |
| 11,160,757 B1 | 11/2021 | Wilkhu et al. | |
| 11,160,795 B2 | 11/2021 | Guy et al. | |
| 11,207,292 B2 | 12/2021 | Guy et al. | |
| 11,229,612 B2 | 1/2022 | Wright et al. | |
| 11,311,498 B2 | 4/2022 | Guy et al. | |
| 11,357,741 B2 | 6/2022 | Guy et al. | |
| 11,400,055 B2 | 8/2022 | Guy et al. | |
| 11,406,623 B2 | 8/2022 | Guy et al. | |
| 11,426,362 B2 | 8/2022 | Wright et al. | |
| 11,446,258 B2 | 9/2022 | Guy et al. | |
| 11,590,087 B2 | 2/2023 | Guy et al. | |
| 11,633,369 B2 | 4/2023 | Guy et al. | |
| 2004/0034108 A1 | 2/2004 | Whittle | |
| 2004/0147767 A1 | 7/2004 | Whittle et al. | |
| 2006/0167283 A1 | 7/2006 | Flockhart et al. | |
| 2007/0238786 A1 | 10/2007 | Hobden et al. | |
| 2008/0112895 A1 | 5/2008 | Kottayil et al. | |
| 2008/0119544 A1 | 5/2008 | Guy et al. | |
| 2009/0036523 A1 | 2/2009 | Stinchcomb et al. | |
| 2010/0273895 A1 | 10/2010 | Stinchcomb et al. | |
| 2011/0033529 A1 | 2/2011 | Samantaray et al. | |
| 2011/0150825 A1 | 6/2011 | Buggy et al. | |
| 2012/0165402 A1 | 6/2012 | Whalley et al. | |
| 2012/0270845 A1 | 10/2012 | Bannister et al. | |
| 2013/0143894 A1 | 6/2013 | Bergstrom | |
| 2014/0343044 A1 | 11/2014 | Ceulemens | |
| 2015/0359756 A1 | 6/2015 | Guy et al. | |
| 2015/0181924 A1 | 7/2015 | Llamas | |
| 2015/0342902 A1 | 12/2015 | Vangara et al. | |
| 2015/0343071 A1 | 12/2015 | Vangara | |
| 2015/0359755 A1 | 12/2015 | Guy et al. | |
| 2016/0166514 A1 | 6/2016 | Guy et al. | |
| 2016/0166515 A1 | 6/2016 | Guy et al. | |
| 2017/0007551 A1 | 1/2017 | Guy et al. | |
| 2017/0239193 A1 | 4/2017 | Guy et al. | |
| 2018/0228751 A1 | 2/2018 | Stott et al. | |
| 2018/0071210 A1 | 3/2018 | Wilkhu et al. | |
| 2019/0167583 A1 | 6/2019 | Shah | |
| 2019/0175547 A1 | 6/2019 | Stott | |
| 2019/0321307 A1 | 6/2019 | Wright et al. | |
| 2019/0365667 A1 | 8/2019 | Wilkhu | |
| 2019/0314296 A1 | 10/2019 | Wright et al. | |
| 2020/0138738 A1 | 1/2020 | Guy et al. | |
| 2020/0179303 A1 | 2/2020 | Guy et al. | |
| 2020/0237683 A1 | 3/2020 | Whalley et al. | |
| 2020/0108027 A1 | 4/2020 | Whalley et al. | |
| 2020/0297656 A1 | 6/2020 | Guy et al. | |
| 2020/0206152 A1 | 7/2020 | Stott et al. | |
| 2020/0206153 A1 | 7/2020 | Whalley et al. | |
| 2020/0352878 A1 | 7/2020 | Guy et al. | |
| 2020/0368179 A1 | 8/2020 | Guy et al. | |
| 2021/0015789 A1 | 1/2021 | Guy et al. | |
| 2021/0052512 A1 | 2/2021 | Guy et al. | |
| 2021/0059949 A1 | 3/2021 | Wilkhu et al. | |
| 2021/0059960 A1 | 3/2021 | Wilkhu et al. | |
| 2021/0059976 A1 | 3/2021 | Wilkhu et al. | |
| 2021/0093581 A1 | 4/2021 | Guy et al. | |
| 2021/0169824 A1 | 6/2021 | Guy et al. | |
| 2021/0177773 A1 | 6/2021 | Guy et al. | |
| 2021/0230145 A1* | 7/2021 | Blankman | C07D 295/205 |
| 2021/0290565 A1 | 9/2021 | Guy et al. | |
| 2021/0330636 A1 | 10/2021 | Guy et al. | |
| 2022/0000800 A1 | 1/2022 | Guy et al. | |
| 2022/0008355 A1 | 1/2022 | Guy et al. | |
| 2022/0023232 A1 | 1/2022 | Guy et al. | |
| 2022/0040155 A1 | 2/2022 | Guy et al. | |
| 2022/0062211 A1 | 3/2022 | Stott et al. | |
| 2022/0096397 A1 | 3/2022 | Wright et al. | |

FOREIGN PATENT DOCUMENTS

| | | |
|---|---|---|
| GB | 2 377 633 A | 1/2003 |
| GB | 2 380 129 A | 4/2003 |
| GB | 2 381 194 A | 4/2003 |
| GB | 2 485 291 A | 5/2012 |
| GB | 2 487 183 A | 7/2012 |
| GB | 2 530 001 A | 3/2016 |
| GB | 2 531 282 A | 4/2016 |
| GB | 2542 155 A | 3/2017 |
| GB | 2 548 873 A | 10/2017 |
| WO | WO 01/95899 A2 | 12/2001 |
| WO | WO 02/064109 A2 | 8/2002 |
| WO | WO 02/089945 A2 | 11/2002 |
| WO | WO 2004/016246 A1 | 2/2004 |
| WO | WO 2004/016277 A2 | 2/2004 |
| WO | WO 2004/026802 A1 | 4/2004 |
| WO | WO 2005/120478 A1 | 12/2005 |
| WO | WO 2006/017892 A1 | 2/2006 |
| WO | WO 2006/133941 A1 | 12/2006 |
| WO | WO 2007/052013 A1 | 5/2007 |
| WO | WO 2007/083098 A1 | 7/2007 |
| WO | WO 2007/138322 A1 | 12/2007 |
| WO | WO 2009/007697 A1 | 1/2009 |
| WO | WO 2009/093018 A1 | 7/2009 |
| WO | WO 2011/001169 A1 | 1/2011 |
| WO | WO 2011/121351 A1 | 10/2011 |
| WO | WO 2012/093255 A1 | 7/2012 |
| WO | WO 2012/160358 A1 | 11/2012 |
| WO | WO 2013/045891 A1 | 4/2013 |
| WO | WO 2015/142501 A1 | 9/2015 |
| WO | WO 2015/184127 A1 | 12/2015 |
| WO | WO 2015/193667 A1 | 12/2015 |
| WO | WO 2015/193668 A1 | 12/2015 |
| WO | WO 2016/059403 A1 | 4/2016 |
| WO | WO 2015/187988 A1 | 7/2016 |
| WO | WO 2018/115962 A1 | 6/2018 |
| WO | WO 2018/234811 A1 | 12/2018 |
| WO | WO 2019/207319 A1 | 10/2019 |

OTHER PUBLICATIONS

Eadie, "Shortcomings in the current treatment of epilepsy," Expert Rev Neurother, 12(12):1419-27 (2012).

EPIDIOLEX® (cannabidiol) oral solution, CV, Prescribing Information, 2018, 30 pages; https://www.accessdata.fda.gov/drugsatfda_docs/label/2018/210365lbl.pdf.

FDA, "Orange Book: Approved Drug Products with Therapeutic Equivalence Evaluations," Patent and Exlusitivy for: N210365, 3 pages; https://www.accessdata.fda.gov/scripts/Cder/ob/patent_info.cfm?Product_No=001&Appl_No=210365&Appl_type=N, accessed on Jun. 14, 2019.

Gaston et al., "Improvement in quality of life ratings after one year of treatment with pharmaceutical formultion of cannabidiol (CBD)," Epilepsia, 58(Suppl.5):S5-S199, Abstract p0899 (2017); doi:10.111/epi.13944.

(56) References Cited

OTHER PUBLICATIONS

Hagopian et al., Does CBD improve non-seizure outcomes in pediatric epilepsy patients? AES Annual Meeting, 2018, Poster Abstract 2.280, 3 pages.
Kwan et al., "Definition of drug resistant epilepsy: consensus proposal by the ad hoc Task Force of the ILAE Commission on Therapeutic Strategies," Epilepsia. Jun. 2010;51(6):1069-77. doi:10.1111/j.1528-1167.2009.02397.x. Epub Nov. 3, 2009. Erratum in: Epilepsia. Sep. 2010; 51(9):1922.
Press et al., "Parenteral reporting of response to oral cannabis extracts for treatment of refractory epilepsy," Epilepsy Behav, 45:49-52 (2015).
Rosenberg et al., "Quality of Life in Childhood Epilepsy in pediatric patients enrolled in a prospective, open-label clinical study with cannabidiol," Epilepsia, 58:e96-e100 (2017).
Seidenberg et al., "Association of epilepsy and comorbid conditions," Future Neurol., 4(5):663-668 (2009); doi:10.2217/fnl.09.32.
Thurman et al., "Standards for epidemiologic studies and surveillance of epilepsy," Epilepsia, 52 (Suppl 7):2-26 (2011).
Tzadok et al., "CBD-enriched medical cannabis for intractable pediatric epilepsy The current Israeli experience," Seizure, 35:41-44 (2016).
U.S. Appl. No. 17/638,629, filed Feb. 25, 2022.
U.S. Appl. No. 17/689,607, filed Mar. 8, 2022.
U.S. Appl. No. 17/689,245, filed Mar. 8, 2022.
U.S. Appl. No. 17/705,443, filed Mar. 28, 2022.
Bergamaschi, M. M. et al., "Safety and Side Effects of Cannabidiol, a *Cannabis sativa* Constituent," Current Drug Safety, 6:237-249 (2011).
Camfield, P. R., "Definition and natural history of Lennox-Gastaut syndrome," Epilepsia, 52(Suppl. 5):3-9 (2011).
Carvill, G. L. et al., "GABRA1 and STXBP1: Novel generic causes of Dravet Syndrome," Neurology, 82:1245-1253 (2014).
Chiron, C. & Dulac, O., "The Pharmacologic Treatment of Dravet Syndrome," Epilepsia, 52 (Suppl. 2):72-75 (2011).
Chiron, S., "Stiripentol for the treatment of Dravet syndrome," Orphan Drugs: Research and Reviews, 4:29-38 (2014).
Cilio, M. R. et al., "The case for assessing cannabidiol I epilepsy," Epilepsia, 55(6):787-790 (2014).
Clinical Trials.Gov [online], Identifier: NCT02224690, A Study to Investigate the Efficacy and Safety of Cannabidiol (GWP42003-P; CBD) as Adjunctive Treatment for Seizures Associated With Lennox-Gastaut Syndrome in Children and Adults (GWPCARE4) Jazz Pharmaceuticals, U.S. National Library of Medicine, last update posted Sep. 8, 2022, 3 pages; Retrieved from https://clinicaltrials.gov/ct2/show/NCT02224690.
Collins, T. R., Collins TR. What Neurologists are Doing About Medical Marijuana?, Neurology Today, Apr. 17, 2014, vol. 4, issue 8, 8 pages.
Consroe, et al., "Controlled clinical trial of cannabidiol in Huntington's Disease," Pharmacology Biochemistry & Behavior, 40:701-708 (1991).
Crumrine, P. K., "Management of Seizures in Lennox-Gastaut Syndrome," Pediatr Drugs, 13(2):107-118 (2011).
Cunha, J. M. et al., "Chronic Administration of Cannabidiol to Healthy Volunteers and Epileptic Patients," Pharmacology, 21:175-185 (1980).
Devinsky, et al., "Cannabidiol: Pharmacology and potential therapeutic role in epilepsy and other neuropsychiatric disorders," Epilepsia, 55(6):791-802 (2014).
DIACOMIT™ Product Monograph, Submission Control 142417, Date of Preparation, Dec. 19, 2012, 37 pages.
Gedde et al., "3.330: Whole Cannabis Extract of High Concentration Cannabidiol May Calm Seizures in Highly Refractory Pediatric Epilepsies," American Epilepsy Society, Dec. 2013, 449-450.
Gedde, Retrospective Case Review of High CBD, Low THC Cannabis Extract (Realm Oil) for Intractable Seizure Disorders, 2013 Realm of Caring Foundation, 4 pages.

GWPharm [online], "GW Pharmaceuticals Provides Update on Orphan Program in Childhood Epilepsy for Epidiolex®," GW Pharmaceuticals Press Release, Nov. 15, 2013, 5 pages.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, 2 pages; retrieved on Mar. 1, 2017, URL https://www.gwpharm.com/about-us/news/gw-pharmaceuticals-announces-epidiolex%C2%AE-receives-fast-track-designation-fda-treatment.
"GW Pharmaceuticals Receives Orphan Drug Designation by FDA for Epidiolex® in the Treatment of Lennox-Gastaut Syndrome," Feb. 28, 2014 08:00 ET | Source: GW Pharmaceuticals plc; 3 pages; https://www.globenewswire.com/en/news-release/2014/02/28/614497/26153/en/GW-Pharmaceuticals-Receives-Orphan-Drug-Designation-by-FDA-for-Epidiolex-R-in-the-Treatment-of-Lennox-Gastaut-Syndrome.html.
Gresham, J. et al., "Treating Lennox-Gastaut syndrome in epileptic pediatric patients with third-generation rufinamide," Neuropsychiatric Disease and Treatment, 6:639-645 (2010).
Hillig, K. W. & Mahlberg, P. G., "A chemotaxonomic analysis of cannabinoid variation in *Cannabis* (Cannabaceae)," American Journal of Botany, 91(6):966-975 (2004).
Jiang, R. et al., "Cannabidiol Is a Potent Inhibitor of the Catalytic Activity of Cytochrome P450 2019," Drug Metab. Pharmacokinet., 28(4):332-338 (2013).
Jones, N. A. et al., "Cannabidiol exerts anti-convulsant effects in animal models of temporal lobe and partial seizures," Seizure, 21:344-352 (2012).
Kalepu, S. et al., "Oral lipid-based drug delivery systems—an overview," Acta Pharmaceutica Sinica B., 3(6):361-372 (2013).
Leahy, J. T. et al., "Clobazam as an adjunctive therapy in treating seizures associated with Lennox-Gastaut syndrome," Neuropsychiatric Disease and Treatment, 7:673-681 (2011).
Lindamood and Colasanti, "Effects of delta 9-tetrahydrocannabinol and cannabidiol on sodium-dependent high affinity choline uptake in the rat hippocampus," J Pharmacology Experimental Therapeutics, 213(2):216-221 (1980).
Maa et al., "The case for medical marijuana I epilepsy," Epilepsia 55(6):783-786, 2014.
MARINOL® Product Description, NDA 18-651/S-025 and S-026, Jul. 2006, pp. 3-13.
Oguni, H. et al., "Long-Term Prognosis of Lennox-Gastaut Syndrome," Epilepsia, 37(Suppl 3):44-47 (1996).
ONFI™ (clobazam) tablets Prescribing Information, NDA 202067 Onfi (clobazam) Tablets for oral use FDA Approved Labeling Text, dated Oct. 21, 2011, 28 pages.
Pelliccia, et al., "Treatment with CBD in oily solution of drug-resistant paediatric epilepsies," Available online Sep. 2, 2010, Retrieve Apr. 14, 2021, 2 pages; http://www.gwpharm.com/uploads/pelliccia-2002-treatmentwithcbdinoilysolutionofdrug-resistantpediatricepilepsies.pdf.
Porter et al., "Report of a parent survey of cannabidiol-enriched cannabis use in pediatric treatment-resistant epilepsy," Epilepsy Behav., 29(3):574-577 (2013).
"Pot or not? Why parents of kids with epilepsy want access to marijuana treatment," CTVNews.ca Staff, Published Thursday, Jul. 18, 2013; Last Updated Thursday, Jul. 18, 2013, 2 pages; https://www.ctvnews.ca/health/health-headlines/pot-or-not-why-parents-of-kids-with-epilepsy-want-access-to-marijuana-treatment-1.1372695?cache=.
Saade, D. & Joshi, C., "Pure Cannabidiol in the Treatment of Malignant Migrating Partial Seizures in Infancy: A Case Report," Pediatric Neurology, 52:544-547 (2015); http://dx.doi.org/10.1016/j.pediatrneurol.2015.02.008.
Schafroth, M. A. et al., "Sterodivergent Total Synthesis of $\Delta^9$-Tetrahydrocannabinols," Angew. Chem. Int. Ed., 53:13898-13901 (2014).
Scheffer, I. E., "Diagnosis and long-term course of Dravet syndrome," Eur J of Paediatric Neurology 16 (2012) S5-S8.
Silva, R. et al., "Clobazam as Add-on Therapy in Children with Epileptic Encephalopathy," Can. J. Neurol. Sci., 33:209-213 (2006).
Smith, R. M. & Kempfert, K. D., "$\Delta^1$-3,4-CIS-Tetrahydrocannabinol in Cannabis Sativa," Phytochemistry, 16:1088-1089 (1977).

(56) References Cited

OTHER PUBLICATIONS

"University of Utah doctors: Say 'yes' to cannabis oil for kids," By Kirsten Stewart The Salt Lake Tribune, Nov. 13, 2013, 4 pages.
Vanstraten, A.F. et al., "Update on the Management of Lennox-Gastaut Syndrome," Pediatric Neurology, 47:153-161 (2012).
Young, S., "Marijuana stops child's severe seizures," CNN Health online, Aug. 7, 2013, 4 pages; https://www.cnn.com/2013/08/07/health/charlotte-child-medical-marijuana/index.html#:~:text=The%20first%20time%20Paige%20Figi, seizures%20stopped%20for%20seven%20days.&text=The%20marijuana%20strain%20Charlotte%20and,has%20been%20named%20after%20her.
Adams, R. et al., "Isolation of Cannabinol, Cannabidiol and Quebrachitol from Red Oil of Minnesota Wild Hemp," J. Am. Chem. Soc. 1940, 62, 8, 2194-2196.
Allen G., "Florida Bill Would Allow Medical Marijuana for Child Seizures," Jan. 16, 2014, retrieved from https://www.npr.org/sections/health-shots/2014/01/16/262481852/florida-bill-would-allow-marijuana-extract-for-child-seizures, 16 pages.
Amada, N. et al., "Cannabidivarin (CBDV) suppresses pentylenetetrazole (PTZ)-induced increases in epilepsy-related gene expression," 2013, PeerJ, 1:e214; 18 pages; http://dx.doi.org/10.7717/peerj.214.
Approval Letter for NDA 210365 Epidiolex, Jun. 25, 2018, 12 pages.
Arzimanoglou et al., "All children who experience epileptic falls do not necessarily have Lennox-Gastaut syndrome . . . but many do," Epileptic Disord. 2011, 13: S3-S13 (2011).
Bancaud, J. et al., "Proposal for revised clinical and electroencephalographic classification of epileptic seizures. From the Commission on Classification and Terminology of the International League Against Epilepsy," Epilepsia, Aug. 1981;22(4):489-501. doi: 10.1111/j.1528-1157.1981.tb06159.x.
Bell, J., "Treatment With CBD in Oily Solution of Drug-Resistant Paediatric Epilepsies," Oct. 18, 2011, 3 pages; https://www.420magazine.com/community/threads/treatment-with-cbd-in-oily-solution-of-drug-resistant-paediatric-epilepsies.154896/.
Bienenstock, D., "A Comprehensive History of Marijuana's Epilepsy-Treating Compound, CBD," Jun. 2014, Vice Article, retrieved from https://www.vice.com/da/article/mv53yp/desperately-seeking-cbd, 17 pages.
Carlini, E. A. et al., "Letter: Cannabidiol and Cannabis sativa extract protect mice and rats against convulsive agents," J Pharm Pharmacol. Aug. 1973;25(8):664-5. doi: 10.1111/j.2042-7158.1973.tb10660.x.
Chu-Shore, C. J. et al., "The natural history of epilepsy in tuberous sclerosis complex," Epilepsia, 51(7):1236-1241, 2010; doi: 10.1111/j.1528-1167.2009.02474.
Clinical Trials.Gov [online], Identifier: NCT02091206, A Dose Ranging Pharmacokinetics and Safety Study of GWP42003-P in Children With Dravet Syndrome (GWPCARE1), Jazz Pharmaceuticals, U.S. National Library of Medicine, last update posted Sep. 28, 2022, 9 pages; Retrieved from https://clinicaltrials.gov/ct2/show/NCT02091206.
Clinical Trials.Gov [online], Identifier: NCT02006628, A study to compare the change in symptom severity in participants with schizophrenia or related psychotic disorderwhen treated with GWP42003 or placebo in conjunction with existing anti-psychotic therapy over a period of six weeks, Jazz Pharmaceuticals, U.S. National Library of Medicine, last update posted Sep. 28, 2022, 9 pages; Retrieved from https://clinicaltrials.gov/ct2/show/NCT02006628.
Clinical Trials.Gov [online], Identifier: NCT02091375, Antiepileptic Efficacy Study of GWP42003-P in Children and Young Adults WithDravet Syndrome (GWPCARE1), Jazz Pharmaceuticals, U.S. National Library of Medicine, last update posted Sep. 28, 2022, 40 pages; Retrieved from https://www.clinicaltrials.gov/ct2/show/NCT02091375.
Conry, J. A. et al., "Clobazam in the treatment of Lennox-Gastaut syndrome," Epilepsia, 50:1158-1166 (2009).
Consroe, et al., "Anticonvulsant interaction of cannabidiol and ethosuximide in rats," J Pharm Pharmacol., 29(8):500-501 (1977); doi: 10.1111/j.2042-7158.1977.tb11378.x.
Consroe, et al., "Cannabidiol—antiepileptic drug comparisons and interactions in experimentally induced seizures in rats," J Pharmacol Exp Ther., 201(1):26-32 (1977).
Cotterell, A., "How One Young Girl Could Change Idaho's Strict Marijuana Laws," Jun. 17, 2014; https://www.knkx.org/law/2014-06-19/how-one-young-girl-could-change-idahos-strict-marijuana-laws, 8 pages.
Cotter, B., "Medicinal marijuana stops seizures, brings hope to little girl," The Gazette, Jun. 9, 2013, 8 pages; https://gazette.com/health/medicinal-marijuana-stops-seizures-brings-hope-to-a-little-girl/article_520b074e-5c46-5d75-af95-bdd060f4a8b9.html.
Curatolo, P. et al., "Management of epilepsy associated with tuberous sclerosis complex (TSC): Clinical recommendations," European Journal of Paediatric Neurology, 16:582-586 (2012).
Depakene (valproic acid) capsules and oral solution, CV, Prescribing Information, 1978, 54 pages; https://www.accessdata.fda.gov/drugsatfda_docs/label/2013/018081s056lbl.pdf.
Dilantin-125®, NDA 08762 Dilantin-125 (Phenytoin Oral Suspension, USP) FDA Approved Labeling Text dated Feb. 2013, 15 pages.
DiMarzo, V., Declaration Under 37 C.F.R. 1.132, dated Aug. 24, 2017, 21 pages.
Dreifus, et al., "Proposal for Revised Clinical and Electroencephalographic Classification of Epileptic Seizures," Epilepsie., 22:489-501 (1981).
Epilepsy Patients Flock to Colorado after Medical Pot Gives Them Hope, Nov. 18, 2013, CBS Colorado News, 4 pages.
Elsohly, M. & Gul, W., "Chemical constituents of marijuana: The complex mixture of natural cannabinoids," Life Sciences, 78:539-548 (2005).
FDA Guideline for Submitting Supporting Documentation in Drug Applications for the Manufacture of Drug Substances, published in 1987, 20 pages.
FDA'S Guidance for Industry Q3A Impurities in New Drug Substances, Revision 2, Jun. 2008, 17 pages.
Fernandez-Ruiz, J. et al., "Cannabidiol for neurodegenerative disorders: important new clinical applications for this phytocannabinoid?" British Journal of Pharmacology, 75(2):323-333 (2012).
Flatow, N., "How Medical Marijuana Is Giving a Six-Year-Old Boy New Life," Sep. 18, 2012, 2 pages; https://archive.thinkprogress.org/how-medical-marijuana-is-giving-a-six-year-old-boy-new-life-b5a486fb1d48/.
Gaoni, Y. & Mechoulam, R., "The Isolation and Structure of $\Delta^1$-Tetrahydrocannabinol and Other Neutral Cannabinoids from Hashish," J Am Chem Soc. Jan. 13, 1971;93(1):217-24. doi: 10.1021/ja00730a036.
Gaoni, Y. & Mechoulam, R., "Isolation, Structure, and Partial Synthesis of an Active Constituent of Hashish," J. Am. Chem. Soc. 1964, 86, 8, 1646-1647.
Garde, D., "GW Pharmaceuticals Announces Physician Reports of Epidiolex Treatment Effect in Children and Young Adults With Treatment-Resistant Epilepsy From Physician-Led Expanded Access Treatment Program," Jun. 17, 2014, 4 pages; https://www.fiercebiotech.com/biotech/gw-pharmaceuticals-announces-physician-reports-of-epidiolex-r-treatment-effect-children-and.
Gardner [online], "Comes Now Epidiolex (FDA Approves IND Studies of CBD)," BeyondTHC.com, Oct. 22, 2013, retrieved on Jan. 31, 2018, http://www.beyondthc.com/comes-now-epidiolex-fda-approves-ind-studies-of-cbd, 4 pages.
Gedde, "Clinical Experience with Cannabis in Treatment-Resistant Pediatric Epilepsy," http://www.theroc.us/images/gedde presentation.pdf, Sep. 9-11, 2014.
Geffrey, A. et al., "Cannabidiol (CBD) Treatment for Refractory Epilepsy in Tuberous Sclerosis Complex (TSC)," Dec. 4, 2014; www.aesnet.org, Abstract 2.427, 2 pages.
Gloss, D. & Vickrey, B., "Cannabinoids for epilepsy (Review)," Cochrane Database of Systematic Reviews 2014, Issue 3. Art. No. CD009270, 9 pages; DOI: 10.1002/14651858.CD009270.pub3.
Green, R., "CBD : An Unconventional Therapy," The Wayback Machine, Mar. 24, 2014, 5 pages; https://web.archive.org/web/20140818171737/http://www.nugs.com/article/cbd-an-unconventional-therapy.html.

(56) References Cited

OTHER PUBLICATIONS

Guimares, et al., "Antianxiety effect of cannabidiol in the elevated plus-maze," Psychopharmacology (Berl)., 100(4):558-9 (1990); doi: 10.1007/BF02244012.

FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.

Hanus et al., "Phyto-cannabinoids: a unified critical inventory," Review Article, Natural Product Reports; Royal Society of Chemistry, vol. 33, No. 12, Dec. 2016, pp. 1347, 1448, 37 pages.

Haller, S. & Carroll, I., "Medical marijuana for kids? Some praise results while others worry about risks," Jul. 9, 2013, 3 pages; https://www.nbcnews.com/healthmain/medical-marijuana-kids-some-praise-results-while-others-worry-about-6c10506407.

Hefler, J., "Parents of epileptic N.J. tot lament medical marijuana delays," The Philadelphia Enquirer, Jun. 22, 2013, 5 pages; https://www.inquirer.com/philly/health/20130623_Parents_of_epileptic_N_J_tot_lament_medical_marijuana_delays.html.

Hegde, M. et al., "Seizure exacerbation in two patients with focal epilepsy following marijuana cessation," Epilepsy & Behavior, 25:563-566 (2012).

Hill, A. J. et al., "Cannabidivarin is anticonvulsant in mouse and rat," British Journal of Pharmacology (2012) 167 1629-1642.

Hill, A. J. et al., "Phytocannabinoids as novel therapeutic agents in CNS disorders," Pharmacology & Therapeutics, 133:79-97 (2012).

Holmes, G. L. et al., "Tuberous Sclerosis Complex and Epilepsy: Recent Developments and Future Challenges," Epilepsia, 48(4):617-630, 2007.

ICE Epilepsy Alliance, The Dravet Syndrome Spectrum, Nov. 2008, 2 pages.

Izzo, et al., "Non-psychotropic plant cannabinoids: new therapeutic opportunities from an ancient herb," Trends in Pharmacological Sciences, 30(10):515-527 (2009).

Jacobson, C., "Treating Epilepsy with Pharmaceutical-Grade CBD", Cannabis Science Today, Podcast, 2023, transcript timeline 4 pages; https://agriculturalgenomics.org/podcast/season1/treating-epilepsy-with-pharmaceutical-grade-cbd/.

Jones, P. G. et al., "Cannabidiol," Acta Cryst., B33:3211-3214 (1977).

Kassai et al., "Severe Myoclonic epilepsy in Infancy: A Systematic Review and a Meta-Analysis of Individual Patient Data," Epilepsia, 49(2):343-348 (2008).

Kerr, D. N. S. & Pillai, P. M., "Clobazam as adjunctive treatment in refractory epilepsy," British Medical Journal, 286:1246-1247 (1983).

Kopka, M., "Cannabinoids in the treatment of epilepsy—an updated review," Journal of Epileptology, 2019, 27:35-42; 10.21307/jepil-2019-004.

Krasowski, M. D., "Antiepileptic Drugs. Therapeutic Drug Monitoring of the Newer Generation Drugs," Jun. 2013, Clinical Laboratory News, https://www.aacc.org/cln/articles/2013/june/antiepileptic-drugs, 6 pages.

Leonard, B. E., "Therapeutic Uses of Cannabis," British Medical Association (BMA). Harwood Academic Publishers, UK. 1997, pp. 592.

Loscher, W. & Rogawski, M. A., "How theories evolved concerning the mechanism of action of barbiturates," Epilepsia, 53(Suppl. 8): 12-25, 2012; doi: 10.1111/epi.12025.

Lowenstein, "Chapter 363: Seizures and Epilepsy," Diseases of the Central Nervous System, 2498-2512 (2008).

Manno, "Status Epilepticus: Current Treatment Strategies," The Neurohospitalist, 1(1):23-31 (2011).

Marks, W. J. et al., "Management of Seizures and Epilepsy," Am Fam Physician. 1998;57(7):1589-1600.

Masangkay, E. G., "FDA Confirms GW Pharmaceuticals' IND for Epidiolex Trial in Dravet Syndrome," May 9, 2014, 2 pages; FDA Confirms GW Pharmaceuticals' IND for Epidiolex Trial in Dravet Syndrome.

Mechoulam, et al., "Cannabidiol: An Overview of Some Pharmacological Aspects," J Clin Pharmacol, 42:11S-19S (2002).

Mechoulam, et al., Toward drugs derived from cannabis, Naturwissenschaften, 65(4):174-9 (1978).

Mechoulam, R. et al., "Cannabidiol—Recent Advances," Chemistry & Biodiversity, vol. 4, pp. 1678-1692 (2007).

Mechoulam, R., "Conversation with Ralph Mechoulam," Addiction Jun. 2007;102(6):887-93. doi: 10.1111/j.1360-0443.2007.01795.x.

Mechoulam, R. & Parker, L. A., "The Endocannabinoid System and the Brain," Annu. Rev. Psychol. 2013. 64:21-47.

Mechoulam, R. & Parker, L. A., "Towards a better cannabis drug," British Journal of Pharmacology (2013) 170 1363-1364.

Moore, Y. et al., "Cannabidiol reduced frequency of convulsive seizures in drug resistant Dravet Syndrome," Structured Abstracts of Sentinel Articles: Picket, first published Sep. 22, 2017, reported in Arch Dis Child Educ Pract Ed Oct. 2018, vol. 103, No. 5, 2 pages. Abstract.

New Drug Application No. 210365 for Epidiolex (cannabidiol) 100 mg/ml oral solution, Jun. 25, 2018, 12 pages.

[No Author Listed], "High Rollers Bet on Cannabidiol (CBD)—Medical Marijuana Patients Come Up Short," Mar. 3, 2013, 9 pages; https://www.420magazine.com/community/threads/high-rollers-bet-on-cannabidiol-cbd-%E2%80%94-medical-marijuana-patients-come-up-short.185325/.

[No Author Listed], "Selected Media Examples of Pediatric Applications of Cannabidiol (CBD)," Jun. 30, 2013, 4 pages; https://www.420magazine.com/community/threads/selected-media-examples-of-pediatric-applications-of-cannabidiol-cbd.192155/.

[No Author Listed], "Medical Cannabis Community Wants to Remain Apart," Medical Marijuana News, Apr. 3, 2013, 3 pages; Kitsap Peninsula Business Journal, available at: https://www.420magazine.com/community/threads/medical-cannabis-community-wants-to-remain-apart.186955/.

[No Author Listed], The Reuters Staff, BRIEF-GW Pharma receives FDA fast-track designation for Dravet syndrome treatment, Jun. 6, 2014, 1 page; https://www.reuters.com/article/gwpharmaceuticals-brief/brief-gw-pharma-receives-fda-fast-track-designation-for-dravet-syndrome-treatment-idUSFWN0OL01D20140606.

[No Author Listed], "Medical Marijuana for N.J. Children? It's All in Gov. Christie's Hands," CBS News New York, Jun. 27, 2013, 3 pages; https://www.cbsnews.com/newyork/news/medical-marijuana-for-n-j-children-its-all-in-gov-christies-hands/.

Ng et al., "Long-term Safety and Efficacy of Clobazam for Lennox-Gastaut Syndrome: Interim Results of an Open-Label Extension Study," Epilepsy & Behaviour, 25(4):687-694 (2012).

Oguni, H. et al., "Severe myoclonic epilepsy in infants—a review based on the Tokyo women's Medical University series of 84 cases," Brain Dev., 23:736-748 (2010).

Panikasiwill, D. et al., "An endogenous cannabinoid (2-AG) is neuroprotective after brain injury," Nature 413:527-531 (2001).

Pellicia, et al.. International Association for Cannabis as Medicine, IACM 3rd Conference on Cannabinoids in Medicine, Sep. 9-10, 2005, 2005 Conference on Cannabinoids in Medicine, 72 pages.

Potter, C., "Cannabis Extract Brings Hope for Children with Epilepsy," Dec. 3, 2013, 3 pages.

Purcarin, G. & Ng, Y-T., "Experience in the use of clobazam in the treatment of Lennox-Gastaut syndrome," Ther Adv Neurol Disord 2014, vol. 7(3):169-176.

Ragona, F. et al., "Dravet syndrome: early clinical manifestations and cognitive outcome in 37 Italian patients," Brain Dev., 32:71-77 (2010).

Rowe, R. C. et al., "Handbook of Pharmaceutical Excipients," Pharmaceutical Press and American Pharmacists Association 2009, pp. 17-19; https://www.academia.edu/16731682/Handbook_of_Pharmaceutical_Excipients_6th_Edition.

Smith, R. M., "Identification of Butyl Cannabinoids in Marijuana," Journal of Forensic Sciences, 42:610-618 (1997).

Specchio, L. M. & Beghi, E., "Should Antiepileptic Drugs Be Withdrawn in Seizure-Free Patients?" CNS Drugs, 18(4):201-212 (2004).

Stewart, K., "Families migrating to Colorado for a medical marijuana miracle," Nov. 11, 2013, 8 pages; https://archive.sltrib.com/article.php?id=57052556&itype=CMSID.

(56) References Cited

OTHER PUBLICATIONS

Stinchcomb, A. L. et al., "Human skin permeation of Δ8-tetrahydrocannabinol, cannabidiol and cannabinol," JPP 2004, 56: 291-297.
Thiel, E. A., "Managing Epilepsy in Tuberous Sclerosis Complex," J Child Neurol 2004;19:680-686.
Tose, L. V. et al., "Isomeric separation of cannabinoids by UPLC combined with ionic mobility mass spectrometry (TWIM-MS)—Part I," International Journal of Spectrometry, 418:112-121 (2017).
Trost, B. M. & Dogra, K., "Synthesis of (-)-Δ$^9$-trans-Tetrahydrocannabinol: Stereocontrol via Mo-Catalyzed Asymmetric Allylic Alkylation Reaction," Organic Letters, 9(5):861-863 (2007).
Van Bakel et al., "The draft genome and transcriptome of Cannabis sativa," Genome Biology 2011, 12:R102, 18 pages; http://genomebiology.com/2011/12/10/R102 (Oct. 24, 2011).
Whittle et al., (2001). Prospects for New Cannabis-Based Prescription Medicines. Journal of Cannabis Therapeutics. 1(3-4); doi: 10.1300/J175v01, 1(3-4), 23 pages.
Wilkey, R., "'Weed Wars': Five-Year-Old Takes Medical Marijuana on Reality Show (Video)", Dec. 10, 2011, 7 pages; https://www.huffpost.com/entry/weed-wars-five-year-old-smokes-marijuana_n_1140351.
Zhornitsky & Potvin, "Cannabidiol in Humans—The Quest for Therapeutic Targets," Pharmaceuticals, 5:529-552 (2012).
Zuardi, A. W., "Cannabidiol: from an inactive cannabinoid to a drug with wide spectrum of action," Rev Bras Psiquiatr. 2008;30(3):271-80.
U.S. Appl. No. 62/004,495, filed May 29, 2014, Vangara et al.
U.S. Appl. No. 61/969,070, filed Mar. 21, 2014, Kane et al.
U.S. Appl. No. 14/724,351, filed May 28, 2015, Vangara et al.
AFINITOR®(everolimus) tablets, for oral use, and AFINITOR DISPERZ®(everolimus tablets for oral suspension) Prescribing Information, 2009, 49 pages.
Akiyama, M. et al., "Dravet Syndrome:A Genetic Epileptic Disorder," Acta. Med. Okayama, 66(5):369-376 (2012).
Ames et al., "Anticonvulsant effect of cannabidiol," S Afr Med J., 69(1):14 (1986), 1 page.
Bhattacharyya, S. et al., "Modulation of mediotemporal and ventrostriatal function in humans by Delta9-tetrahydrocannabinol: a neural basis for the effects of Cannabis sativa on learning and psychosis," Arch Gen Psychiatry, 66(4):442-451 (2009); doi:10.1001/archgenpsychiatry. 2009 .17.
Carlini et al., "Hypnotic and antiepileptic effects of cannabidiol," J Clin Pharmacol., 21:417S-427S (1981).
Consroe et al. "Anticonvulsant nature of marihuana smoking," JAMA, 234(3):306-307 (1975).
Consroe et al. "Anticonvulsant drug antagonism of delta9tetrahydrocannabinol-induced seizures in rabbits," Res Commun Chem Pathol Pharmacol., 16(1):1-13 (1977).
Consroe et al. "Effects of cannabidiol on behavioral seizures caused by convulsant drugs or current in mice," Eur J Pharmacol., 83(3-4):293-298 (1982).
Consroe et al., "Open label evaluation of cannabidiol in dystonic movement disorders," International Journal of Neuroscience, 30(4):277-282 (1986); doi: 10.3109/00207458608985678.

"Cannabidiols: Potential Use in Epilepsy & Other Neurological Disorders." Cannabidiol Conference at NYU School of Medicine, Oct. 2013. NYU Langone Health. Retrieved from the Internet Nov. 2019. <URL: http://faces.med.nyu.edu/research-education/cannabidiol-conference>, 4 pages.
Grotenhermen et al., "The Therapeutic Potential of Cannabis and Cannabinoids," Dtsch Arztebl Int, 109(29-30): 495-501 (2012); doi:10.3238/arztebl.2012.0495.
Gupta Video 2013, Weed—CNN Special; https://www.youtube.com/watch?v=Z3IMfl1_K6U.
Jacobson, "Survey of Current Cannabidiol Use in Pediatric Treatment-Resistant Epilepsy," Poster, Apr. 22, 2013, 1 page.
Jones et al., "Cannabidiol Displays Antiepileptiform and Antiseizure Properties in Vitro and in Vivo," J Pharmacol Exp Ther., 332(2):559-577 (2010).
Kramer et al., "Febrile infection-related epilepsy syndrome (FIRES): pathogenesis, treatment, and outcome: a multicenter study on 77 children," Epilepsia, 52(11):1956-1965 (2011); doi:10.1111/j.1528-1167.2011.03250.x. Epub Aug. 29, 2011.
Malfait et al., "The nonpsychoactive cannabis constituent cannabidiol is an oral anti-arthritic therapeutic in murine collagen-induced arthritis," PNAS, 97(17):9561-9566 (2000).
Mechoulam et al., "Cannabidiol: an overview of some chemical and pharmacological aspects. Part I: chemical aspects," Chemistry and Physics of Lipids, 121:35-43 (2002).
Montenegro et al., "Efficacy of Clobazam as Add-on Therapy for Refractory Epilepsy: Experience at a US Epilepsy Center," Clinical Neuropharmacology, 31(6):333-338 (2008).
Pertwee, "The Pharmacology and Therapeutic Potential of Cannabidiol," Cannabinoids, Chapter 3, DiMarzo, V. (Ed.), pp. 32-83 (2004).
Romano et al., "Inhibition of colon carcinogenesis by a standardized Cannabis sativaextract with high content of cannabidiol," Phytomedicine, 21:631-639 (2014).
Scuderi et al., "Cannabidiol in medicine: a review of its therapeutic potential in CNS disorders," Phytother Res., 23(5):597-602 (2009).
Sun et al., "Comparative study of organic solvent and water-soluble lipophilic extractives from wheat straw I: yield and chemical composition," j Wood Sci, 49:47-52 (2003).
Thompson et al., "Comparison of acute oral toxicity of cannabinoids in rats, dogs and monkeys," Toxicology and Applied Pharmacology, vol. 25, Issue 3, pp. 363-372 (1973).
Uliss et al., "The conversion of 3,4-CIS-to 3,4-TRANS-cannabinoids," Tetrahedron, 34:1885-1888 (1978).
Wallace et al., "Assessment of the role of CB 1 receptors in cannabinoid anticonvulsant effects," Eur J Pharmacol., 428(1):51-57 (2001).
Weed Wars, Video I, Dec. 10, 2011, Weed Wars: The Story of Jayden-Andrew DeAngelo; https://www.youtube.com/watch?v=2WizdR5uHj0.
Weed Wars, Video II, May 25, 2013, 3 pages; available at https://www.youtube.com/watch?v=XBX_DB9sw5U.
Nathaniel Morris (of Weed Country on Discovery Channel), Selected Media Examples of Pediatric Applications of Cannabidiol, 6 pages; available at https://www.youtube.com/watch?v=Mw3wiWkbRg8.

* cited by examiner

Chiral forms of tetrahydrocannabinol (THC)

(-)-trans-Δ⁹-THC (+)-trans-Δ⁹-THC (-)-cis-Δ⁹-THC (+)-cis-Δ⁹-THC

Autofluorescence spectra of botanically derived purified CBD (BOT) and synthetic CBD (SYN) at 100mM representative of the excitation scan from 230 nm to below the emission wavelengths fixed at 400 or 440 nm Experiment 1 - sigmoidal curve showing log dose of CBD versus anticonvulsant activity upon MES test Sigmoidal curve analysis upon MES test: CBD (SYN) and botanically derived purified CBD (BOT 0.02% THC) doses at [10, 50, 100, 150 and 200 mg/kg]; i.p.; 60 min pre-treatment time; n=10.

| Analysis | CBD (SYN) $ED_{50}$ (mg/kg) | CBD (BOT) $ED_{50}$ (mg/kg) | t-test (p value) |
|---|---|---|---|
| Sigmoidal curve - constant top | 77.60 | 70.20 | 0.0013 |

CANNABIDIOL PREPARATIONS AND ITS USES

CROSS-REFERENCE TO RELATED APPLICATIONS

This application is a continuation application of U.S. application Ser. No. 17/011,715, filed Sep. 3, 2020, which claims the benefit of International PCT Application No. PCT/GB2019/051173, filed Apr. 26, 2019; and Great Britain Application No. 1806953.4, filed Apr. 27, 2018; each of the aforementioned applications is incorporated herein by reference in its entirety.

FIELD OF THE INVENTION

Cannabidiol (CBD) is a cannabinoid designated chemically as 2-[(1R,6R)-3-Methyl-6-(1-methylethenyl)-2-cyclohexen-1-yl]-5-pentyl-1,3-benzenediol. Its empirical formula is $C_{21}H_{30}O_2$ and its molecular weight is 314.46. CBD is a cannabinoid that naturally occurs in the *Cannabis sativa* L. plant. CBD is a white to pale yellow crystalline solid which is insoluble in water and soluble in organic solvents.

The present invention encompasses the surprising recognition that certain CBD preparations which are prepared from a botanical origin are more effective in treating diseases or disorders than preparations of CBD which are synthetic or purified to the extent no other impurities in the form of other cannabinoids are present.

Prior CBD compositions have been prepared such that no psychoactive components, e.g., tetrahydrocannabinol (THC), remain in the final CBD preparation. Surprisingly, the absence of such minor impurities reduces the efficacy of CBD treatment.

Such CBD preparations are characterized by chemical components and/or functional properties that distinguish them from prior CBD compositions. One or more components of the preparations described herein provide an unexpectedly synergistic effect when utilized in combination.

BACKGROUND TO THE INVENTION

Cannabinoids are natural and synthetic compounds structurally or pharmacologically related to the constituents of the cannabis plant or to the endogenous agonists (endocannabinoids) of the cannabinoid receptors CB1 or CB2. The only way in nature in which these compounds are produced is by the cannabis plant. Cannabis is a genus of flowering plants in the family Cannabaceae, comprising the species *Cannabis sativa*, *Cannabis indica*, and *Cannabis ruderalis* (sometimes considered as part of *Cannabis sativa*).

Cannabis plants comprise a highly complex mixture of compounds. At least 568 unique molecules have been identified. Among these compounds are cannabinoids, terpenoids, sugars, fatty acids, flavonoids, other hydrocarbons, nitrogenous compounds, and amino acids.

Cannabinoids exert their physiological effects through a variety of receptors including, but not limited to, adrenergic receptors, cannabinoid receptors (CB1 and CB2), GPR55, GPR3, or GPR5. The principle cannabinoids present in cannabis plants are cannabinoid acids tetrahydrocannabinolic acid (THCA) and cannabidiolic acid (CBDA) with small amounts of their respective neutral (decarboxylated) cannabinoids. In addition, cannabis may contain lower levels of other minor cannabinoids.

Crude extracts from cannabis plants containing CBD have been used by patients suffering from diseases and disorders. However, such crude products are unsuitable for use in pharmaceutical formulations. Those seeking to prepare more consistent CBD preparations for use in treating diseases or disorders have made a concerted effort to either prepare CBD synthetically or attempt to remove all compounds other than CBD, particularly psychoactive compounds such as THC, from plant derived cannabinoids.

The present invention encompasses the surprising discovery that particular preparations comprising CBD have an improved therapeutic efficacy in comparison to synthetic preparations of CBD which comprise no minor cannabinoid impurities and crude extracts which have higher levels of the minor cannabinoid impurities.

As stated, cannabinoids are a class of compounds which may be derived naturally from the cannabis plant or produced synthetically via chemical synthesis.

More than 100 different cannabinoids produced by cannabis have been identified as described in Handbook of Cannabis, Roger Pertwee, Chapter 1, pages 3 to 15. These cannabinoids can be split into different groups as follows: phytocannabinoids; endocannabinoids and synthetic cannabinoids (which may be novel cannabinoids or synthetically produced versions of phytocannabinoids or endocannabinoids).

Phytocannabinoids are cannabinoids that originate from nature and can be found in the cannabis plant. Phytocannabinoids can be isolated from plants to produce a highly purified extract. Phytocannabinoids may be obtained as either the neutral (decarboxylated form) or the carboxylic acid form depending on the method used to extract the cannabinoids from plant material. For example, it is known that heating the carboxylic acid form will cause most of the carboxylic acid form to decarboxylate into the neutral form. Phytocannabinoids can only be produced from plants, however versions of phytocannabinoids may be produced synthetically via chemical synthesis.

Endocannabinoids are endogenous lipid-based retrograde neurotransmitters that bind to cannabinoid receptors, and cannabinoid receptor proteins that are expressed throughout the mammalian central nervous system (including the brain) and peripheral nervous system. The endocannabinoid system is involved in regulating a variety of physiological and cognitive processes including fertility, pregnancy, during pre- and postnatal development, appetite, pain-sensation, mood, and memory, and in mediating the pharmacological effects of cannabis.

Synthetic cannabinoids are compounds that have a cannabinoid-like structure and are manufactured using chemical means rather than by the plant.

Certain cannabinoids are described in more detail below.

Cannabidiol (CBD) is a major cannabinoid constituent of Cannabis species, such as the hemp plant (*Cannabis sativa*). Unlike other cannabinoids, such as THC, cannabidiol does not bind to CB1 or CB2, or its binding to the receptors is negligible in terms of inducing a pharmacological effect. Thus, cannabidiol does not cause the central or peripheral nervous system effects mediated by the CB1 or CB2 receptors. CBD has little or no psychotropic (cannabimimetic) activity and its molecular structure and properties are substantially different from those of other cannabinoids.

Cannabidiol administration has been the subject of research in an attempt to provide an alternative treatment for various diseases and disorders which may respond to such treatment.

Tetrahydrocannabinol (THC) is the principal psychoactive constituent of cannabis. THC is a partial agonist at the CB1 and CB2 receptors. Synthetic THC or dronabinol is approved for the treatment of loss of appetite in AIDS patients and nausea and vomiting caused by cancer chemotherapy. The cannabimimetic side effects caused by THC include feeling high, nausea, vomiting, anxiety, depression and weakness.

Of the over 100 natural cannabinoids identified in *Cannabis sativa*, seven have been classified as CBD-type compounds, these cannabinoids have the same absolute configuration as CBD. These are: CBD, Cannabidiolic acid (CBDA), Cannabidivarin (CBDV), Cannabidivarin acid (CBDVA), Cannabidiol-C1 (CBD-C1), Cannabidiol-C4 (CBD-C4) and Cannabidiol monomethyl ether (CBDM).

Cannabidiolic acid (CBDA) is the main form in which CBD exists in the cannabis plant. It is converted into CBD after decarboxylation.

Cannabidiol-C1 (CBD-C1) also known as cannabidiorcol is a homolog of CBD, with the side-chain shortened by four methylene bridges. CBD-C1 occurs naturally in plants producing CBD in minor quantities.

Cannabidivarin (CBDV) is a homolog of CBD, with the side-chain shortened by two methylene bridges. CBDV is a non-psychoactive cannabinoid and has been shown to have anti-convulsant activity in a mouse model of epilepsy Cannabidiol-C4 (CBD-C4) also known as nor-cannabidiol is a homolog of CBD, with the side-chain shortened by one methylene bridge. CBD-C4 occurs naturally in plants producing CBD in minor quantities.

The present invention demonstrates an increased efficacy of a botanically derived purified CBD preparation which comprises minor amounts of the cannabinoids CBD-C1, CBDV, CBD-C4 and THC over a synthetic CBD which does not comprise minor amounts of cannabinoids. These data are particularly surprising particularly given the fact that the concentration of CBD within the botanically derived purified CBD preparation and the synthetic preparation were the same. The invention further discloses the difference in the physicochemical properties of a botanically derived purified CBD and a synthetic CBD.

BRIEF SUMMARY OF THE DISCLOSURE

In accordance with a first aspect of the present invention there is provided a cannabidiol (CBD) preparation characterized in that it comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC.

In accordance with a second aspect of the present invention there is provided a cannabidiol (CBD) preparation characterized in that it comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC for use as a medicament.

In accordance with a third aspect of the present invention there is provided a cannabidiol (CBD) preparation characterized in that it comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC for use in the treatment of neurodevelopmental diseases and conditions.

In accordance with a fourth aspect of the present invention there is provided a cannabidiol (CBD) preparation characterized in that it comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC for use in the treatment of epilepsy.

In accordance with a fifth aspect of the present invention there is provided a cannabidiol (CBD) preparation characterized in that it comprises greater than or equal to 98% (w/w) CBD and less than or equal to 2% (w/w) other cannabinoids, wherein the less than or equal to 2% (w/w) other cannabinoids comprise the cannabinoids tetrahydrocannabinol (THC); cannabidiol-C1 (CBD-C1); cannabidivarin (CBDV); and cannabidiol-C4 (CBD-C4), and wherein the THC is present as a mixture of trans-THC and cis-THC for use in the treatment of schizophrenia.

Preferably the preparation comprises not more than 1.5% (w/w) THC based on total amount of cannabinoid in the preparation. More preferably the preparation comprises about 0.01% to about 0.1% (w/w) THC based on total amount of cannabinoid in the preparation. More preferably still the preparation comprises about 0.02% to about 0.05% (w/w) THC based on total amount of cannabinoid in the preparation.

In an embodiment of the invention the mixture of trans-THC and cis-THC is present at a ratio of about 3.6:1 trans-THC:cis-THC. In a further embodiment of the invention the mixture of trans-THC and cis-THC is present at a ratio of about 0.8:1 trans-THC:cis-THC.

Preferably the preparation comprises about 0.1% to about 0.15% (w/w) CBD-C1 based on total amount of cannabinoid in the preparation.

Preferably the preparation comprises about 0.2% to about 0.8% (w/w) CBDV based on total amount of cannabinoid in the preparation.

Preferably the preparation comprises about 0.3% to about 0.4% (w/w) CBD-C4 based on total amount of cannabinoid in the preparation.

In one embodiment at least a portion of at least one of the cannabinoids present in the CBD preparation is isolated from cannabis plant material.

Preferably at least a portion of the CBD present in the CBD preparation is isolated from cannabis plant material.

Preferably at least a portion of the THC present in the CBD preparation is isolated from cannabis plant material.

Preferably at least a portion of the CBD-C1 present in the CBD preparation is isolated from cannabis plant material.

Preferably at least a portion of the CBDV present in the CBD preparation is isolated from cannabis plant material.

Preferably at least a portion of the CBD-C4 present in the CBD preparation is isolated from cannabis plant material.

In a further embodiment of the invention substantially all of at least one of the cannabinoids present in the CBD preparation is isolated from cannabis plant material.

Preferably substantially all of the CBD present in the CBD preparation is isolated from cannabis plant material.

Preferably substantially all of the THC present in the CBD preparation is isolated from cannabis plant material.

Preferably substantially all of the CBD-C1 present in the CBD preparation is isolated from cannabis plant material.

Preferably all of the CBDV present in the CBD preparation is isolated from cannabis plant material.

Preferably all of the CBD-C4 present in the CBD preparation is isolated from cannabis plant material.

In a further embodiment of the invention substantially all of the cannabinoids present in the CBD preparation are isolated from cannabis plant material.

Preferably the cannabis plant material is from a *Cannabis sativa*, *Cannabis indica*, or *Cannabis ruderalis* plant.

Preferably the cannabis plant is a high-CBD containing cannabis chemotype.

In a further embodiment of the invention at least a portion of at least one of the cannabinoids present in the CBD preparation is prepared synthetically.

Preferably at least a portion of the CBD present in the CBD preparation is prepared synthetically.

Preferably at least a portion of the THC present in the CBD preparation is prepared synthetically.

Preferably at least a portion of the CBD-C1 present in the CBD preparation is prepared synthetically.

Preferably at least a portion of the CBDV present in the CBD preparation is prepared synthetically.

Preferably at least a portion of the CBD-C4 present in the CBD preparation is prepared synthetically.

In a further embodiment of the invention substantially all of at least one of the cannabinoids present in the CBD preparation is prepared synthetically.

Preferably substantially all the CBD present in the CBD preparation is prepared synthetically.

Preferably substantially all the THC present in the CBD preparation is prepared synthetically.

Preferably substantially all the CBD-C1 present in the CBD preparation is prepared synthetically.

Preferably substantially all the CBDV present in the CBD preparation is prepared synthetically.

Preferably substantially all the CBD-C4 present in the CBD preparation is prepared synthetically.

Preferably substantially all of the cannabinoids present in the CBD preparation are prepared synthetically.

In a further embodiment of the invention the neurodegenerative disease or disorder is Alzheimer's disease; Parkinson's disease; essential tremor; amyotrophic lateral sclerosis (ALS); Huntington's disease; Friedreich's ataxia; multiple sclerosis; frontotemporal dementia; prion disease; Lewy body dementia; progressive supranuclear palsy; vascular dementia; normal pressure hydrocephalus; traumatic spinal cord injury; HIV dementia; alcohol induced neurotoxicity; Down's syndrome; movement disorders of the central and/or peripheral nervous system; motor neurone diseases (MND); spinal muscular atrophy; or any other related neurological or psychiatric neurodegenerative disease; brain damage; brain injury; brain dysfunction; dysgraphia; dysarthria; apraxia; agnosia; amnesia; dizziness; vertigo; coma; stroke; spinal cord damage; spinal cord injury; spinal cord disorders; central neuropathy; peripheral neuropathy; cranial nerve disorder; trigeminal neuralgia; tumors of the nervous system; infections of the brain or spinal cord; encephalitis; meningitis; prion disease; complex regional pain syndrome; an autonomic nervous system disorder; autonomic neuropathy; dysautonomia; postural orthostatic tachycardia syndrome (POTS); neurocardiogenic syncope (NCS); multiple system atrophy (MSA); hereditary sensory and autonomic neuropathy (HSAN); Holmes-Adie syndrome (HAS); a sleep disorder; narcolepsy; pain; migraine; cluster headache; tension headache; back pain; lower back pain; neck pain; neuropathic pain; cancer pain; allodynia; arthritic pain; inflammatory pain; a neuropsychiatric disorder; attention deficit hyperactivity disorder; autism; Tourette's Syndrome; obsessive compulsive disorder; an autism spectrum disorder; Rett syndrome; Fragile X syndrome; Angelman syndrome; hyperkinetic disorder; mitochondrial disease; dystonia; a cancer; brain cancer; glioma; breast cancer; liver cancer; lung cancer; pancreatic cancer; melanoma; ovarian cancer; gastric cancer; renal cancer; bladder cancer; addiction; nicotine addiction; smoking; alcohol addiction; drug addiction; cannabis use disorder; a mental disorder; post-traumatic stress disorder; anxiety; early psychosis; schizophrenia; a cognitive disorder; stroke; cardiac ischemia; coronary artery disease; thromboembolism; myocardial infarction; ischemic related disease; a gastrointestinal disorder; inflammatory bowel disease; Crohn's disease; ulcerative colitis; nausea; vomiting; emesis; motion sickness; chemotherapy induced nausea; chemotherapy induced nausea vomiting; inflammation; arthritis; rheumatoid arthritis; osteoarthritis; diabetes; high blood pressure; poor insulin control; appetite suppression; anorexia; neonatal hypoxic-ischemic encephalopathy (NHIE); a degenerative skeletal muscle disease; or Duchenne muscular dystrophy (DMD).

In a further embodiment of the invention the epilepsy is Dravet syndrome, Lennox Gastaut syndrome, febrile infection related epilepsy syndrome (FIRES), Doose syndrome, Sturge Weber syndrome, CDKL5 mutation; Aicardi syndrome; bilateral polymicrogyria; Dup15q; SNAP25; benign rolandic epilepsy; juvenile myoclonic epilepsy; infantile spasm (West syndrome); and Landau-Kleffner syndrome, refractory epilepsy, juvenile spasms, West syndrome, infantile spasms, refractory infantile spasms, tuberous sclerosis complex (TSC); neurogenetic storage disorder, neuronal ceroid lipofuscinoses (NCL), Batten disease, brain abnormality, atonic, idiopathic, absence seizure, partial seizure, simple partial seizure, or complex partial seizure.

DEFINITIONS

Figure 1:
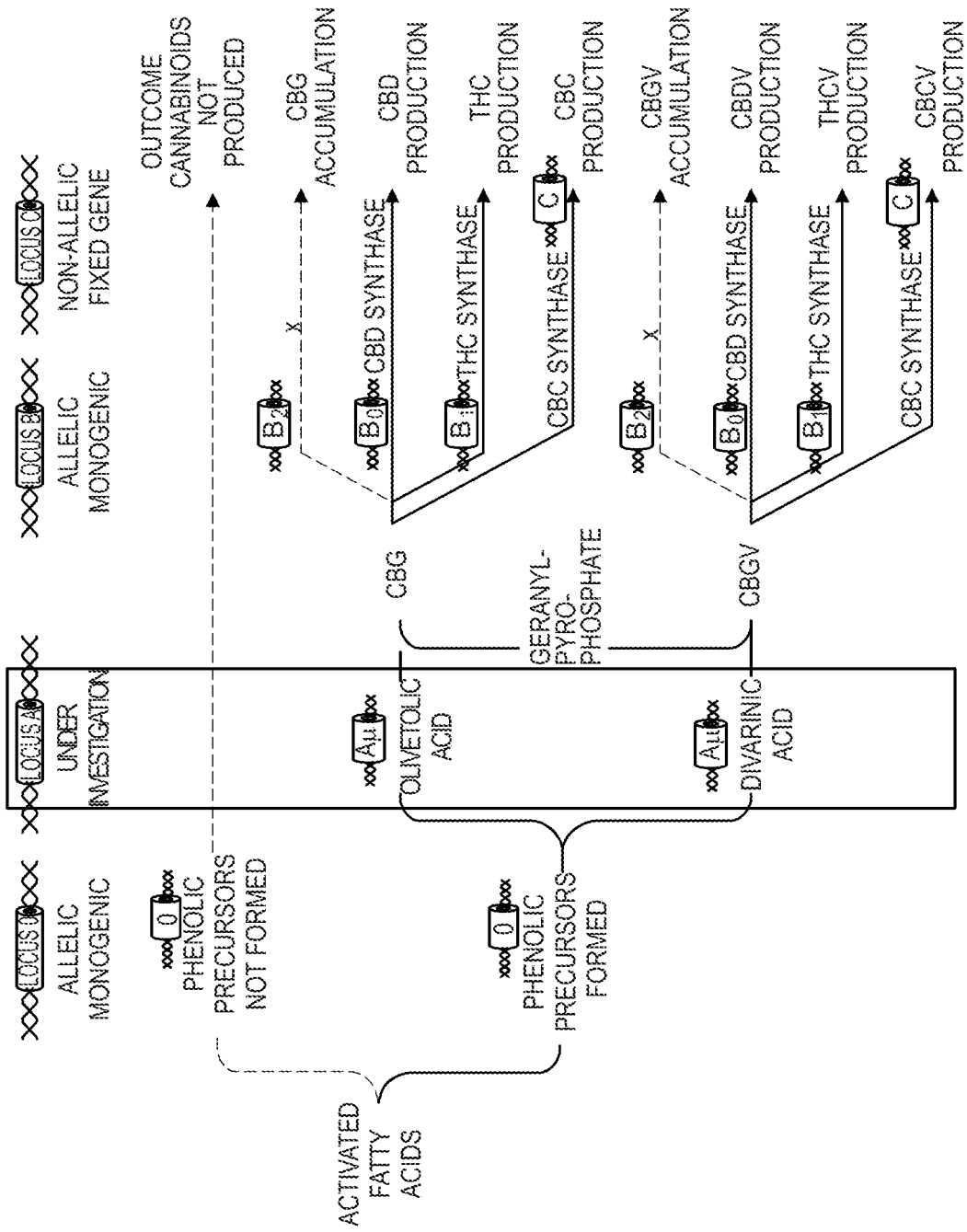
FIG. 1 depicts the biosynthetic pathway of cannabinoid production.

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

About or Approximately: The terms "about" or "approximately", as applied to one or more values of interest, refers to a value that is similar to a stated reference value. In certain embodiments, the term "about" or "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context.

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g. intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively, or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Amelioration: as used herein, refers to the prevention, reduction or palliation of a state, or improvement of the state of a subject. Amelioration includes but does not require complete recovery or complete prevention of a disease, disorder or condition (e.g., radiation injury).

Biologically active: as used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papilloma's, and the like.

Carrier: as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: Those skilled in the art will appreciate that the term "composition" may be used to refer to a discrete physical entity that comprises one or more specified components. In general, unless otherwise specified, a composition may be of any form—e.g., gas, gel, liquid, solid, etc.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Excipient: as used herein, refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Improve, increase, inhibit or reduce: As used herein, these terms, or grammatically comparable comparative terms, indicate values that are relative to a comparable reference measurement. For example, in some embodiments, an assessed value achieved with an agent of interest may be "improved" relative to that obtained with a comparable reference agent. Alternatively or additionally, in some embodiments, an assessed value achieved in a subject or system of interest may be "improved" relative to that obtained in the same subject or system under different conditions (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc.). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

In vitro: The term "in vitro" as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term may be used to refer to events that occur within a living cell (as opposed to, for example, in vitro systems).

Isolated: as used herein, refers to a substance and/or entity that has been (1) separated from at least some of the components with which it was associated when initially produced (whether in nature and/or in an experimental setting), and/or (2) designed, produced, prepared, and/or manufactured by the hand of man. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Isomer: As is known in the art, many chemical entities (in particular many organic molecules and/or many small molecules) can exist in a variety of structural (e.g., geometric/conformational) and/or optical isomeric forms. For example, any chiral center can exist in R and S configurations; double bonds can exist in Z and E conformational isomers, certain structural elements can adopt two or more tautomeric forms, etc. In some embodiments, as will be clear to those skilled in the art from context, depiction of or reference to a particular compound structure herein may represent all structural and/or optical isomers thereof. In some embodiments, as will be clear to those skilled in the art from context, depiction of or reference to a particular compound structure herein is intended to encompass only the depicted or referenced isomeric form. In some embodiments, compositions including a chemical entity that can exist in a variety of isomeric forms include a plurality of such forms; in some embodiments such compositions include only a single form. For example, in some embodiments, compositions including a chemical entity that can exist as a variety of optical isomers (e.g., stereoisomers, diastereomers, etc.) include a racemic population of such optical isomers; in some embodiments such compositions include only a single optical isomer and/or include a plurality of optical isomers that together retain optical activity. Where there exists two or more isomers within a composition they may exist as a mixture with various ratios.

Mixture: The phrase "mixture" describes a combination of two or more different compounds or agents which occur within the same composition.

Moiety: Those skilled in the art will appreciate that a "moiety" is a defined chemical group or entity with a particular structure and/or or activity, as described herein.

Oral: The phrases "oral administration" and "administered orally" as used herein have their art-understood meaning referring to administration by mouth of a compound or composition.

Parenteral: The phrases "parenteral administration" and "administered parenterally" as used herein have their art-understood meaning referring to modes of administration other than enteral and topical administration, usually by injection, and include, without limitation, intravenous, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the patient is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Predetermined: By predetermined is meant deliberately selected, for example as opposed to randomly occurring or achieved.

Prevent or prevention: as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Predominantly present: The term "predominantly present", as used herein, refers to the quantity of an entity (e.g., a specific cannabinoid or isomer thereof) in a preparation or composition. For example, a cannabinoid may be predominantly present if it is at least about 50%, about 55%, about 60%, about 65%, about 70%, about 75%, about 80%, about 85%, about 90%, about 95%, about 96%, about 97%, about 98%, about 99%, or about 100% of the total cannabinoid in the preparation or composition.

Prevention: The term "prevention", as used herein, refers to a delay of onset, and/or reduction in frequency and/or severity of one or more symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. Prevention may be considered complete when onset of a disease, disorder or condition has been delayed for a predefined period of time.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference composition may comprise one or more synthetic cannabinoids. In some embodiments a reference composition may contain different types of cannabinoids, different isomeric forms of cannabinoids, different distribution of cannabinoids, different quantities of cannabinoids, etc. as compared to a test composition. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Response: As used herein, a response to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. Response may be measured according to a wide variety of criteria, including clinical criteria and objective criteria. Techniques for assessing response include, but are not limited to, clinical examination, positron emission tomatography, chest X-ray CT scan, MRI, ultrasound, endoscopy, laparoscopy, presence or level of tumor markers in a sample obtained from a subject, cytology, and/or histology. The exact response criteria can be selected in any appropriate manner, provided that when comparing groups of cells or subjects, the groups to be compared are assessed based on the same or comparable criteria for determining response rate. One of ordinary skill in the art will be able to select appropriate criteria.

Solid form: As is known in the art, many chemical entities (in particular many organic molecules and/or many small molecules) can adopt a variety of different solid forms such as, for example, amorphous forms and/or crystalline forms (e.g., polymorphs, hydrates, solvates, etc.). In some embodiments, such entities may be utilized as a single such form (e.g., as a pure preparation of a single polymorph). In some embodiments, such entities may be utilized as a mixture of such forms.

Subject: As used herein, the term "subject" refers an organism, typically a mammal (e.g., a human, in some embodiments including prenatal human forms). In some embodiments, a subject refers to any organism (e.g., mammals such as mice, rats, rabbits, non-human primates, and humans; insects; worms; etc.) and plants to which a provided compound or composition is administered in accordance with the present disclosure e.g., for experimental, diagnostic, prophylactic, and/or therapeutic purposes. In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with and/or displays one or more symptoms of a disease, disorder, and/or condition.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Symptoms are reduced: According to the present invention, "symptoms are reduced" when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom.

Systemic: The phrases "systemic administration," "administered systemically," "peripheral administration," and "administered peripherally" as used herein have their art-understood meaning referring to administration of a compound or composition such that it enters the recipient's system.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutic regimen: A "therapeutic regimen", as that term is used herein, refers to a dosing regimen whose administration across a relevant population may be correlated with a desired or beneficial therapeutic outcome.

Therapeutically effective amount: As used herein, the term "therapeutically effective amount" means an amount of a substance (e.g., a therapeutic agent, active ingredient, preparation, composition, and/or formulation) that elicits a desired a desired effect (e.g., a desired biological, clinical, or pharmacological effect or response) when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, reduce the severity of, stabilize one or more characteristics of, and/or delay the onset of the disease, disorder, and/or condition. In some embodiments, the term refers to an amount sufficient to produce the effect in at least a significant percentage (e.g., at least about 25%, about 30%, about 40%, about 50%, about 60%, about 70%, about 80%, about 90%, about 95%, or more) of a population that is suffering from and/or susceptible to a disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. In some embodiments, treatment refers to administration of a therapy that partially or completely alleviates, ameliorates, relives, inhibits, delays onset of, reduces severity of, and/or reduces incidence of one or more symptoms, features, and/or causes of a particular disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unit dose: The expression "unit dose" as used herein refers to an amount administered as a single dose and/or in a physically discrete unit of a pharmaceutical composition.

In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

DETAILED DESCRIPTION

Cannabinoids are natural and synthetic compounds structurally or pharmacologically related to the constituents of the cannabis plant or to the endogenous agonists (endocannabinoids) of the cannabinoid receptors CB1 or CB2. The only way in nature in which these compounds are produced is by the cannabis plant. Cannabis is a genus of flowering plants in the family Cannabaceae, comprising the species *Cannabis sativa*, *Cannabis indica*, and *Cannabis ruderalis* (sometimes considered as part of *Cannabis sativa*).

Cannabis plants comprise a highly complex mixture of compounds. At least 568 unique molecules have been identified. Among these compounds are cannabinoids, terpenoids, sugars, fatty acids, flavonoids, other hydrocarbons, nitrogenous compounds, and amino acids.

Cannabinoids exert their physiological effects through a variety of receptors including, but not limited to, adrenergic receptors, cannabinoid receptors (CB1 and CB2), GPR55, GPR3, or GPR5. The principle cannabinoids present in cannabis plants are cannabinoid acids tetrahydrocannabinolic acid (THCA) and cannabidiolic acid (CBDA) with small amounts of their respective neutral (decarboxylated) cannabinoids. In addition, cannabis may contain lower levels of other minor cannabinoids. "Chemical composition, pharmacological profiling, and complete physiological effects of these medicinal plants, and more importantly the extracts from cannabis, remain to be fully understood." Lewis, M. M. et al., ACS Omega, 2, 6091-6103 (2017). FIG. 1 depicts an exemplary schematic of the biosynthetic pathways of certain phytocannabinoids.

Crude extracts from cannabis plants containing CBD have been used by patients suffering from diseases and disorders. However, such crude products are unsuitable for use in pharmaceutical formulations. Those seeking to prepare more consistent CBD preparations for use in treating diseases or disorders have made a concerted effort to either prepare CBD synthetically or attempt to remove all compounds other than CBD, particularly psychoactive compounds such as THC, from plant derived cannabinoids.

The present invention encompasses the surprising discovery that a botanically derived purified CBD preparation, comprising one or more additional cannabinoids, and suitable for pharmaceutical use, exhibits enhanced therapeutic efficacy when compared to prior CBD preparations which differ from the composition disclosed herein.

These preparations differ either by being purified to the extent that no other impurities exist or being produced synthetically thereby comprising no additional cannabinoids that would be produced by nature or further differ by being an unpurified plant extract which extract comprises some or all of the cannabinoids and non-cannabinoid compounds that are co-produced by the plant and co-extracted in the preparation of the extract. In some embodiments botanically derived purified CBD preparation of the present invention may be administered in a lower dose of CBD than a synthetic or completely pure preparation of CBD.

Cannabinoids

As stated, cannabinoids are a class of compounds which may be derived naturally from the cannabis plant or produced synthetically via chemical synthesis.

More than 100 different cannabinoids produced by cannabis have been identified. These cannabinoids can be split into different groups as follows: phytocannabinoids; endocannabinoids and synthetic cannabinoids (which may be novel cannabinoids or synthetically produced versions of phytocannabinoids or endocannabinoids).

Phytocannabinoids are cannabinoids that originate from nature and can be found in the cannabis plant. Phytocannabinoids can be isolated from plants to produce a highly purified extract. Phytocannabinoids may be obtained as either the neutral (decarboxylated form) or the carboxylic acid form depending on the method used to extract the cannabinoids from plant material. For example, it is known that heating the carboxylic acid form will cause most of the carboxylic acid form to decarboxylate into the neutral form. Phytocannabinoids can only be produced from plants, however versions of phytocannabinoids may be produced synthetically via chemical synthesis.

Endocannabinoids are endogenous lipid-based retrograde neurotransmitters that bind to cannabinoid receptors, and cannabinoid receptor proteins that are expressed throughout the mammalian central nervous system (including the brain) and peripheral nervous system. The endocannabinoid system is involved in regulating a variety of physiological and cognitive processes including fertility, pregnancy, during pre- and postnatal development, appetite, pain-sensation, mood, and memory, and in mediating the pharmacological effects of cannabis.

"Synthetic cannabinoids" are compounds that have a cannabinoid-like structure and are manufactured using chemical means rather than by the plant.

Certain cannabinoids are described in more detail below. Although little is known about these cannabinoids, CBD preparations and compositions described herein which comprise one or more of these components show surprising efficacy, particularly when compared with pure and/or synthetic CBD compositions.

Cannabidiol (CBD)

CBD is a major cannabinoid constituent of Cannabis species, such as the hemp plant (*Cannabis sativa*). Unlike other cannabinoids, such as THC, CBD does not bind CB1 or CB2, or its binding to the receptors is negligible in terms of inducing a pharmacological effect. Thus, CBD does not cause the central or peripheral nervous system effects mediated by the CB1 or CB2 receptors. CBD has little or no psychotropic (cannabimimetic) activity and its molecular structure and properties are substantially different from those of other cannabinoids.

CBD administration has been the subject of research in an attempt to provide an alternative treatment for various diseases and disorders which may respond to such treatment.

In some embodiments CBD is isolated from a cannabis plant. In some embodiments CBD is prepared synthetically. In some embodiments, CBD is present as (−)-trans-CBD.

Tetrahydrocannabinol (THC)

THC is the principal psychoactive constituent of cannabis.

Figure 2:
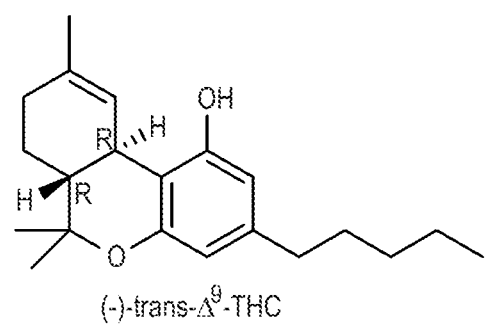
FIG. 2 depicts the different chiral forms of tetrahydrocannabinol (THC).
Figure 2:
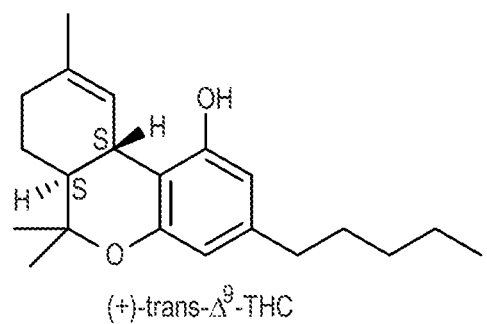
Figure 2:
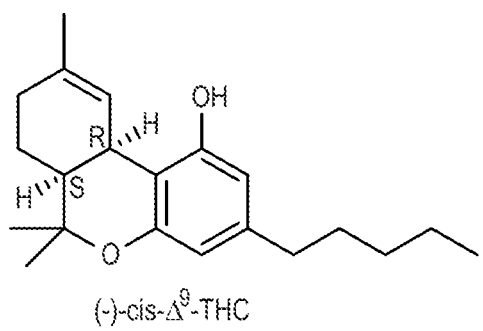
Figure 2:
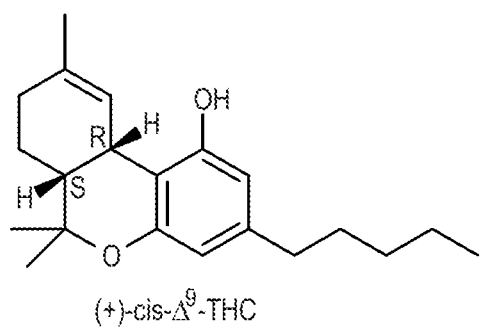

The THC molecule may exist as four distinct chiral forms as shown in FIG. 2. THC has 2 stereocenters which in turn enable the existence of 4 stereoisomers: (+)-trans-THC; (−)-trans-THC; (+)-cis-THC and (−)-cis-THC. THC commonly occurs in nature as the (−)-trans-THC isomer (Hollister, 1970)

The THC molecule mostly occurs as (−)-trans-$\Delta^9$-tetrahydrocannabinol, however the (−)-trans-$\Delta^8$-tetrahydrocannabinol homolog is also known to exist. The skilled person will appreciate that reference to the compound THC may refer to either the $\Delta^8$ or the $\Delta^9$ homolog.

In some embodiments THC is isolated from a cannabis plant. In some embodiments THC is prepared synthetically. In some embodiments, THC is present as (−)-trans-THC. In some embodiments, THC is present as (−)-cis-THC. In some embodiments, THC is present as (+)-trans-THC. In some embodiments, THC is present as (+)-cis-THC.

In some embodiments the THC is present as a mixture of isomers. In some embodiments the mixture will comprise one or more of (+)-trans-THC, (−)-trans-THC, (+)-cis-THC and (−)-cis-THC.

Cannabidivarin (CBDV)

CBDV is a homolog of CBD, with the side-chain shortened by two methylene bridges. In some embodiments CBDV is isolated from a cannabis plant. In some embodiments CBDV is prepared synthetically. In some embodiments, CBDV is present as (−)-trans-CBDV.

Cannabidiol-C1 (CBD-C1)

In some embodiments CBD-C1 is isolated from a cannabis plant. In some embodiments CBD-C1 is prepared synthetically. In some embodiments, CBD-C1 is present as (−)-trans-CBD-C1.

Cannabidiol-C4 (CBD-C4)

In some embodiments CBD-C4 is isolated from a cannabis plant. In some embodiments CBD-C4 is prepared synthetically. In some embodiments, CBD-C4 is present as (−)-trans-CBD-C4.

CBD Preparations

The present disclosure provides certain CBD preparations, characterized by chemical components and/or functional properties that distinguish them from prior CBD compositions.

In some embodiments, a CBD preparation comprises about 90%, about 91%, about 92%, about 93%, about 94%, about 95%, about 96%, about 97%, about 98%, about 99%, or more than about 99% of the other components with which they were initially associated. Preferably the CBD preparation comprises at least 98% CBD based on total amount of cannabinoid in the preparation.

In some embodiments, the CBD comprises (−)-trans-CBD isoform.

In some embodiments, the CBD preparation further comprises tetrahydrocannabinol (THC). In some embodiments, a CBD preparation comprises up to about 1%, about 2%, about 3%, about 4%, or about 5% THC based on total amount of cannabinoid in the preparation. In some embodiments, a CBD preparation comprises not more than 0.15% THC based on total amount of cannabinoid in the preparation. In some embodiments, a CBD preparation comprises about 0.01% to about 0.1% THC based on total amount of cannabinoid in the preparation. In some embodiments, a CBD preparation comprises about 0.02% to about 0.05% THC based on total amount of cannabinoid in the preparation. In some embodiments, a CBD preparation comprises at least about 0.1% THC based on total amount of cannabinoid in the preparation. In some embodiments, a CBD preparation comprises at least about 0.02% THC based on total amount of cannabinoid in the preparation. In some embodiments, the THC comprises $\Delta^9$-THC.

In some embodiments, the THC is present as a mixture of different isomers. In some embodiments, the THC comprises trans-THC and cis-THC. In some embodiments, the trans-THC and cis-THC are present at a ratio of about 5:1 (trans-THC:cis-THC). In some embodiments, the trans-THC and cis-THC are present at a ratio of about 3.5:1 (trans-THC:cis-THC). In some embodiments, the trans-THC and cis-THC are present at a ratio of about 2:1 (trans-THC:cis-THC). In some embodiments, the trans-THC and cis-THC are present at a ratio of about 1:1 (trans-THC:cis-THC). In some embodiments, the trans-THC and cis-THC are present at a ratio of about 0.8:1 (trans-THC:cis-THC).

In some embodiments the cis-THC is present as a mixture of (−)-cis-THC and (+)-cis-THC. In some embodiments, the (−)-cis-THC and (+)-cis-THC are present at a ratio of about 20:1 to 1:20 ((−)-cis-THC:(+)-cis-THC). In some embodiments, the (−)-cis-THC and (+)-cis-THC are present at a ratio of about 15:1 to 1:15 ((−)-cis-THC:(+)-cis-THC). In some embodiments, the (−)-cis-THC and (+)-cis-THC are present at a ratio of about 10:1 to 1:10 ((−)-cis-THC:(+)-cis-THC). In some embodiments, the (−)-cis-THC and (+)-cis-THC are present at a ratio of about 9:1 to 1:9 ((−)-cis-THC:(+)-cis-THC). In some embodiments, the (−)-cis-THC and (+)-cis-THC are present at a ratio of about 5:1 to 1:5 ((−)-cis-THC:(+)-cis-THC). In some embodiments, the (−)-cis-THC and (+)-cis-THC are present at a ratio of about 3:1 to 1:3 ((−)-cis-THC:(+)-cis-THC). In some embodiments, the (−)-cis-THC and (+)-cis-THC are present at a ratio of about 2:1 to 1:2 ((−)-cis-THC:(+)-cis-THC). In some embodiments, the (−)-cis-THC and (+)-cis-THC are present at a ratio of about 1:1 ((−)-cis-THC:(+)-cis-THC). In some embodiments, the (−)-cis-THC and (+)-cis-THC are present at a ratio of about 9:1 ((−)-cis-THC:(+)-cis-THC).

In some embodiments, a CBD preparation comprises one or more cannabinoids other than THC. In some embodiments, a CBD preparation comprises no more than 2% cannabinoids other than CBD based on total amount of cannabinoid in the preparation.

In some embodiments, a CBD preparation comprises cannabidivarin (CBDV). In some embodiments, the CBDV comprises the (−)-trans-CBDV isoform. In some embodiments, a CBD preparation comprises about 0.2% to about 0.8% CBDV based on total amount of cannabinoid in the preparation.

In some embodiments, a CBD preparation comprises CBD-C4 (CBD-C4). In some embodiments, the CBD-C4 comprises (−)-trans-CBD-C4 isoform. In some embodiments, a CBD preparation comprises about 0.3% to about 0.4% CBD-C4 based on total amount of cannabinoid in the preparation.

In some embodiments, a CBD preparation comprises CBD-C1 (CBD-C1). In some embodiments, the CBD-C1 comprises (−)-trans-CBD-C1 isoform. In some embodiments, a CBD preparation comprises about 0.1% to about 0.15% CBD-C1 based on total amount of cannabinoid in the preparation.

In some embodiments, at least a portion of at least one of the cannabinoids present in a CBD preparation is isolated from cannabis plant material. In some embodiments, at least a portion of the CBD present in a CBD preparation is isolated from cannabis plant material. In some embodiments, at least a portion of the THC present in a CBD preparation is isolated from cannabis plant material. In some embodiments, substantially all of at least one of the cannabinoids present in a CBD preparation is isolated from cannabis plant material. In some embodiments, substantially all the CBD present in a CBD preparation is isolated from cannabis plant material. In some embodiments, substantially all the THC present in a CBD preparation is isolated from cannabis plant material. In some embodiments, substantially all of the cannabinoids present in a CBD preparation are isolated from cannabis plant material. In some embodiments, the cannabis plant material is from a *Cannabis sativa*, *Cannabis indica*, or *Cannabis ruderalis* plant. In some embodiments, the cannabis plant is a high-CBD containing cannabis chemotype. In some embodiments, the cannabis plant is a high-CBD containing cannabis chemotype of *Cannabis sativa* L. In some embodiments, the cannabis plant material comprises about 5% to about 20% CBD based on total amount of cannabinoid in the preparation. In some embodiments, the cannabis plant material comprises about 10% to about 15% CBD based on total amount of cannabinoid in the preparation. In some embodiments, the cannabis plant material comprises trans-THC and cis-THC are present at a ratio of about 3.5:1 (trans-THC:cis-THC). In some embodiments, the cannabis plant material comprises trans-THC and cis-THC are present at a ratio of about 0.8:1 (trans-THC:cis-THC).

Methods of Making CBD Preparations

In the context of this application a "botanical drug substance" is an extract derived from cannabis plant material, which extract fulfils the definition of "botanical drug substance" provided in the Guidance for Industry Botanical Drug Products Draft Guidance, August 2000, US Department of Health and Human Services, Food and Drug Administration Center for Drug Evaluation and Research of: "A drug substance derived from one or more plants, algae, or macroscopic fungi. It is prepared from botanical raw materials by one or more of the following processes: pulverization, decoction, expression, aqueous extraction, ethanolic extraction, or other similar processes."

"Plant material" is defined as a plant or plant material (e.g. bark, wood, leaves, stems, roots, flowers, fruits, seeds, berries or parts thereof) as well as exudates, and includes material falling within the definition of "botanical raw material" in the Guidance for Industry Botanical Drug Products Draft Guidance, August 2000, US Department of Health and Human Services, Food and Drug Administration Center for Drug Evaluation and Research.

The method of the invention may be used to extract cannabinoids from a specified and defined plant material known to contain such cannabinoids. Most typically, but not necessarily, the "plant material" will be "plant material" or "botanical raw material" derived from one or more cannabis plants. Most typically, but not necessarily, the one or more cannabis plants will be a specified and defined cannabis plant bred to produce a high yield of CBD.

The term "Cannabis plant(s)" encompasses wild type *Cannabis sativa* and also variants thereof, including cannabis chemovars which naturally contain different amounts of the individual cannabinoids, *Cannabis sativa* plants which are the result of genetic crosses, self-crosses or hybrids thereof. The term "Cannabis plant material" is to be interpreted accordingly as encompassing plant material derived from one or more cannabis plants. For the avoidance of doubt, it is hereby stated that "cannabis plant material" includes dried cannabis biomass. In some embodiments, at least a portion of the cannabinoid acids in such cannabis plant material are decarboxylated.

Cannabis Plants

The present invention utilizes cannabis plants and varieties bred to have specified, predetermined cannabinoid profiles and content. In some embodiments, a cannabinoid may be CBD, THC, CBDA, CBDV, CBD-C1, or CBD-C4. In some embodiments, cannabis plants have specified, predetermined terpene profiles and content. In some embodiments, cannabis plants have specified, predetermined sesquiterpene profiles and content. In some embodiments, a cannabis plant is a *Cannabis sativa*, *Cannabis indica*, or *Cannabis ruderalis* plant.

Cannabis Cultivation

In some embodiments, cannabis plants are propagated from cuttings taken from a mother plant. In some embodiments, a mother plant originates from a single seed source. In some embodiments, a crop is produced through asexual propagation. In some embodiments, all of the plants in a crop are all female. In some embodiments, propagation using cuttings controls genotype consistency.

In some embodiments, the growing cycle is about 12 weeks. In some embodiments, through controlled growing conditions cannabis plants take about 12 weeks to reach maturity. In some embodiments, cannabis plants are irrigated throughout their growing cycle with potable quality water. In some embodiments, no synthetic herbicides or pesticides are used in the cultivation of cannabis plants. In some embodiments, stringent hygiene conditions may be utilized to reduce ingress of pests and diseases, particularly in the absence of herbicides or pesticides. In some embodiments, control of growing conditions to reduce or eliminate environmental stresses is utilized to optimize plant material yield, cannabinoid content, and/or control disease. In some embodiments, environmental stresses may include drought, insufficient light, improper timing of light cycle, and unfavourable temperatures. In addition, regular inspection of the plants during the growing cycle allows for the detection of any rogue plants and pests. Rogue male plants may arise, though weeds should be absent due to the controlled growing conditions and media. Frequent inspections and biological control methods are used to manage any pests and diseases that may occur.

In some embodiments, through strict control of growing conditions the Cannabis plants reach maturity in approximately 12 weeks. In some embodiments, in the last weeks of growth, dense resinous flowers develop. In some embodiments, by the end of approximately week 11 the cannabinoid biosynthesis has slowed markedly, and the plants are ready for harvest.

Cannabis Harvest and Processing

In some embodiments, the entire plant is cut and dried in a temperature and/or humidity controlled environment. In some embodiments, the temperature is about 21° C. In some embodiments, the humidity is about 38-45% RH.

THC and CBD are the principle bioactive constituents in the BDS. However, these constituents are present as the carboxylic acids THCA and CBDA in the BRM. The acid forms slowly decarboxylate over time during drying. The leaves and flowers are stripped from the larger stems to provide the Botanical Raw Material (BRM). Under conditions of storage the loss on drying reaches equilibrium of approximately 10%. The storage conditions for the dried BRM will be dependent on the physical status of the BRM. In some embodiments, BRM is stored protected from light. In some embodiments, BRM is stored at about 15-25° C. In some embodiments, BRM is stored at about −20° C. In some embodiments, BRM is stored at about 20° C. In some embodiments, BRM is stored at about 38-42% RH.

Summary of exemplary production of a BRM:
Harvest plants
Drying (in absence of light)
Production of Botanical Raw Material (BRM) which comprises cannabinoid acids
Milling to less than 2000 μm to reduce particle size
Decarboxylation of cannabinoid acids to their neutral form (e.g. CBDA to CBD)

An exemplary BRM specification derived from a high CBD variety is illustrated in Table A below:

TABLE A

Exemplary BRM specification

| Test | Method | Specification |
|---|---|---|
| Identification: | | |
| A | Visual | Complies |
| B | TLC | Corresponds to standard (for CBD & CBDA) |
| C | HPLC/UV | Positive for CBDA |
| Assay: | In-house | NLT 90% of assayed |
| CBDA + CBD | (HPLC/UV) | cannabinoids by peak area |
| Loss on Drying | Ph.Eur. | NMT 15% |
| Aflatoxin | UKAS method | NMT 4 ppb |
| Microbial: | Ph.Eur. | |
| TVC | | NMT$10^7$ cfu/g |
| Fungi | | NMT$10^5$ cfu/g |
| E.coli | | NMT$10^2$ cfu/g |
| Foreign Matter: | Ph.Eur. | NMT 2% |
| Residual Herbicides and Pesticides | Ph.Eur. | Complies |

Characterization of CBD Preparations

Identification by Visual:

Macroscopic characteristics allow the features of the Cannabis plant to be distinguished from potential adulterants and substitutes. It is a visual identification against a photographic standard.

Identification by TLC:

TLC uses both retention value of the substance (Rf) and characteristic spot colour to effectively identify the variety of Cannabis. Laboratory samples are prepared for TLC analysis by extracting the dried herb. An aliquot is spotted onto a TLC plate, alongside reference samples for THC and CBD. Following exposure to Fast Blue B reagent, THC and THCA present as pink spots, while CBD and CBDA are orange in colour. Neutrals can be distinguished from the acids by comparison of the Rf value to that obtained for the standards. Identity is confirmed by comparison of Rf and colour of the sample spot, to that obtained for the appropriate standard.

Identification by HPLC:

HPLC uses retention time comparison of cannabinoids to effectively identify the variety of Cannabis. The reversed phase HPLC method is specific for CBD and CBDA, and therefore may be used as an identity test. Samples of biomass are extracted and centrifuged. Detection of all analytes is accomplished at 220 nm with additional confirmation of acidic analytes at 310 nm.

Assay (CBD+CBDA):

This assay may be used to monitor the CBD and CBDA content in the plant. CBD and CBDA assay are determined using an HPLC method. The efficiency of the decarboxylation process may be determined by dividing the % content in terms of w/w of CBD by the total CBD+CBDA content.

Foreign Matter:

Foreign Matter is evaluated using the Ph.Eur. test method. Flowers, leaves and side stems are spread out in a thin layer on a clean laboratory surface. Foreign Matter is separated by hand as completely as possible and is weighed. Results are expressed as % w/w of Foreign Matter in the herbal biomass sample. Foreign Matter may comprise no more than 2% of the biomass.

Decarboxylation

THC and CBD are the principle bioactive constituents in Cannabis. However, these constituents are present as their respective carboxylic acids in Cannabis plants. In order to extract THC or CBD from cannabis plant material, it is necessary to convert the storage precursor compounds of THCA and CBDA into their more readily extractable and pharmacologically active forms. THC and CBD acids slowly decarboxylate naturally over time. The traditional way to increase rate of decarboxylation is by the application of heat. However, THCA is converted not only to THC, but also to another cannabinoid, cannabinol (CBN).

The decarboxylation procedure is generally carried out within the preparation of the starting material or botanical raw material (BRM), prior to the initiation of the extraction process.

Overview of Exemplary Extraction Process:

The BDS may be extracted from decarboxylated BRM using liquid carbon dioxide methodology. This involves continuously passing liquefied carbon dioxide through the chopped biomass, which is contained in a high-pressure vessel. The crude extract is dissolved in ethanol, cooled to a low temperature then filtered to remove precipitated constituents such as waxes. Removing ethanol and water in vacuo produces BDS containing either high concentrations of CBD or THC, depending on the biomass used.

Additional methods regarding the purification and characterization of CBD preparations are disclosed and described in EP 2 311 475, the content of which is hereby incorporated by reference in its entirety.

Compositions and Formulations

CBD preparations may be formulated based on the mode of intended administration. For example, in some embodiments, administration may be ocular, oral, parenteral, topical, etc. In some embodiments, a CBD preparation may be formulated with one or more excipients to increase stability, increase shelf-life, or increase efficacy. In some embodiments, a CBD preparation is formulated for oral administration. In some embodiments a CBD preparation comprises sesame oil. In some embodiments a CBD preparation comprises ethanol. In some, embodiments, the ethanol is ethanol anhydrous. In some embodiments, a CBD preparation comprises a flavoring. In some embodiments, the flavoring may be a sweetener. In some embodiments, the sweetener may be an artificial sweetener, e.g., saccharin, acesulfame, aspartame, neotame, or sucralose. In some embodiments, the flavoring may be an artificial flavor. In some embodiments, the artificial flavor may be, e.g., vanilla, lemon, orange, lime, grapefruit, yuzu, sudachi, apple, pear, peach, grape, blueberry, strawberry, raspberry, cherry, plum, prune, raisin, cola, guarana, neroli, pineapple, apricot, banana, melon, apricot, ume, cherry, raspberry, blackberry, tropical fruit, mango, mangosteen, pomegranate, papaya, combinations thereof, or the like.

Cannabinoid preparations disclosed herein may be formulated for administration according to methods known in the art.

Uses

Diseases, Disorders, and Conditions

CBD preparations disclosed herein are useful in providing analgesia, neuroprotection, reduce inflammation, help alleviate nausea and emesis, as well as treat epilepsy, anxiety disorders, and glaucoma. Furthermore, CBD preparations disclosed herein are useful in providing treatment or amelioration of symptoms in patients suffering from neurological dysfunction or the co-morbidities associated with such disorders. In some embodiments, CBD preparations disclosed herein are more effective in treating these disorders than prior CBD compositions. In some embodiments, a CBD preparation of the present invention may be administered in a lower dose of CBD than a synthetic CBD preparation comprising the same or similar concentrations of CBD.

Pain is a common clinical problem confronting all clinicians. Millions of people in the United States suffer from severe pain that, according to numerous recent reports, is chronically under-treated or inappropriately managed. Similarly, millions of people also suffer from severe nausea and/or frequent emesis. Moreover, all too frequently, many patients suffering from chronic, under-treated or irretraceable pain also suffer from lack of appetite, nausea and/or frequent emesis. These patients present a greater clinical challenge as they are unable to receive effective doses of oral pain medications, thereby leaving their pain unalleviated. Moreover, CBD preparations disclosed herein can reduce a patient's nausea and vomiting, independent of any pain relief achieved. Thus, the disclosed CBD preparations are particularly useful in patients experiencing nausea and vomiting secondary to un- or under-treated pain. In some embodiments, CBD preparations disclosed herein are more effective in alleviating pain than prior CBD compositions.

A notable percentage of the United States population satisfy the diagnostic criteria for alcohol use disorders ("AUDs"). The consumption of excessive amounts of alcohol results in a complex array of pharmacological effects that directly impact the ability to treat the condition. These effects directly impact the brain and include progressive neurodegeneration, impaired executive function and dependence leading to withdrawal-induced negative effects. CBD preparations disclosed herein have neuroprotective, anxiolytic and anti-convulsant effects, which may be effective in preventing additional brain damage in persons with AUDs, while simultaneously decreasing the frequency of relapses. In some embodiments, CBD preparations disclosed herein are more effective in treating these disorders than prior CBD compositions.

Chronic abusers of cannabis can develop dependence and experience withdrawal symptoms when they attempt to discontinue use of the drug. Collectively cannabis dependence and withdrawal are referred to herein as cannabis use disorders. CBD preparations disclosed herein are useful in treating cannabis use disorders. In some embodiments, CBD preparations disclosed herein are more effective in treating these disorders than prior CBD compositions.

Dystonia is a neurological movement disorder, with many known causes, and characterized by involuntary, continual muscular contractions causing twisting and repetitive movements or abnormal postures. In some embodiments, CBD preparations disclosed herein are useful to reduce the muscular contractions characteristic of this disorder. CBD preparations disclosed herein are more effective in treating these disorders than prior CBD compositions.

The etiological pathology of many diseases relates to the inflammatory processes that are regulated by an individual's immune system. Inflammation may result from (1) an otherwise appropriate immunoresponse to an outside trauma, such as brain swelling secondary to a closed head injury; (2) an overactive immunoresponse, such as an allergic reaction or dermatitis; or (3) an inappropriate auto-immunoresponse, such as certain forms of multiple sclerosis, inflammatory bowel disorders and arthritis. Regardless of the underlying cause of the inflammation, it is therapeutically desirable under these circumstances to regulate the immune system and lessen the inflammatory response. CBD preparations disclosed herein can regulate various steps in the immune response and could show some therapeutic benefit in the treatment of certain inflammatory diseases such as psoriatic arthritis. In some embodiments, CBD preparations disclosed herein are more effective in treating these disorders than prior CBD compositions.

Rheumatoid arthritis affects approximately 0.5-1% of the United States population, and autoimmune diseases in general affect more than 20 million Americans. The pain associated with rheumatoid arthritis can often be disabling. Cannabinoids have been found to be useful as an adjunct treatment for rheumatoid arthritis and joint pain secondary to other autoimmune diseases, such as inflammatory bowel disease, multiple sclerosis and systemic lupus erythematosus. In some embodiments, CBD preparations disclosed herein are more effective in treating these disorders than prior CBD compositions.

In addition to the above-discussed therapeutics benefits, cannabinoids, such as CBD and CBD prodrugs, present a variety of pharmacological benefits, including, but not limited to, anti-inflammatory, anti-convulsant, anti-psychotic, antioxidant, neuroprotective, anti-cancer and immunomodulatory effects. CBD preparations disclosed herein are more effective in treating these disorders than prior CBD compositions.

The present invention provides CBD preparations and compositions and uses for treating and/or preventing any of a variety of diseases, disorders, and/or conditions, including, but not limited to those disclosed herein. In some embodiments, the present invention provides CBD preparations and compositions and uses for treating and/or preventing diseases, disorders, or conditions associated with neurological dysfunction or neuro-differentiation. In some embodiments, diseases, disorders, or conditions associated with neurological dysfunction or neuro-differentiation are those in which neural development is defective. Such diseases, disorders or conditions are often related to the neural plasticity of the brain and can include but is not limited to seizure disorders such as epilepsy. Said seizure disorders are often associated with co-morbidities such as cognitive and psychiatric impairment which may be due to the seizures themselves or the medications used to treat the seizures. Co-morbid conditions that are known to occur in seizure disorders include but are not limited to musculoskeletal system disorders; gastrointestinal and digestive disorders; respiratory system disorders; chronic pain disorders; cerebrovascular accidents; migraine; neoplasia; arthritis/rheumatism; obesity; diabetes; infections; fractures; and allergies. Psychiatric conditions such as depression; anxiety; autism spectrum disorders; interictal dysphoric disorder; interictal behavior syndrome; and psychosis of epilepsy. Cognitive conditions such as cognitive dysfunction; language abilities; socialization; attention-deficit hyperactivity disorder; learning disability; mental retardation; and Alzheimer's disease/dementia.

In some embodiments, the disease or disorder is a seizure disorder. In some embodiments, the seizure disorder is epilepsy, Dravet syndrome, Lennox Gastaut syndrome, febrile infection related epilepsy syndrome (FIRES), Doose syndrome, Sturge Weber syndrome, CDKL5 mutation; Aicardi syndrome; bilateral polymicrogyria; Dup15q; SNAP25; benign rolandic epilepsy; juvenile myoclonic epilepsy; infantile spasm (West syndrome); and Landau-Kleffner syndrome, refractory epilepsy, juvenile spasms, West syndrome, infantile spasms, refractory infantile spasms, tuberous sclerosis complex (TSC); neurogenetic storage disorder, neuronal ceroid lipofuscinoses (NCL), Batten disease, brain abnormality, atonic, idiopathic, absence seizure, partial seizure, simple partial seizure, or complex partial seizure.

In some embodiments, the disease or disorder is a neurodegenerative disease; Alzheimer's disease; Parkinson's disease; essential tremor; amyotrophic lateral sclerosis (ALS); Huntington's disease; Friedreich's ataxia; multiple sclerosis; frontotemporal dementia; prion disease; Lewy body dementia; progressive supranuclear palsy; vascular dementia; normal pressure hydrocephalus; traumatic spinal cord injury; HIV dementia; alcohol induced neurotoxicity; Down's syndrome; movement disorders of the central and/or peripheral nervous system; motor neurone diseases (MND); spinal muscular atrophy; or any other related neurological or psychiatric neurodegenerative disease; brain damage; brain injury; brain dysfunction; dysgraphia; dysarthria; apraxia; agnosia; amnesia; dizziness; vertigo; coma; stroke; spinal cord damage; spinal cord injury; spinal cord disorders; central neuropathy; peripheral neuropathy; cranial nerve disorder; trigeminal neuralgia; tumors of the nervous system; infections of the brain or spinal cord; encephalitis; meningitis; prion disease; complex regional pain syndrome; an autonomic nervous system disorder; autonomic neuropathy; dysautonomia; postural orthostatic tachycardia syndrome (POTS); neurocardiogenic syncope (NCS); multiple system atrophy (MSA); hereditary sensory and autonomic neuropathy (HSAN); Holmes-Adie syndrome (HAS); a sleep disorder; narcolepsy; pain; migraine; cluster headache; tension headache; back pain; lower back pain; neck pain; neuropathic pain; cancer pain; allodynia; arthritic pain; inflammatory pain; a neuropsychiatric disorder; attention deficit hyperactivity disorder; autism; Tourette's Syndrome; obsessive compulsive disorder; an autism spectrum disorder; Rett syndrome; Fragile X syndrome; Angelman syndrome; hyperkinetic disorder; Tourette syndrome; dystonia; a cancer; brain cancer; glioma; breast cancer; liver cancer; lung cancer; pancreatic cancer; melanoma; ovarian cancer; gastric cancer; renal cancer; bladder cancer; addiction; nicotine addiction; smoking; alcohol addiction; drug addiction; cannabis use disorder; a mental disorder; post-traumatic stress disorder; anxiety; early psychosis; schizophrenia; a cognitive disorder; stroke; cardiac ischemia; coronary artery disease; thromboembolism; myocardial infarction; ischemic related disease; a gastrointestinal disorder; inflammatory bowel disease; Crohn's disease; ulcerative colitis; nausea; vomiting; emesis; motion sickness; chemotherapy induced nausea; chemotherapy induced nausea vomiting; inflammation; arthritis; rheumatoid arthritis; osteoarthritis; diabetes; high blood pressure; poor insulin control; appetite suppression; anorexia; neonatal hypoxic-ischemic encephalopathy (NHIE); a degenerative skeletal muscle disease; or Duchenne muscular dystrophy (DMD).

Dosing and Administration

The exact regimen for administration of the compounds described herein may depend on the needs of the individual subject being treated, the type of treatment administered, and/or the judgment of the attending medical specialist. As used herein, the terms "subject" and "patient" includes both humans and animals. In some embodiments, the subject or patient is a human adult, human adolescent, human child, or human infant. As those skilled in the art will appreciate, the dosage administered will depend upon the condition being treated, the age, health and weight of the recipient, the type of concurrent treatment, if any, and the frequency of treatment.

In some embodiments, a CBD preparation or a pharmaceutical composition comprising CBD may be administered in a therapeutically effective amount. A therapeutically effective amount may be administered according to a dosing regimen comprising one or more unit doses. Generally, a therapeutically effective amount is sufficient to achieve a benefit to the subject (e.g., prophylaxis, treating, modulating, curing, preventing and/or ameliorating a disease or disorder).

A therapeutically effective amount (and/or unit dose) of a CBD preparation or a pharmaceutical composition comprising the same for any particular patient may depend upon a variety of factors including the disease or disorder being treated; disease or disorder severity; the activity of the specific CBD preparation or a pharmaceutical composition comprising the same employed; the specific CBD preparation or a pharmaceutical composition comprising the same employed; the age; body weight; fitness; comorbid conditions (e.g., other than the diseases or disorder(s) being treated) general health; sex; and diet of the patient; personal history; genetic characteristic; lifestyle parameter; severity of cardiac defect and/or level of risk of cardiac defect; the time of administration; route of administration; concomitant treatments or medications; and/or rate of excretion or metabolism of the specific CBD preparation or a pharmaceutical composition comprising the same employed; the duration of the treatment; combinations thereof; as well as other factors well known in the medical arts. In view of the present disclosure, one of ordinary skill in the art will be readily able to determine appropriate dosages depending on these and other related factors. In addition, both objective and subjective assays may optionally be employed to identify optimal dosage ranges. In some particular embodiments, appropriate doses or amounts to be administered may be extrapolated in view of the instant disclosure from dose-response curves derived from in vitro or animal model test systems.

The present invention contemplates dosing regiments comprising single as well as multiple administrations of a CBD preparation or a pharmaceutical composition comprising the same described herein. A CBD preparation or a pharmaceutical composition comprising the same can be administered at regular intervals, depending on the nature, severity and extent of the subject's condition. In some embodiments, a CBD preparation or a pharmaceutical composition comprising the same may be administered periodically at regular intervals (e.g., once every year, once every six months, once every five months, once every three months, bimonthly (once every two months), monthly (once every month), biweekly (once every two weeks), weekly, daily, multiple times each day, or continuously).

A therapeutically effective amount may be administered according to a dosing regimen that may comprise multiple unit doses. For any particular CBD preparation or a pharmaceutical composition comprising the same, a therapeutically effective amount (and/or an appropriate unit dose within an effective dosing regimen) may vary, for example, depending on route of administration, on combination with other pharmaceutical agents.

In some embodiments, a CBD preparation or a pharmaceutical composition comprising the same described herein may be administered as a single dose. In some embodiments, a CBD preparation or a pharmaceutical composition comprising the same described herein may be administered at regular intervals. Administration at an "interval," as used herein, indicates that the therapeutically effective amount is administered periodically (as distinguished from a one-time dose). The interval can be determined by standard clinical techniques. In some embodiments, a CBD preparation or a pharmaceutical composition comprising the same described herein may be administered bimonthly, monthly, twice monthly, triweekly, biweekly, weekly, twice weekly, thrice weekly, daily, twice daily, every six hours, every four hours, every two hours, or hourly. The administration interval for a given individual need not be a fixed interval, but may be varied over time, depending on the needs of the individual.

In some embodiments, a CBD preparation or a pharmaceutical composition comprising the same described herein is administered at regular intervals indefinitely. In some embodiments, a CBD preparation or a pharmaceutical composition comprising the same described herein is administered at regular intervals for a defined period.

It is to be further understood that for any particular subject, specific dosage regimens should be adjusted over time according to the individual need and the professional judgment of the person administering or supervising the administration of the enzyme replacement therapy and that dosage ranges set forth herein are exemplary only and are not intended to limit the scope or practice of the claimed invention.

In some embodiments, a CBD preparation or a pharmaceutical composition comprising the same is administered as one or more doses to provide about 0.1 mg/kg/day of CBD. In some embodiments, a CBD preparation or a pharmaceutical composition comprising the same is administered as one or more doses to provide about 0.5 mg/kg/day of CBD. In some embodiments, a CBD preparation or a pharmaceutical composition comprising the same is administered as one or more doses to provide about 1 mg/kg/day of CBD. In some embodiments, a CBD preparation or a pharmaceutical composition comprising the same is administered as one or more doses to provide about 5 mg/kg/day of CBD, e.g., for a 15 kg patient, 75 mg of CBD per day would be provided. In some embodiments, a CBD preparation or a pharmaceutical composition comprising the same is administered as one or more doses to provide about 10 mg/kg/day of CBD. In some embodiments, a CBD preparation or a pharmaceutical composition comprising the same is administered as one or more doses to provide about 20 mg/kg/day of CBD. In some embodiments, a CBD preparation or a pharmaceutical composition comprising the same is administered as one or more doses to provide about 25 mg/kg/day of CBD. In some embodiments, a CBD preparation or a pharmaceutical composition comprising the same is administered as one or more doses to provide about 50 mg/kg/day of CBD. In some embodiments, a CBD preparation or a pharmaceutical composition comprising the same is administered as one or more doses to provide about 100 mg/kg/day of CBD.

In some embodiments, a CBD preparation or a pharmaceutical composition comprising the same is administered in a dose of about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 300 mg, about 400 mg, about 500 mg, about 1000 mg, about 1500 mg, or about 2000 mg of CBD.

In some embodiments a CBD preparation or a pharmaceutical composition comprising the same may be administered as an adjunct to conventional therapy for a disease or disorder.

Kits

Some embodiments provide for a kit comprising a CBD preparation or a pharmaceutical composition comprising the same and instructions for use. In some embodiments a kit further comprises a device (e.g., spray, syringe, vaporizer, inhaler, patch, etc.) for administration of said CBD preparation or pharmaceutical composition comprising the same.

EXAMPLES

Data Demonstrating Physicochemical Properties of Botanically Derived Purified CBD Example 1: Exemplary Process for Production of a Botanically Derived Purified CBD Preparation Overview of the Process The following describes the production of the botanically derived purified CBD (>98% w/w) which has a known and constant composition which was used in the Examples below.

Plant material harvested from the *Cannabis sativa* L. plant was subjected to liquid carbon dioxide extraction, to produce a botanical extract containing CBD in addition to other cannabinoids and non-cannabinoid components. The extract was then further purified by a solvent crystallization method to yield botanically derived purified CBD. The crystallization process specifically removed other cannabinoids and plant components to yield greater than 98% (w/w) CBD.

Both the botanical starting material and the botanical extract may be controlled by specifications. An exemplary botanical starting material specification for decarboxylated cannabis plant material is described in Table 1.1 below. In some embodiments, the isomeric content for each cannabinoid may also be specified.

TABLE 1.1

Exemplary Botanical Starting Material Specification

| Decarboxylated BRM | % w/w | | | | |
|---|---|---|---|---|---|
| | CBD | THC | CBD-C1 | CBDV | CBD-C4 |
| MEAN | 11.96 | 0.46 | 0.03 | 0.14 | 0.05 |
| MIN | 6.90 | 0.27 | 0.01 | 0.08 | 0.03 |
| MAX | 16.93 | 0.65 | 0.04 | 0.20 | 0.07 |
| SD | 2.30 | | | | |
| % RSD | 19.20 | | | | |
| MEAN −3SD | 5.07 | | | | |
| MEAN +3SD | 18.85 | | | | |
| MEDIAN | 12.00 | | | | |
| COUNT | 693 | | | | |
| approximate ratio of CBD to other cannabinoid | | 26 | 475 | 85 | 230 |

An exemplary CBD preparation of botanically derived purified CBD is described in Table 1.2 below. In some embodiments, the isomeric content for each cannabinoid may also be specified.

TABLE 1.2

Specification of an exemplary botanically derived purified CBD preparation

| Test | Test Method | Limits |
|---|---|---|
| Appearance | Visual | Off-white/pale yellow crystals |
| Identification A | HPLC-UV | Retention time of major peak corresponds to certified CBD Reference Standard |
| Identification B | GC-FID/MS | Retention time and mass spectrum of major peak corresponds to certified CBD Reference Standard |
| Identification C | FT-IR | Conforms to reference spectrum for certified CBD Reference Standard |
| Identification D | Melting Point | 65-67° C. |
| Identification E | Specific Optical Rotation | Conforms with certified CBD Reference Standard; −110° to 140° (in 95% ethanol) |
| Total Purity | Calculation | ≥98.0% |
| Chromatographic Purity 1 | HPLC-UV | ≥98.0% |
| Chromatographic Purity 2 | GC-FID/MS | ≥98.0% |
| CBDA | HPLC-UV | NMT 0.15% w/w |
| CBDV | | NMT 1.0% w/w |
| $\Delta^9$ THC- | | NMT 0.1% w/w |
| CBD-C4 | | NMT 0.5% w/w |
| Residual Solvents: | | |
| Alkane- | GC | NMT 0.5% w/w |
| Ethanol | | NMT 0.5% w/w |
| Residual Water | Karl Fischer | NMT 1.0% w/w | i.NMT-Not more than

The purity of the botanically derived purified CBD preparation was greater than or equal to 98%. The botanically derived purified CBD includes THC and other cannabinoids, e.g., CBDA, CBDV, CBD-C1, and CBD-C4.

Distinct chemotypes of the *Cannabis sativa* L. plant have been produced to maximize the output of the specific chemical constituents, the cannabinoids. Certain chemovars produce predominantly CBD. Only the (−)-trans isomer of CBD is believed to occur naturally. During purification, the stereochemistry of CBD is not affected.

Production of CBD Botanical Drug Substance

An overview of the steps to produce a botanical extract, the intermediate, are as follows:
  a. Growing
  b. Direct drying
  c. Decarboxylation
  d. Extraction—using liquid $CO_2$
  e. Winterization using ethanol
  f. Filtration
  g. Evaporation High CBD chemovars were grown, harvested, dried, baled and stored in a dry room until required. The botanical raw material (BRM) was finely chopped using an Apex mill fitted with a 1 mm screen. The milled BRM was stored in a freezer prior to extraction.

Decarboxylation of CBDA to CBD was carried out using heat. BRM was decarboxylated at 115° C. for 60 minutes.

Extraction was performed using liquid $CO_2$ to produce botanical drug substance (BDS), which was then crystalized to produce the test material. The crude CBD BDS was winterized to refine the extract under standard conditions (2 volumes of ethanol at −20° C. for approximately 50 hours). The precipitated waxes were removed by filtration and the solvent was removed to yield the BDS.

Production of Botanically Derived Purified CBD Preparation

The manufacturing steps to produce the botanically derived purified CBD preparation from BDS were as follows:
  a. Crystallization using $C_5$-$C_{12}$ straight chain or branched alkane
  b. Filtration
  c. Vacuum drying The BDS produced using the methodology above was dispersed in $C_5$-$C_{12}$ straight chain or branched alkane. The mixture was manually agitated to break up any lumps and the sealed container then placed in a freezer for approximately 48 hours. The crystals were isolated via vacuum filtration, washed with aliquots of cold $C_5$-$C_{12}$ straight chain or branched alkane, and dried under a vacuum of <10 mb at a temperature of 60° C. until dry. The botanically derived purified CBD preparation was stored in a freezer at −20° C. in a pharmaceutical grade stainless steel container, with FDA food grade approved silicone seal and clamps.

Example 2: Quantification of the Stereochemistry of the THC Present in Botanically Derived Purified CBD Preparations As described in Example 1 above, the cannabinoid THC is present in the botanically derived purified CBD preparation at an amount of not more than 0.1% (w/w). In certain embodiments the THC is present at an amount of 0.02 to 0.1% w/w.

The THC molecule may exist as four distinct chiral forms as shown in FIG. 2. THC has 2 stereocenters which in turn enable the existence of 4 stereoisomers: (+)-trans-THC; (−)-trans-THC; (+)-cis-THC and (−)-cis-THC. However, THC is known to be produced in nature as the (−)-trans-THC isoform (Hollister, 1970).

The following examples describe studies undertaken to elucidate the stereoisomers which are produced by the high-CBD plant used to prepare the exemplary botanically derived purified CBD preparation which is described in Example 1.

Detection and Quantification of Trace Levels of THC in Botanically Derived Purified CBD Ultra Performance Liquid Chromatography (UPLC) was used to identify the principal cannabinoid and trace levels of other cannabinoids. The presence of the cannabinoids was confirmed by chromatographic comparison of the sample with the standard.

A core shell silica column with adjusted pH was used in a UPLC System fitted with a Photo Diode Array or Tuneable UV detector and QDa mass detector.

Figure 3:
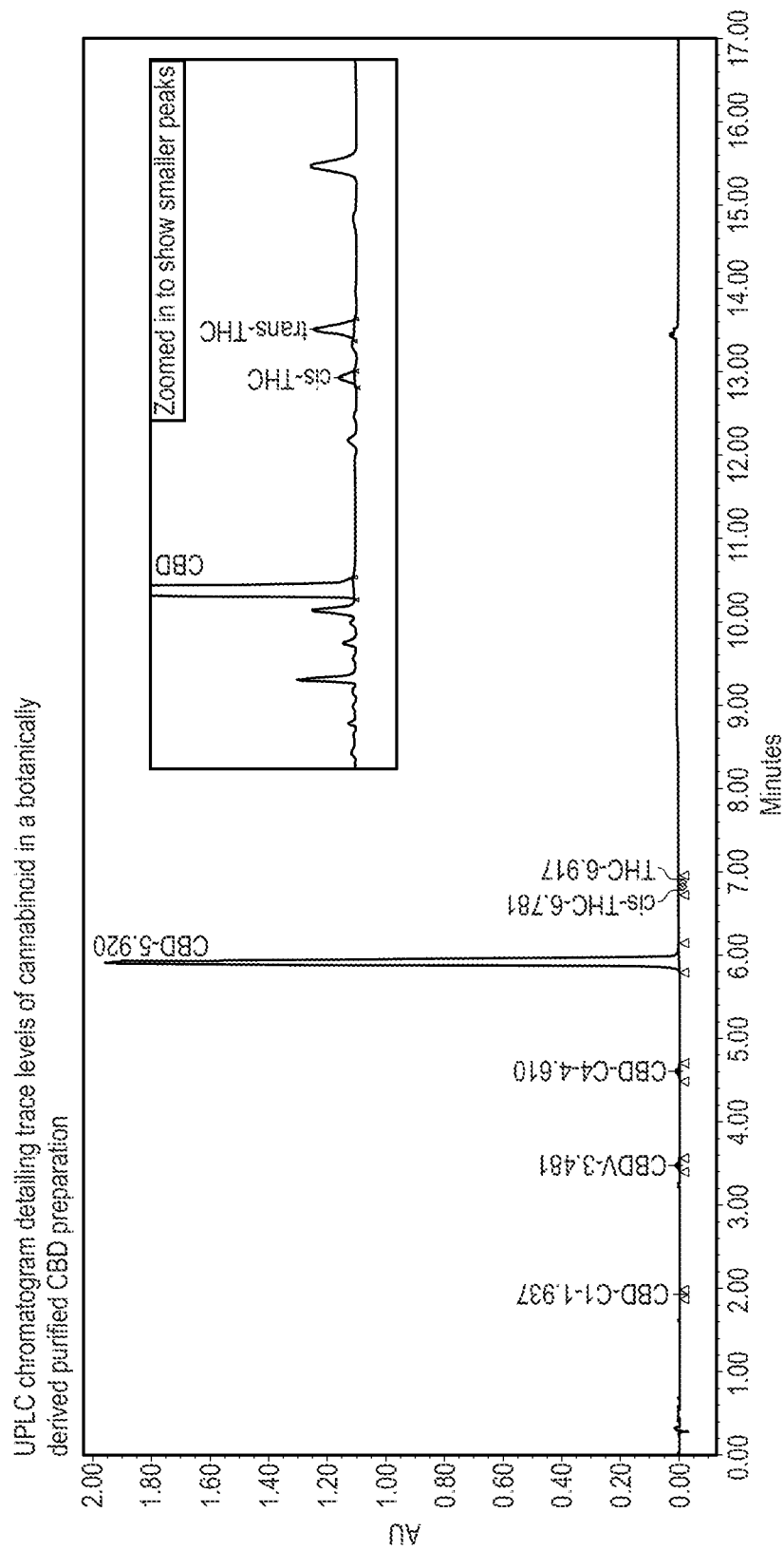
FIG. 3 depicts a UPLC chromatogram detailing trace levels of cannabinoid in a botanically derived purified CBD preparation.

FIG. 3 demonstrates an exemplary chromatogram produced using the UPLC method to detect trace quantities of cannabinoids in the botanically derived purified CBD preparation of the present invention.

As can be seen in FIG. 3 there are peaks which correspond to the following cannabinoids: CBD-C1 at a relative retention time (RTT) of 1.937 minutes; CBDV at an RTT of 3.481 minutes; CBD-C4 at an RTT of 4.610 minutes; CBD at an RTT of 5.920 minutes; (±)-cis-THC at an RTT of 6.781 minutes and (±)-trans-THC at an RTT of 6.917 minutes.

The concentration of the compounds present in the sample can be determined as w/w using the following calculation:

$$\text{Concentration (\% w/w)} = \frac{\text{Peak area} \times \text{concentration in standard (mg/ml)} \times \text{dilution factor}}{\text{Area in standard} \times \text{sample weight (mg)}}$$

The presence of cis-THC in the exemplary botanically derived purified CBD preparation was surprising as it is known that THC produced by the THC plant is in the form of (−)-trans-THC. As such the structure elucidation of the cis-THC was undertaken.

Structure Elucidation of Cis-THC

The presence, isolation and identification of cis-THC was determined from the botanical raw material produced from a high-CBD plant and in consequence the resulting botanically derived purified CBD preparation as described in Example 1 was required.

The cis-THC was successfully isolated and purified from cannabidiol (CBD) botanical drug substance (BDS) using flash chromatography and preparative-LCMS. The isolated material underwent extensive testing, including chromatographic and spectral techniques, alongside a synthetic cis-THC standard to identify the compound. It was also compared to its configurational isomer; trans-THC.

The identity of cis-THC was confirmed by four spectral techniques and three chromatographic techniques. The spectra of the botanically isolated material compared to the synthetic sample which confirmed the structure to be cis-THC.

The identity of botanically derived cis-THC was confirmed by the following techniques:

Determination of physical data and interpretation of molecular spectroscopy results; including: 1H-NMR, COSY-NMR, mass spectrometry and Quadrupole Time of Flight.

Comparing physical and spectral data of synthetically produced cis-THC to that of the botanically isolated material. This was further confirmed by comparison to the previously proposed structure of cis-THC from the literature.

Figure 4:
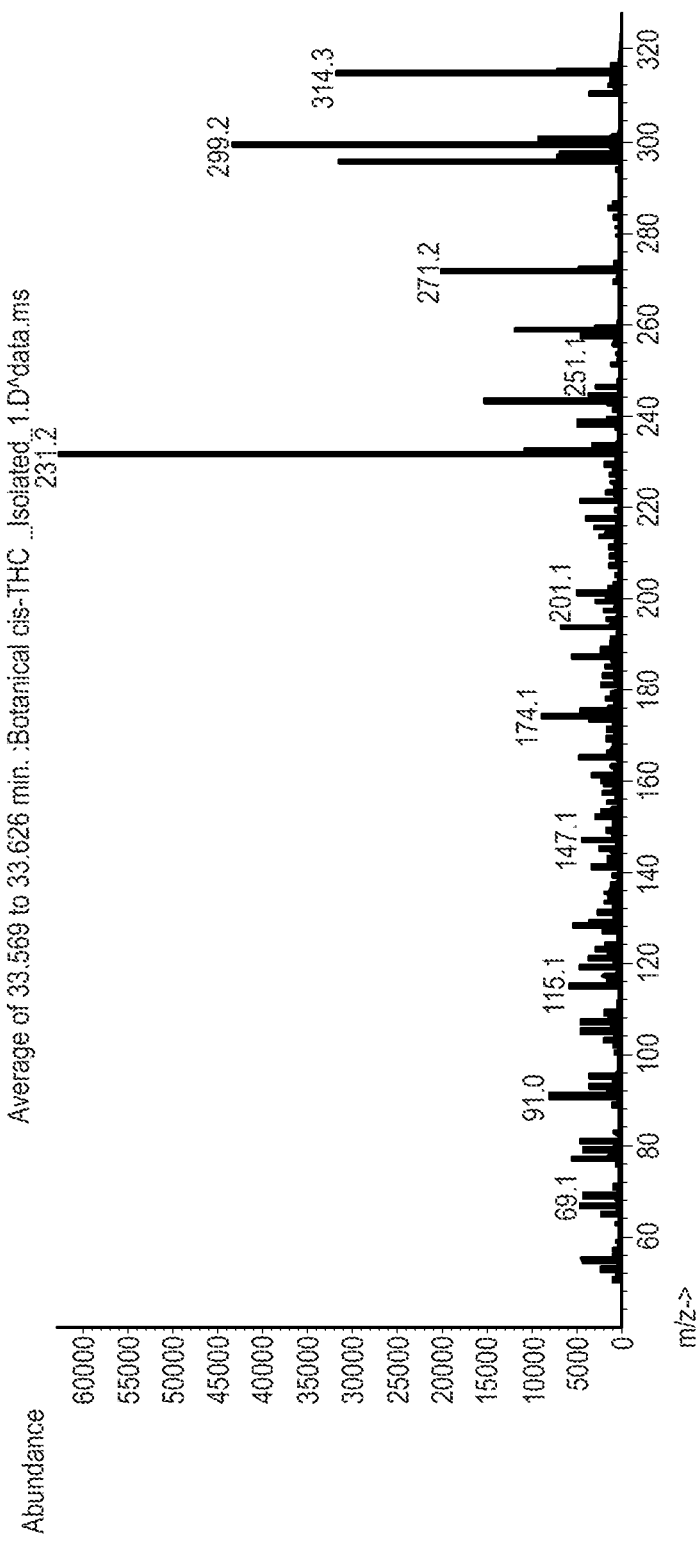
FIG. 4 depicts a mass spectrum of cis-THC isolated from a high-CBD plant.

FIG. 4 details a trace produced using the mass spectrometer which confirms the presence of cis-THC which had been isolated from high-CBD plant material.

Example 3: Quantification of the Ratio of Trans-THC to Cis-THC Present in Botanically Derived Purified CBD Preparations As is described in Example 1, the production of a botanically derived purified CBD preparation is a complex process containing several steps resulting in different types of intermediate materials. Firstly, the high-CBD plants are harvested, dried and baled to produce Botanical Raw Material, (BRM). The baled material is pelleted, extracted using liquid $CO_2$, refined during the winterization process and purified during the crystallization process. The CBD BRM starting material contains a number of different cannabinoid impurities present alongside the principal compound CBD.

The present example sought to determine the ratio of trans-THC to cis-THC throughout the production process of the botanically derived purified CBD preparation.

Figure 5:
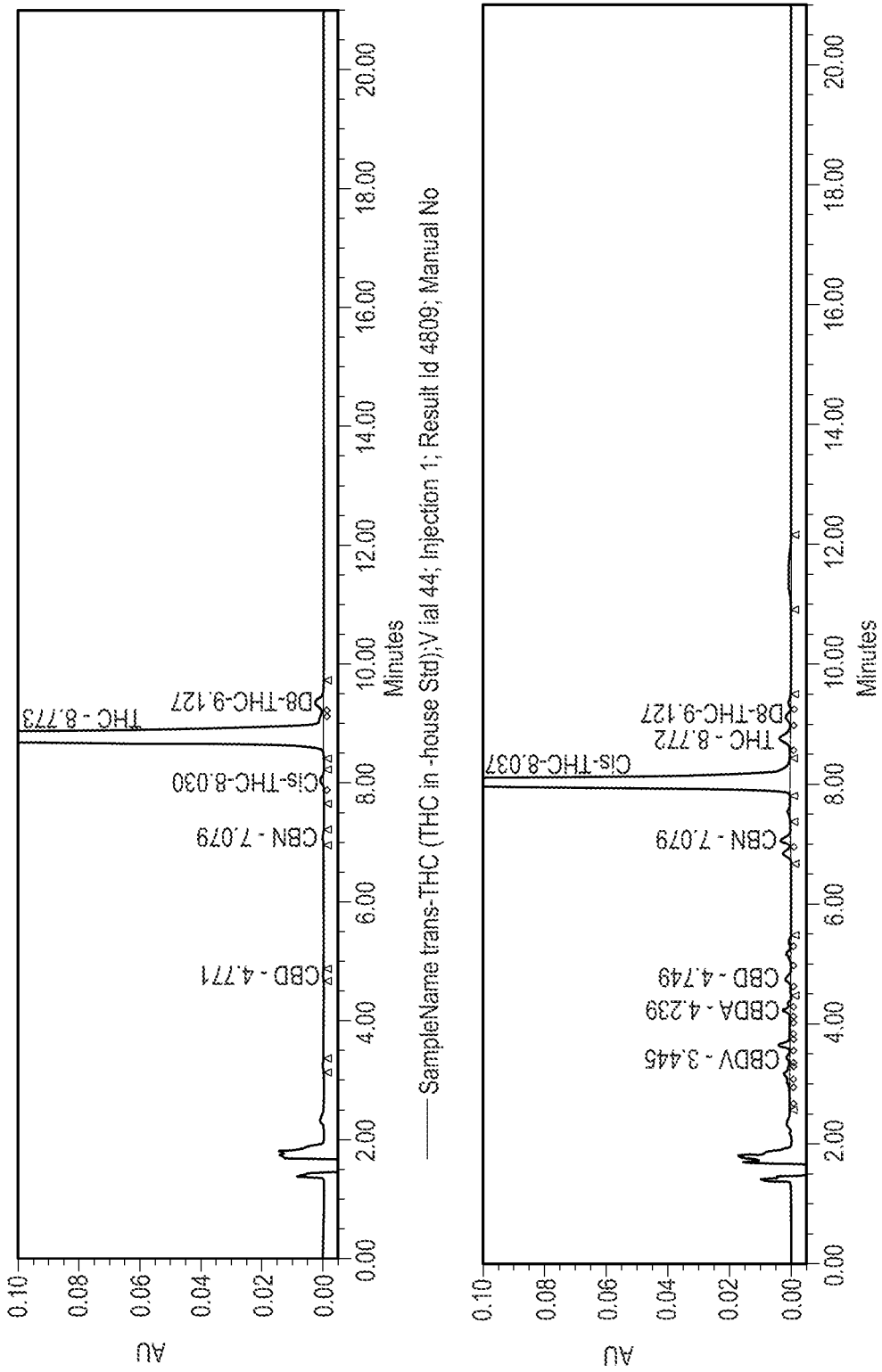
FIG. 5 depicts HPLC/DAD traces showing the retention time of trans-THC (top) and cis-THC (bottom).

The retention time of trans-THC and cis-THC is different using reverse phase chromatography as shown in FIG. 5. The polarity of these two compounds is slightly different which results in close eluting peaks in an isocratic method with baseline resolution.

The ratio of trans-THC to cis-THC was determined in samples obtained from material in different phases of the process used to produce the botanically derived purified CBD preparation described in Example 1.

The ratio of trans-THC to cis-THC changed throughout the process from the decarboxylated CBD to the botanically derived purified CBD preparation as is described in Table 3.1 below.

TABLE 3.1

Ratio of trans-THC to cis-THC in CBD material during processing stages

| CBD Sample | Median ratio (trans-THC:cis-THC) | 1st Quartile (trans-THC:cis-THC) | 3rd Quartile (trans-THC:cis-THC) |
| --- | --- | --- | --- |
| Decarboxylated CBD | 3.6:1 | 3.1:1 | 3.8:1 |
| $CO_2$ extracted CBD | 3.3:1 | 3.0:1 | 3.6:1 |
| Winterized CBD | 3.2:1 | 3.0:1 | 3.6:1 |
| Botanically derived purified CBD | 0.8:1 | 0.7:1 | 1.0:1 |

As can be seen in Table 3.1 above the ratio of trans-THC to cis-THC changes throughout the processing of the botanically derived purified CBD preparation. The botanical raw material once decarboxylated has a median ratio of 3.6:1 (trans-THC:cis-THC), this ratio becomes smaller as the material is processed with the material extracted with liquid carbon dioxide having a median ratio of 3.3:1 (trans-THC:cis-THC) and the material that had been refined by the winterization process having a median ratio of 3.2:1 (trans-THC:cis-THC). Finally, the further purification step of crystallization of the CBD material using a $C_5$-$C_{12}$ straight chain or branched alkane produces a median ratio of 0.8:1 (trans-THC:cis-THC).

Figure 6:
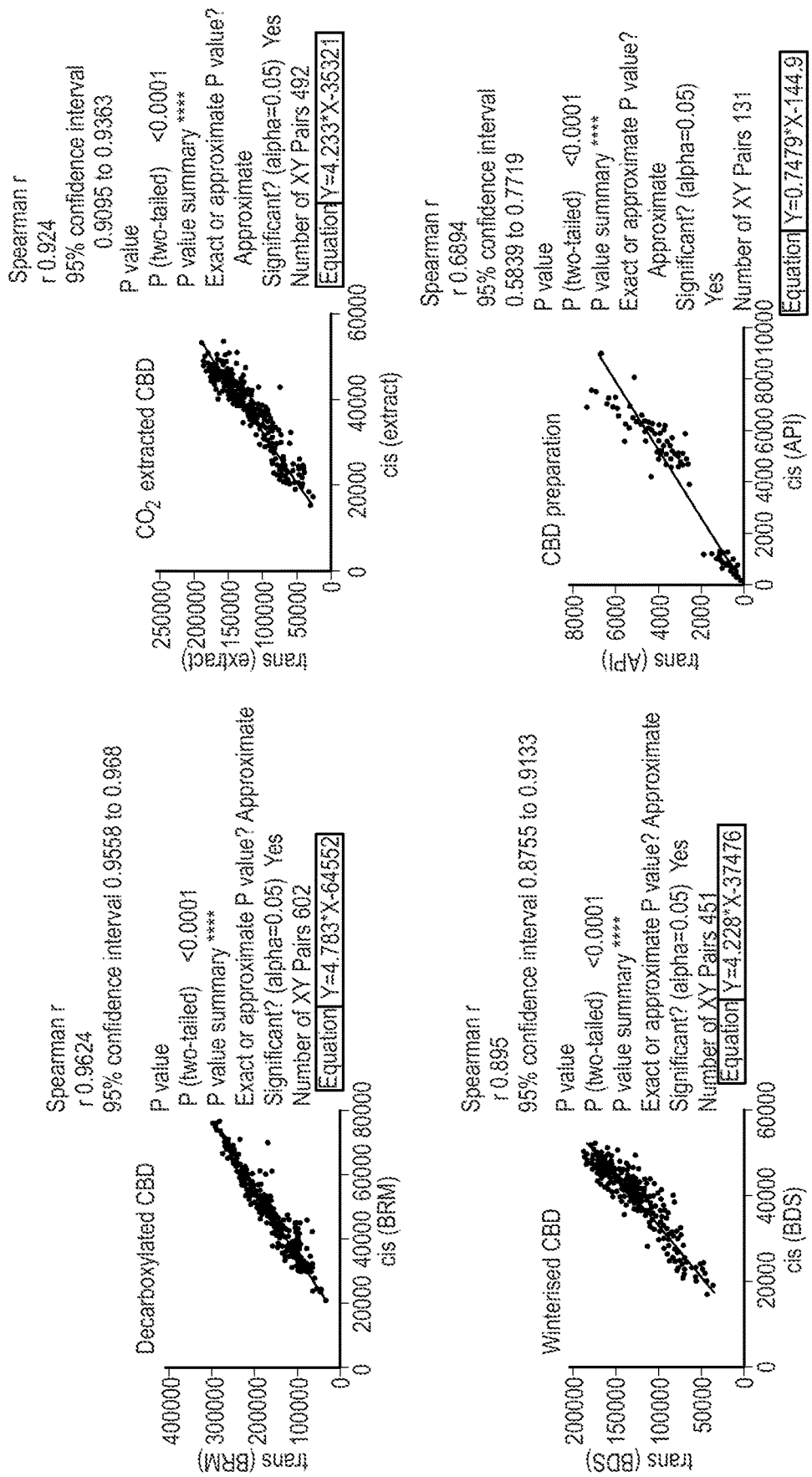
FIG. 6 depicts Spearman rank plots of trans-THC to cis-THC in CBD material during processing stages.

The ratio of trans-THC to cis-THC at the different processing stages were also plotted using a Spearman rank correlation curve, these are detailed in FIG. 6. The fit of the line demonstrates a change in ratio during the processing and has a very high confidence level. Such a correlation demonstrates control over the processing stages of the preparation of the botanically derived purified CBD where retention of the cis-THC isomer is favored over the trans-THC.

As can be seen the botanically derived purified CBD preparation comprises both trans-THC and cis-THC. The ratio of the two isomers in the highly purified final preparation is 0.8:1 (trans-THC:cis-THC).

Example 4: Quantification of the Ratio of Trans-THC to Cis-THC Present in Crude CBD Preparations In order to determine whether both trans-THC and cis-THC existed in crude CBD preparations and also if both were present what the ratio of these were, a further study was undertaken using CBD oil purchased from CBD-oil vendors.

Eight different crude CBD oil preparations were tested and all were found to comprise a mixture of trans-THC and cis-THC. Table 4.1 below details the ratios that were found in these oils.

TABLE 4.1

Ratio of trans-THC to cis-THC in crude CBD material

| Sample number | Mean ratio (trans-THC:cis-THC) |
| --- | --- |
| 1 | 4.4:1 |
| 2 | 2.7:1 |
| 3 | 2.5:1 |
| 4 | 3.2:1 |
| 5 | 2.7:1 |
| 6 | 2.3:1 |
| 7 | 3.6:1 |
| 8 | 2.7:1 |

As Table 4.1 demonstrates the ratio of trans-THC to cis-THC varies within the different crude CBD oil preparations obtained from 2.3:1 to 4.4:1 (trans-THC:cis-THC). These ratios are far removed from the botanically derived purified CBD material defined in the present invention.

Example 5: Quantification of the Stereoisomeric Form of Cis-THC Present in Botanically Derived Purified CBD Preparation Example 3 demonstrates that botanically derived purified CBD preparations comprise both trans-THC and cis-THC at a median ratio of 0.8:1 (trans-THC and cis-THC). As described in Example 2 and FIG. 2, the THC molecule has 2 stereocenters which enable the existence of four stereoisomers: (+)-trans-THC; (−)-trans-THC; (+)-cis-THC and (−)-cis-THC. The present example sought to determine whether the cis-THC was present as the (+)-cis-THC isomer, the (−)-cis-THC isomer or a mixture of the two.

A chiral method employing the principals of normal phase chromatography was developed which could successfully separate (+)-cis-THC and (−)-cis-THC.

An amylose carbamate chiral column was used with a mobile phase employing isocratic heptane with an ethanol modifier.

Figure 7:
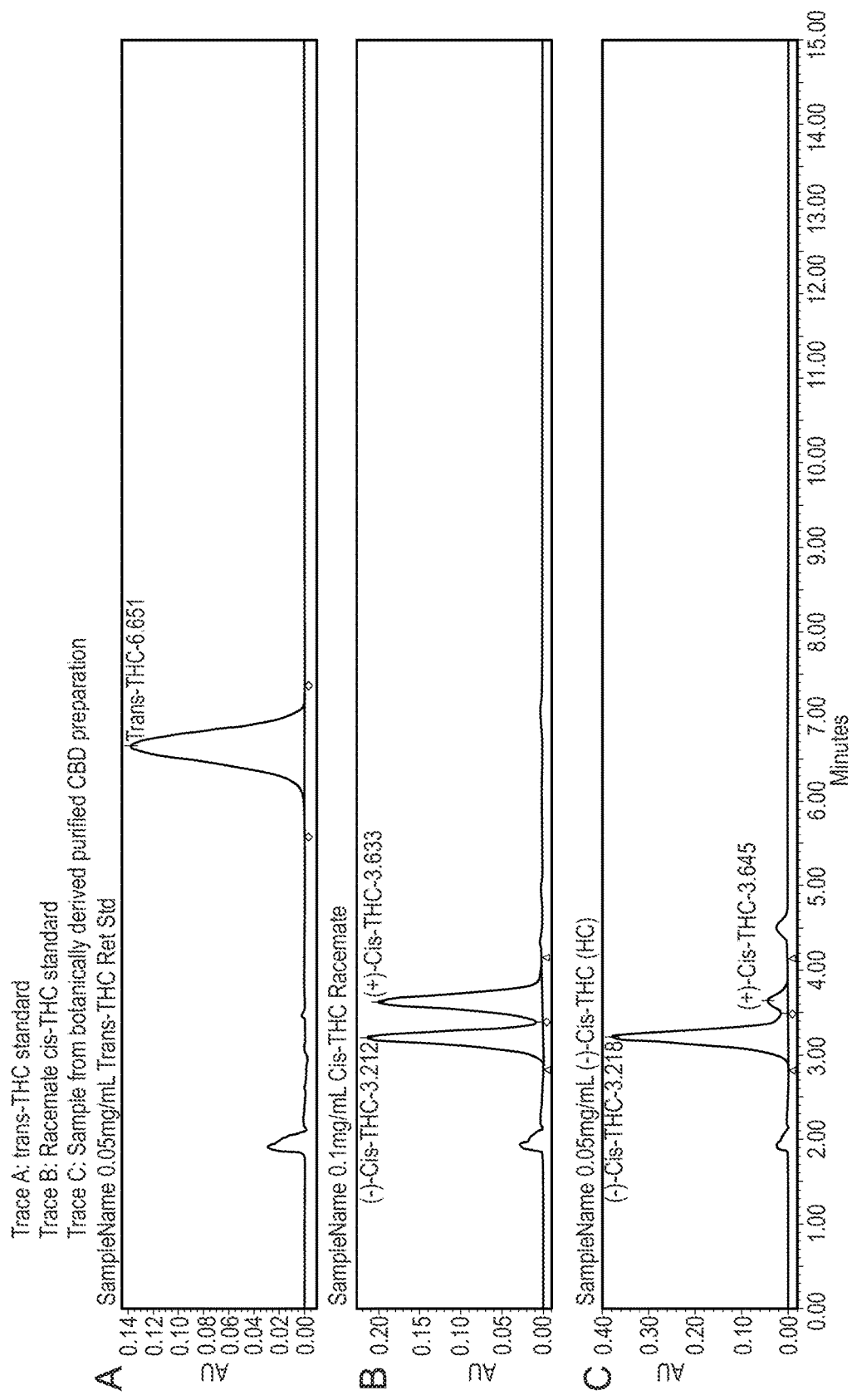
FIG. 7 depicts the determination of stereoisomeric form of cis-THC present in botanically derived purified CBD preparation.

A cis-THC sample (98.2% pure by HPLC) was isolated from botanically derived purified CBD and run on the chiral method, for the chirality to be assessed. The resulting trace is shown in FIG. 7. As can be seen in Trace C there are peaks present for both (−)-cis-THC and (+)-cis-THC indicating that the cis-THC present in botanically derived purified CBD preparations is present as a mixture of both isomers.

The approximate ratio of the (−)-cis-THC to (+)-cis-THC present was calculated to be 9:1, as determined by area under the curve. It is likely that various ranges of ratios of (−)-cis-THC to (+)-cis-THC will exist depending on the source and processing of the CBD material.

Example 6: Quantification of Composition of Synthetically Produced CBD

Two different samples of synthetically produced CBD were obtained and run on an HPLC to compare the composition of CBD of synthetic origin with that of botanically derived purified CBD. Both preparations comprised greater than or equal to 98% (w/w) CBD.

Figure 8:
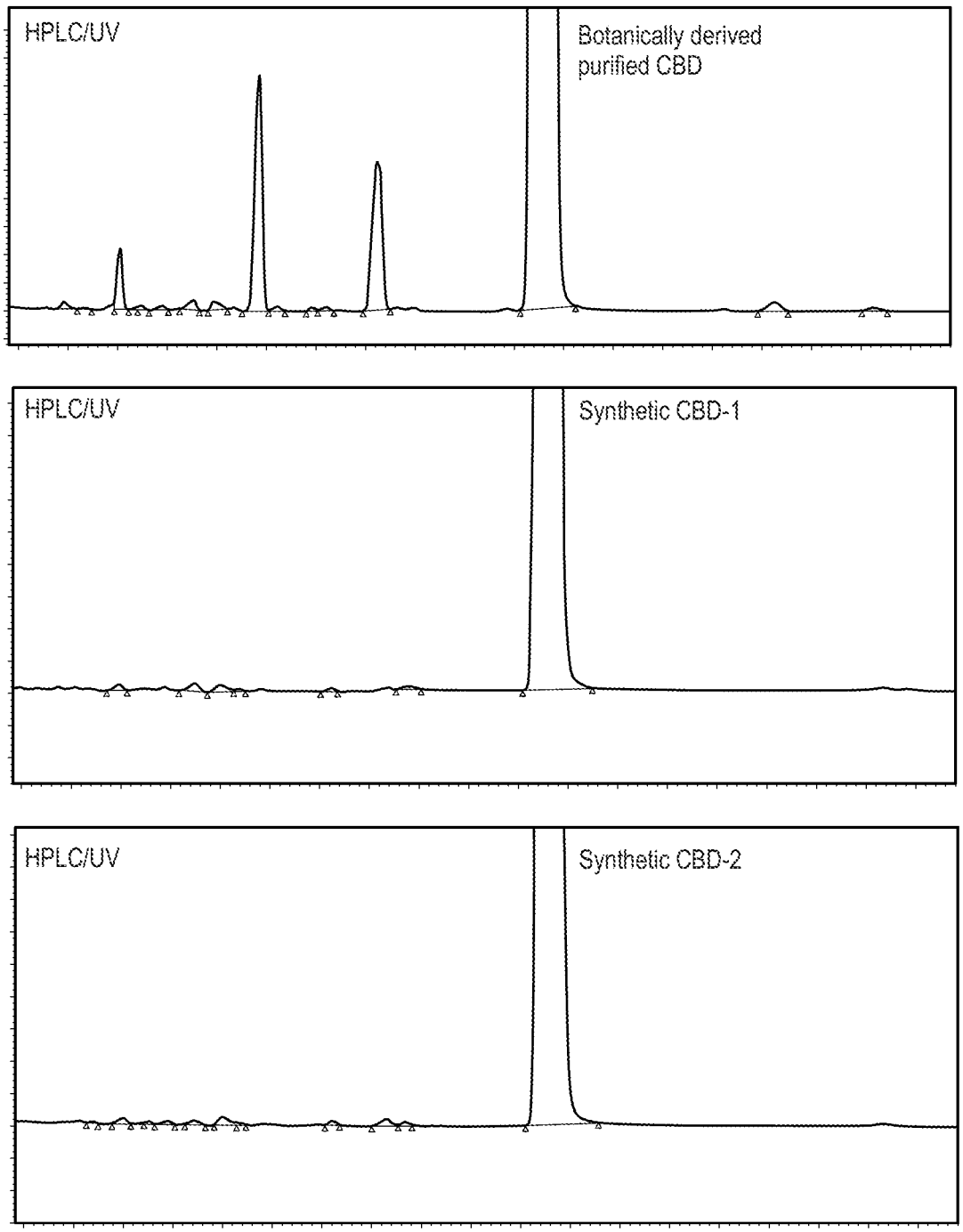
FIG. 8 depicts HPLC comparison of botanically derived purified CBD and synthetic CBD.

As can be seen in FIG. 8 there is a difference between the CBD of synthetic origin and that of botanically derived purified CBD. The botanically derived purified CBD sample has peaks which correspond to CBD-C1, CBDV, CBD-C4, trans-THC and cis-THC whereas the synthetically produced CBD does not comprise these compounds.

Example 7: Autofluorescence Properties of Botanically Derived Purified CBD and Synthetic CBD The physical properties of the emission and excitation spectrum of botanically derived purified CBD and synthetic CBD were determined in this example.

Methods

Test Substances

Botanically derived purified CBD (BOT) was tested in duplicates at six concentrations of 100 mM in 100% DMSO or 100% Ethanol, and at 100 µM, 50 µM, 1 µM, 0.5 µM, and 0.01 µM in PBS+0.1% Ethanol or PBS+0.1% DMSO containing vehicle solution. The THC concentration in the botanically derived purified CBD used was 0.03% (w/w) THC.

Synthetic CBD (SYN) was tested in duplicates at five concentrations of 100 mM, 50 mM, 1 mM, 0.5 mM, and 0.1 mM, in 100% Ethanol or 100% DMSO.

Microplate Preparation

200 µL of each sample or buffer were added into microplates in duplicate. Measurement has been performed on the Ensight multimodal plate reader (Perkin Elmer).

Selection of Excitation Wavelength

An excitation scan was used to detect the excitation peak for each test substance. The excitation scan was set from 230 to 380 nm and below the emission wavelength of 400 nm. The excitation scan was also set from 230 to 420 nm and below the emission wavelength of 440 nm. In both cases, a step increment of 2 nm was used for these scans.

Based on these analyses, the peaks of excitation wavelengths for the two tentative emission wavelengths were determined and used to identify the optimal excitation wavelength/s.

Selection of Emission Wavelength

In order to confirm the emission peak of the test substance, an emission scan was performed using the excitation peaks identified after the excitation scan. The excitation scan was set to start for botanically derived purified CBD at 50 nm above the tentative excitation values and for synthetic CBD at 20 nm above the tentative excitation values using a step increment of 2 nm. Wavelengths up to 800 nm were scanned for emission.

The wavelength giving the maximum emission for the samples was defined as the optimal emission wavelength for the chosen excitation wavelength.

Data Presentation

Raw data were derived from the software WorkOut Plus (version 2.5, Perkin Elmer, Waltham, Mass., USA). All data extracted from the software were checked by two people for complete verification before data analysis.

These data were used to generate the data presented herein, representing in x the wavelength (nm) and in y the fluorescent intensity using WorkOut Plus software (version 2.5, Perkin Elmer).

Data were subsequently to plot these as XY graphs using GraphPad Prism (version 8.0.2, La Jolla, USA).

Results
Excitation Peak Points for Botanically Derived Purified CBD and Synthetic CBD in DMSO Specific autofluorescence spectra distinct from the DMSO profile for each compound could only be detected at the highest concentration of 100 mM.

Figure 9:
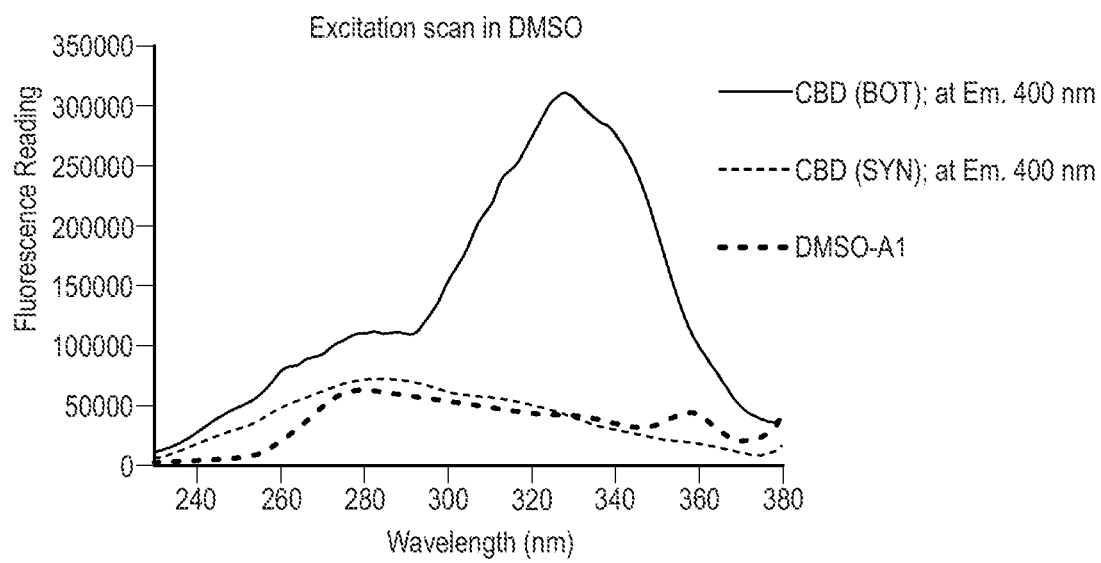
FIG. 9 depicts an autofluorescence spectra of botanically derived purified CBD and synthetic CBD at 100 mM representative of the excitation scan from 230 nm to below the emission wavelengths fixed at 400 or 440 nm.
Figure 9:
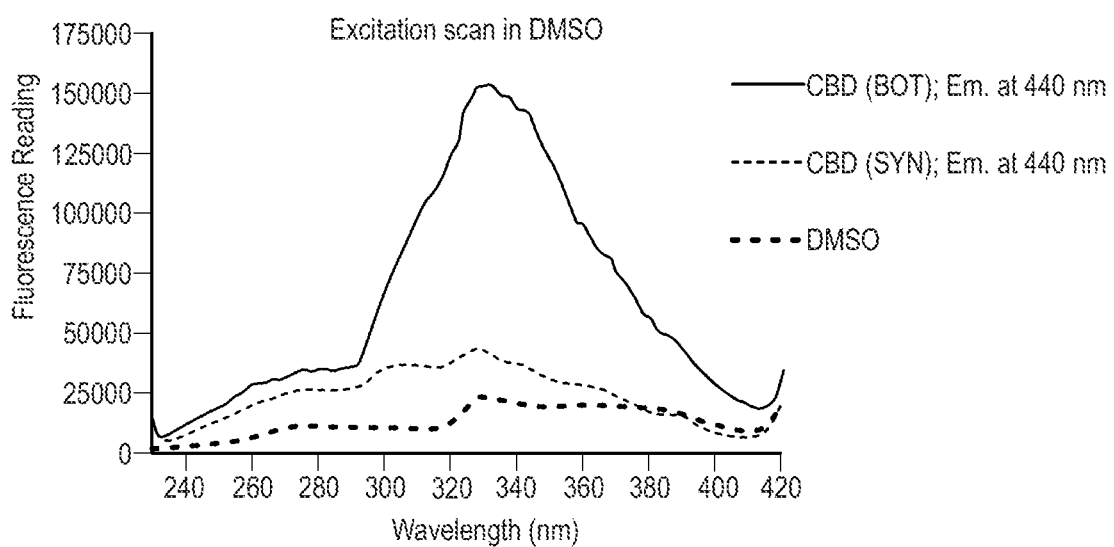

Representative spectroscopic data for each compound at the concentration of 100 mM are shown in FIG. 9.

Using pure DMSO as vehicle and with emission wavelength set at 400 or 440 nm, excitation peak points were identified for botanically derived purified CBD at 328 or 332 nm; with monodispersed peaks of higher fluorescence reading for botanically derived purified CBD compared to synthetic CBD.

Using pure DMSO as vehicle and with emission wavelength set at 400 or 440 nm, although excitation peak points were identified for synthetic CBD 282 or 328 nm; these overlap with peaks for DMSO suggestive of absence of excitation peak for this material in these conditions.

Emission Peak Points for Botanically Derived Purified CBD and Synthetic CBD in DMSO Specific autofluorescence for each compound could only be detected at the highest concentration of 100 mM. Data suggested low specific fluorescence detection similar to that of DMSO, at all lower concentrations.

Figure 10:
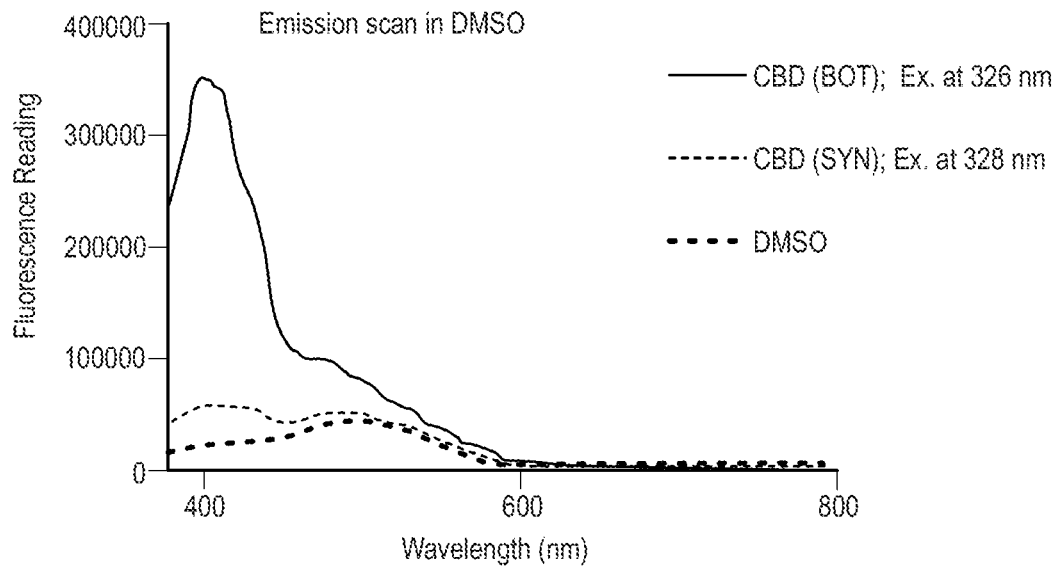
FIG. 10 depicts an autofluorescence spectra of botanically derived purified CBD and synthetic CBD at 100 mM representative of the emission scan up to 800 nm above the excitation wavelengths fixed at 326/370 nm for botanically derived purified CBD and 328/334/344 nm for synthetic CBD.
Figure 10:
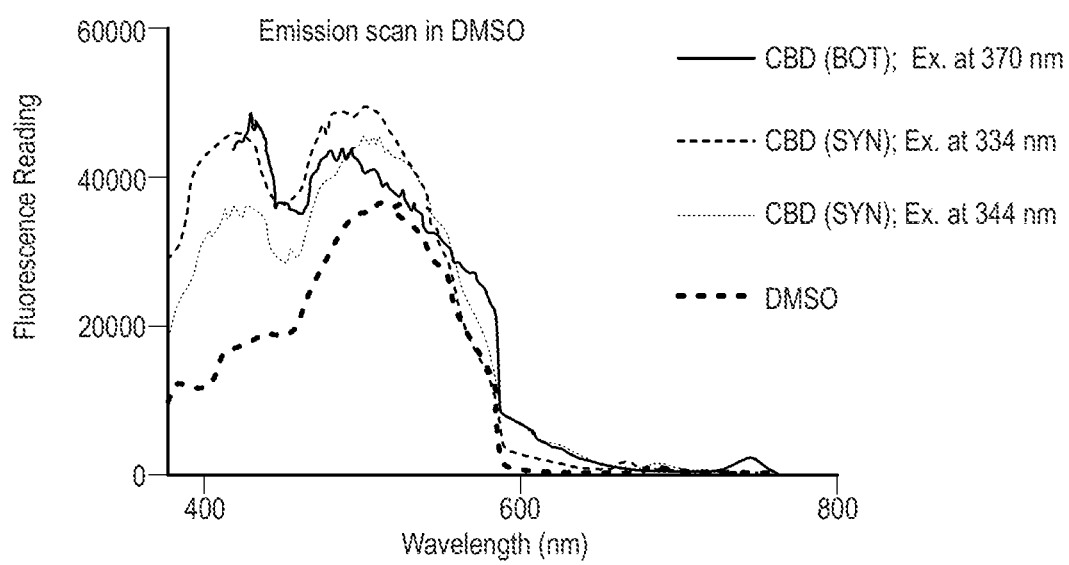

Representative spectroscopic data for each compound at the concentration of 100 mM are shown in FIG. 10.

Using pure DMSO as vehicle and with excitation wavelength set at 326 as identified from this study or 370 nm based on literature, emission peak points were identified for botanically derived purified CBD at 398 or 428 nm with a monodispersed peak of highest fluorescence reading at 326 nm.

Using pure DMSO as vehicle and with excitation wavelength set at 328/334/344/284 nm, excitation peak points were identified for synthetic CBD at 408/498/508/565 nm with a monodispersed peak of highest fluorescence reading at 565 nm. As this overlaps with DMSO peak it has not been included in the spectrogram.

Excitation Peak Points for Botanically Derived Purified CBD and Synthetic CBD in Ethanol Specific autofluorescence spectra distinct from the ethanol profile for each compound could only be detected at the highest concentration of 100 mM.

Figure 11:
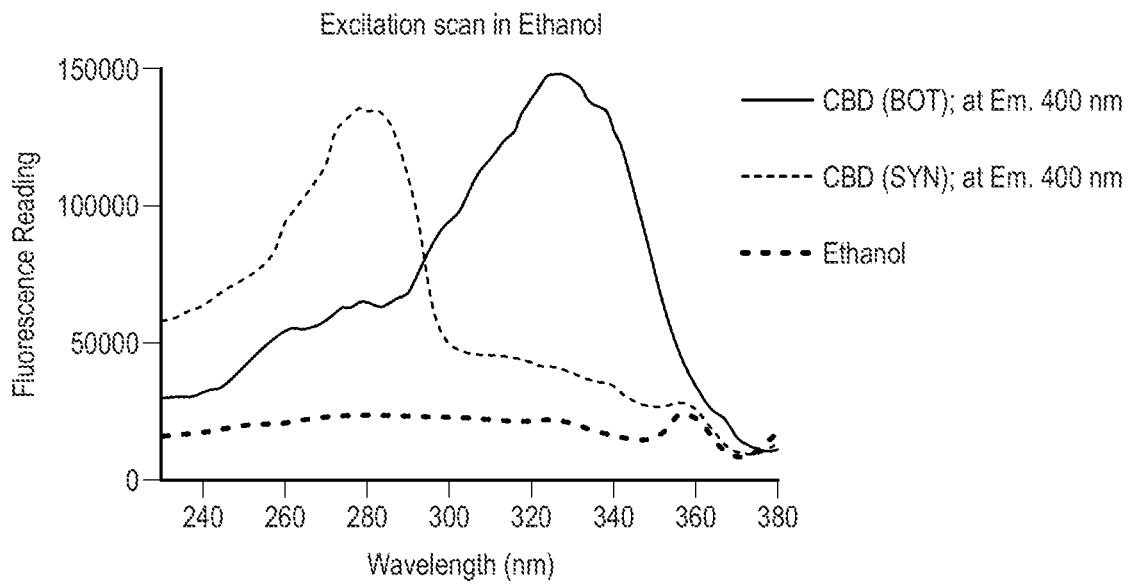
FIG. 11 depicts an autofluorescence spectra of botanically derived purified CBD and synthetic CBD at 100 mM representative of the excitation scan from 230 nm to below the emission wavelengths fixed at 400 or 440 nm.
Figure 11:
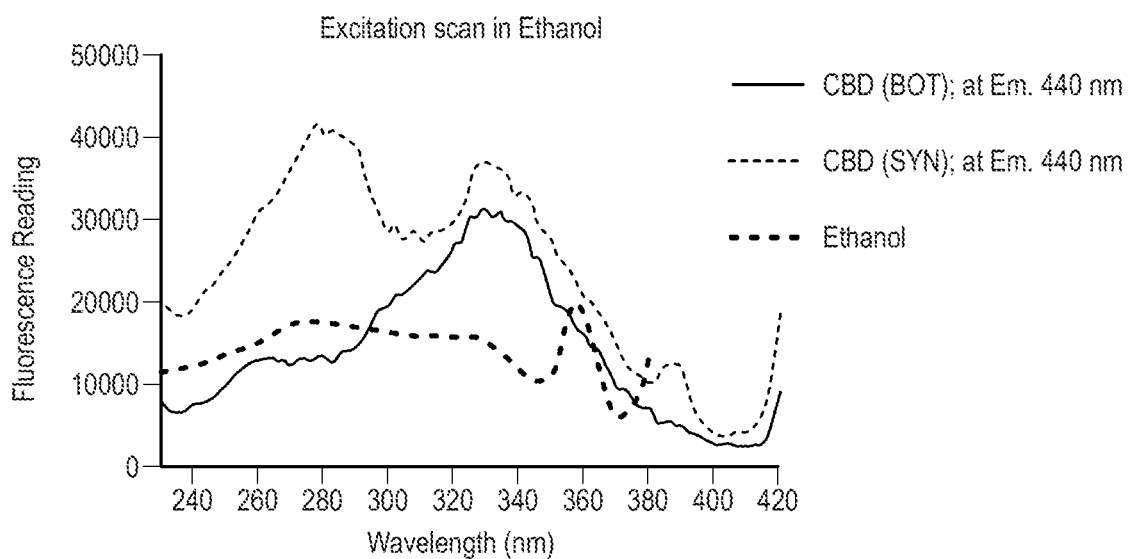

Representative spectroscopic data for each compound at the concentration of 100 mM are shown in FIG. 11.

Using pure ethanol as vehicle and with emission wavelength set at 400 nm, excitation peak points were identified for botanically derived purified CBD at 328 nm and synthetic CBD at 280 nm.

Using pure ethanol as vehicle and with emission wavelength set at 440 nm, excitation peak points were identified for botanically derived purified CBD at 330 nm and synthetic CBD at 328 nm.

Emission Peak Points for Botanically Derived Purified CBD and Synthetic CBD in Ethanol Specific autofluorescence for each compound could only be detected at the highest concentration of 100 mM. Data suggested low specific fluorescence detection similar to that of ethanol, at all lower concentrations.

Figure 12:
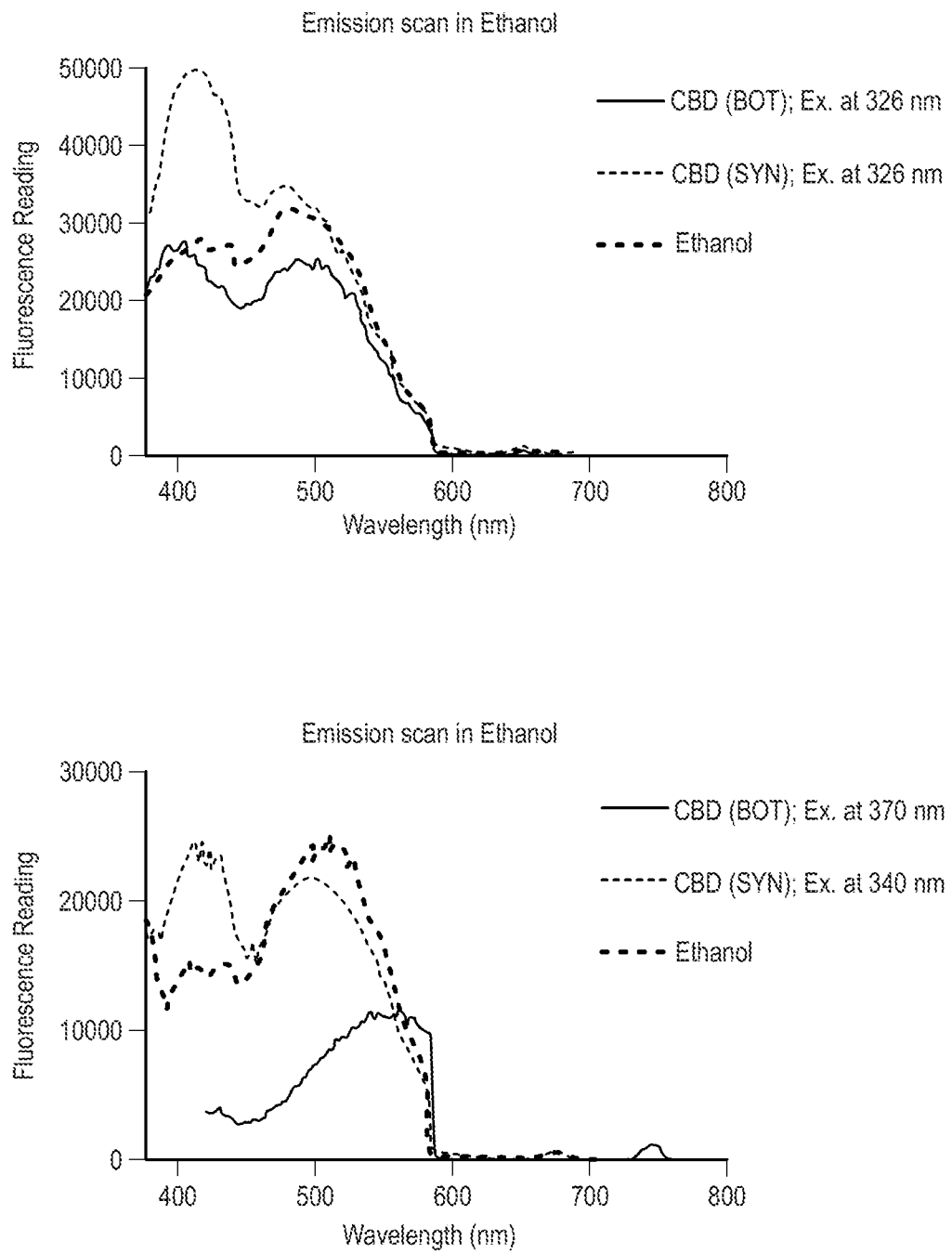
FIG. 12 depicts an autofluorescence spectra of botanically derived purified CBD and synthetic CBD at 100 mM representative of the emission scan up to 800 nm above the excitation wavelengths fixed at 326/370 nm for botanically derived purified CBD and 326/340 nm for synthetic CBD.

Representative spectroscopic data for each compound at the concentration of 100 mM are shown in FIG. 12.

Using pure ethanol as vehicle and with excitation wavelength set at 326 nm as identified in this study or 370 nm based on the literature, emission peak points were identified for botanically derived purified CBD at 404 nm or 560 nm.

Using pure ethanol as vehicle and with excitation wavelength set at 326 and 340 nm, excitation peak points were identified for synthetic CBD between 412 nm for both wavelengths.

Conclusion

The data presented in this example suggest there is difference in the excitation and emission wavelengths of botanically derived purified CBD and synthetic CBD. As such there is an apparent difference in the biophysical properties of the two compounds.

Conclusion of Data Demonstrating Physicochemical Properties of Botanically Derived Purified CBD The data presented in Examples 2 to 7 above describe the physicochemical properties of the botanically derived purified CBD preparation that was produced from a high-CBD plant.

This botanically derived purified CBD comprises greater than or equal to 98% (w/w) CBD and less than or equal to 2% (w/w) of other cannabinoids. The other cannabinoids present are THC at a concentration of less than or equal to 0.1% (w/w); CBD-C1 at a concentration of less than or equal to 0.15% (w/w); CBDV at a concentration of less than or equal to 0.8% (w/w); and CBD-C4 at a concentration of less than or equal to 0.4% (w/w).

These data additionally demonstrate that both trans-THC and cis-THC are present in the botanically derived purified CBD. Furthermore, it has been shown that the ratio of the trans-THC to cis-THC is altered and can be controlled by the processing and purification process, ranging from 3.3:1 (trans-THC:cis-THC) in its unrefined decarboxylated state to 0.8:1 (trans-THC:cis-THC) when highly purified.

Finally, these data demonstrate that the cis-THC found in botanically derived purified CBD is present as a mixture of both the (+)-cis-THC and the (−)-cis-THC isoforms.

Of note the comparison of the botanically derived purified CBD differs greatly in composition from that of a synthetic CBD. However as provided by the teachings of this invention a CBD preparation could be produced synthetically by producing a composition with duplicate components.

Data Demonstrating Therapeutic Efficacy of Botanically Derived Purified CBD

The following Examples describe data generated in vitro using cell lines and in vivo using animal studies in particular disease areas which demonstrate the superior efficacy of the botanically derived purified CBD preparation over that of synthetic CBD of the same concentration and purity.

The purity of the botanically derived purified CBD preparation used in these experiments was greater than or equal to 98%. The CBD preparation included less than or equal to 2% of other cannabinoids including THC, CBDV, CBD-C1, and CBD-C4. The THC was present at a concentration of less than or equal to 0.1% (w/w); CBD-C1 at a concentration of less than or equal to 0.15% (w/w); CBDV at a concentration of less than or equal to 0.8% (w/w); and CBD-C4 at a concentration of less than or equal to 0.4% (w/w).

The THC is present as both trans-THC and cis-THC in the botanically derived purified CBD preparation used in the following Examples. The ratio of the trans-THC to cis-THC was approximately 0.8:1 (trans-THC:cis-THC). The cis-THC was present as a mixture with both the (+)-cis-THC and the (−)-cis-THC isoforms being present.

Example 8: In Vitro Study on Neural Plasticity and Growth Cone Development

This example demonstrates that certain concentrations of botanically derived purified CBD are capable of inducing cell differentiation and neurite outgrowth.

Studies were conducted in order to identify the effects of botanically derived purified CBD and synthetic CBD on human iPSC derived cerebral cortical neural stem/progenitor cells in vitro (hNSCs).

Methods

Culture of Human iPSC-Derived Cerebral Cortical Neural Stem Cells (hNSCs)

Human iPSC-derived cerebral cortical neural stem cells (hNSCs) (Axol Bioscience Inc., UK) were cultured as monolayers at a density of $1.010^4$ cells/cm$^2$ on 100 mm diameter Petri dishes. The cells were collected from their original cryovial, suspended in Plating-XF Medium and plated on Petri dishes coated with SureBondXF 1× working solution prepared in D-PBS (without calcium or magnesium). hNSCs were incubated at 37° C. and 5% $CO_2$ and 24 hours after of incubation, the plating medium was replaced with fresh Neural Expansion-XF Medium supplemented with the growth factors Recombinant Human EGF and Recombinant Human FGF2 (final concentration of 20 ng/mL (1×) of FGF2 and EGF). The cultures were re-fed with fresh Neural Expansion-XF supplemented with EGF and FGF2 every two days. When the hNSCs reached approximately 80% confluence, they were prepared for treatment. Pre-warmed Axol Unlock-XF was used to detach the cells and after 3 minutes of incubation the cells were re-suspended in Neural Expansion-XF Medium supplemented with EGF and FGF2. The cells ($1\times10^4$ cells/cm$^2$) were then plated in Petri dishes coated with SureBondXF 1× and after 2 hours the medium was replaced with fresh Neural Expansion-XF supplemented with EGF and FGF2.

Cell Treatment with Test Cannabinoids hNSCs cultured as described above were plated at a density of $1\times10^4$ cells/cm$^2$ on SureBondXF-coated coverslips in the presence of botanically derived purified CBD; synthetic CBD; or vehicle diluted in the Neural Differentiation-XF Medium (DM, without growth factors) for 3-5 days at 37° C. in a 5% $CO_2$/95% air atmosphere.

Cannabinoids were dissolved in 95% (v/v) ethanol and added to the medium to obtain final concentrations of 0.1 or 1 µM CBD.

Ethanol was added to the vehicle-treated cells for the whole differentiation period of 3-5 days wherein the final concentration was never higher than 0.05% (v/v).

Immunohistochemistry

In order to perform immunohistochemistry, the cells were fixed with 4% (w/v) paraformaldehyde. Nonspecific binding was blocked with 10% (v/v) fetal bovine serum and 0.1% (v/v) Triton X-100 and incubated with primary antibodies: mouse anti-Map2ab (Sigma-Aldrich; 1:200) and rabbit anti-GFAP (DAKO; 1:200) or rabbit anti-Gap43 (Synaptic System; 1:300 at room temperature for 4 hours. Secondary antibodies—anti-mouse Alexa594 (Life Technologies; 1:100) and anti-rabbit Alexa488 (Life Technologies; 1:100)—were used for immunofluorescence. Cells were then counterstained with DAPI, washed with PBS and cover slipped with Aquatex mounting medium (Merck, Darmstadt, Germany). The immunofluorescence was studied with an epifluorescence microscope (Leica AF6000) equipped with the appropriate filter and then acquired using a digital camera (Leica, DFC 340) connected to the microscope and image analysis software (Leica, LAS AF). No immunoreactivity was found in the samples processed for the control of specificity of each primary antibody used in the study, which was performed by omitting the primary antibody before adding the appropriate secondary antibody.

Data Collection and Statistical Analysis

Digital Leica LAS AF 2.2.0 software (Live Data Mode system) was used for counting Map2ab+DAPI+ cells. The images were acquired with a Leica DMI6000 microscope equipped with appropriate blue (DAPI) and red (MAP2) filters for counting differentiated cells as violet (merge of DAPI, blue, and MAP2, red) and hNSCs as blue (DAPI only). For each experimental condition, cells from 3 different tubes were each analyzed in triplicate and 3 frames were collected at 20× magnification. Data were analyzed with GraphPad Prism 6 software, version 6.05 (GraphPad, Inc.) and are expressed as mean±SEM. Statistical differences among groups were determined by two-way ANOVA followed by post hoc Bonferroni tests for comparison among means. A level of confidence of $P<0.05$ was employed for statistical significance.

Results

Effect of Botanically Derived Purified CBD and Synthetic CBD on Neurogenesis and Neuronal Differentiation of hNSCs Two different botanically derived purified CBD preparations were tested on cultured human neural stem cells (hNSCs). Batch 1 comprised approximately 0.1% (w/w) THC and Batch 2 comprised 0.02% THC (w/w). Doses of 0.1 and 1 µM were used with both botanically derived purified CBD and synthetic CBD.

As shown in Table 8.1 below both batches of botanically derived purified CBD induced a significant increase in neurogenesis and neuronal differentiation of hNSCs, this is indicated by an increased number of MAP2-MAP2+ cells after incubation with CBD for 3 or 5 days.

TABLE 8.1

Percentage MAP2+ cells after 3 and 5 days incubation

| Sample | Mean % MAP2+ cells (3 days) | Mean % MAP2+ cells (5 days) |
|---|---|---|
| Vehicle | 4.59 ± 0.3 | 5.77 ± 0.23 |
| Botanically derived purified CBD (batch 1) 0.1 µM | 7.06 ± 0.11 *** | 20.38 ± 0.86 *** |
| Botanically derived purified CBD (batch 1) 1 µM | 28.29 ± 1.7 *** | 38.38 ± 1 *** |
| Botanically derived purified CBD (batch 2) 0.1 µM | 6.71 ± 0.91 *** | 18.83 ± 1.22 *** |
| Botanically derived purified CBD (batch 2) 1 µM | 20.04 ± 1.37 *** | 33.74 ± 1.83 *** |
| Synthetic CBD 0.1 µM | 4.87 ± 0.1 | 6.02 ± 0.3 |
| Synthetic CBD 1 µM | 6.11 ± 0.3 | 7.09 ± 0.1 |

*** $P < 0.0001$ vs vehicle-treated cells. Two-way analysis of variance (ANOVA) followed by the post-hoc Bonferroni test for pairwise comparison Botanically derived purified CBD at a concentration of 1 µM was found to be more potent than the 0.1 µM concentration for both batches and at both time points (3 days and 5 days of treatment). Interestingly, the same concentrations of synthetic CBD did not have a significant effect on neurogenesis or neuronal differentiation relative to vehicle-treated cells.

Effect of Botanically Derived Purified CBD and Synthetic CBD on Axonal Outgrowth and Neuronal Differentiation of hNSCs This study involved examining the effect of the two test compounds on neuronal differentiation of hNSCs after 3 or 5 days of treatment using GAP43 immunocytochemistry. As shown in Table 8.2 below, after 3 and 5 days of treatment with botanically derived purified CBD significantly increased neurogenesis by enhancing neurite elongation as confirmed by GAP43 expression in the vast majority of the cells.

TABLE 8.2

Percentage GAP43+ cells after 3 and 5 days incubation

| Sample | Mean % GAP43+ cells (3 days) | Mean % GAP43+ cells (5 days) |
| --- | --- | --- |
| Untreated | 5.96 ± 1.05 | 7.08 ± 1.5 |
| Botanically derived purified CBD 1 μM | 26.39 ± 3.40 | 37.32 ± 0.9 |
| Synthetic CBD 1 μM | 8.40 ± 2.0 | 9.15 ± 1.6 |

Conclusion

Together, these studies indicate that botanically derived purified CBD, which comprises less than or equal to 2% other cannabinoids including THC, CBD-C1, CBDV and CBD-C4 are capable of inducing differentiation and neurite outgrowth.

Remarkably the synthetic CBD (which does not contain these other cannabinoids) appears to not have any effect on neurogenesis and differentiation of hNSCs when supplied at the same concentration as the botanically derived purified CBD.

The effect shown by botanically derived purified CBD on neurogenesis and neurite outgrowth could be important for the treatment of neurodegenerative disease or brain injuries.

Example 9: Comparison of Botanically Derived Purified CBD and Synthetic CBD in a Mouse Model of Epilepsy This example demonstrates the effect of botanically derived purified CBD and synthetic CBD on mice in a maximal electroshock seizure test.

Methods

Animals and Experimental Conditions

This study was performed using male C57Bl6 mice, weighing between 23.6-31.2 g, which were purchased from a licensed breeder (Charles River, UK). Naïve mice were acclimatized to the procedure room in their home cages, with food and water available ad libitum. Animals were housed in groups of 2-3, in standard caging on a 12 hr/12 hr light-dark cycle. All animals were tail marked and weighed at the beginning of the study. Animals were randomly assigned to vehicle or treatment groups.

Anti-Epileptic Drugs (AED)

The following drugs were used in this study: synthetic CBD (SYN) and botanically derived purified CBD (BOT). The control vehicle used was (1:1:18), which was 5% Ethanol, 5% Kolliphor, 90% saline, and has been used extensively throughout similar seizure tests. All drugs were dissolved in the control vehicle for comparison. Animals were dosed (10 ml/kg) i.p. at 60 minutes prior to the administration of the maximal electroshock seizure (IVIES) test. In addition to the vehicle group, the dosage groups used for each treatment and included doses of 10, 50, 100 (Experiment 1 only), 150 and 200 mg/kg for CBD (SYN) and CBD (BOT). The number of animals in each of these groups were 10 (n=10).

Two separate experiments were undertaken using two different batches of the botanically derived purified CBD. In the first experiment the concentration of THC in botanically derived purified CBD was 0.02% THC (w/w) whereas in the second experiment the concentration of THC in the botanically derived purified CBD was approximately 0.1% THC (w/w).

Maximal Electroshock Seizure (MES) Test

The protective activity of CBD (SYN) and CBD (BOT) was evaluated and expressed as effective doses ($ED_{50}$ in mg/kg), protecting 50% of mice against IVIES-induced tonic seizures. Electroconvulsions were produced by a fixed current intensity of 30 mA and corneally delivered electroshock (0.2 second duration). Mice were individually assessed for seizures following this pre-determined high level (30 mA) corneally delivered electroshock of sufficient intensity to reliably produce tonic hind limb extension seizures in 100% of control animals. Induction of seizure was measured as an all-or-nothing effect scored as either present (+) or absent (0) for each animal. Data were collected by an observer unaware of the treatment for each animal and expressed as the total number of +s and 0s for each treatment group. Percent inhibition of relevant vehicle treated group (the degree of protection relative to vehicle treated controls) was then generated.

Statistical Analysis

All statistical tests were performed using commercially available GraphPad Prism version 7.0 for Windows (GraphPad Software, San Diego, Calif.). The effective doses ($ED_{50}$ in mg/kg), protecting 50% of mice against MES-induced tonic seizures for CBD (SYN) and CBD (BOT) were calculated in Prism using Sigmoidal dose-response—variable slope and log-probit analysis. The $ED_{50}$ values from CBD (SYN and CBD) were compared using the t test approach to compare two best best-fit values from one experiment to statistically evaluate the significance of differences between these.

Results

Figure 13:
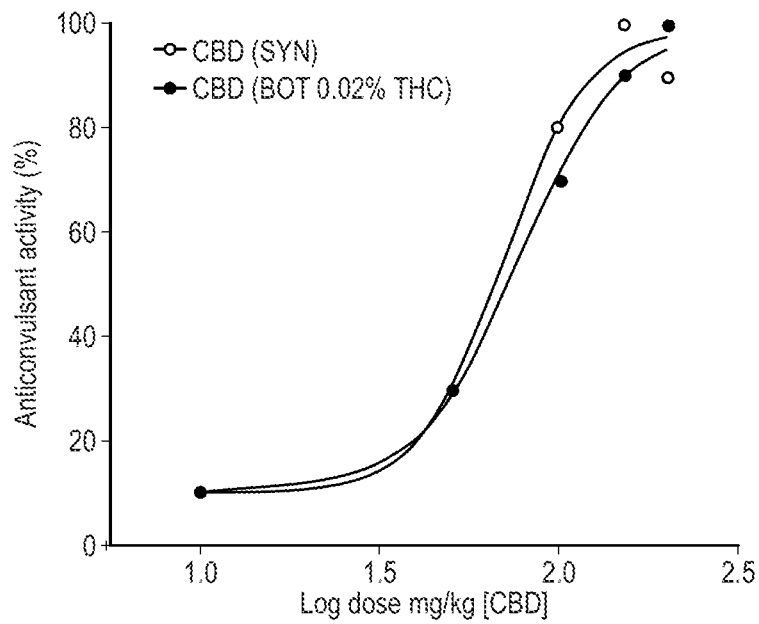
FIG. 13 depicts Experiment 1—sigmoidal curve showing log dose of CBD versus anticonvulsant activity upon IVIES test.

The anticonvulsant effects shown by given doses of CBD (SYN) and CBD (BOT 0.02% THC) were analyzed by sigmoidal curve analyses as shown in FIG. 13. The $ED_{50}$ values were derived from these sigmoidal curves as CBD (SYN): 77.63 mg/kg and CBD (BOT 0.02% THC): 70.22 mg/kg.

These $ED_{50}$ values were statistically compared using the t test approach for two best best-fit values from one experiment. As a result, these $ED_{50}$ values were determined statistically different as shown in Table 9.1 below (p=0.0013).

The mouse doses were converted to human equivalent dose (HED) of 10 mg/kg, assuming 60 kg human, and the difference in HED using CBD (BOT 0.02% THC) over CBD (SYN) is 10.00%.

TABLE 9.1

Experiment 1—Analysis from the t-test approach to compare the $ED_{50}$ of CBD (SYN) versus CBD (BOT 0.02% THC) and subsequent dose conversion to human equivalent dose (HED)

| Analysis | CBD (SYN) $ED_{50}$ (mg/kg) | CBD (BOT) $ED_{50}$ (mg/kg) | t-test (p value) | CBD (SYN) HED - mg | CBD (BOT) HED - mg | Diff. in HED (%) |
|---|---|---|---|---|---|---|
| Sigmoidal curve-constant top | 77.60 | 70.20 | 0.0013 | 600.0 | 542.8 | 10.0 |

Figure 14:
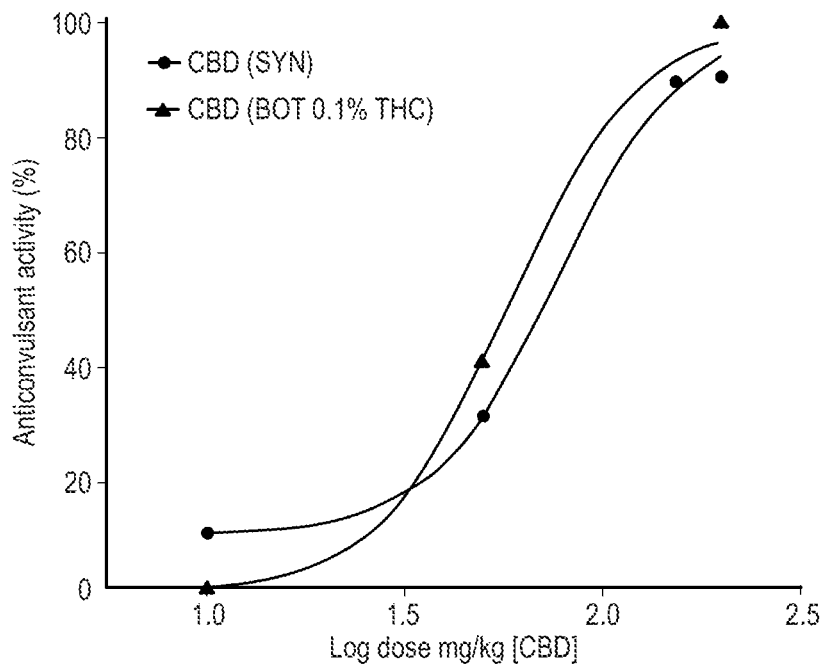
FIG. 14 depicts Experiment 2—sigmoidal curve showing log dose of CBD versus anticonvulsant activity upon IVIES test.

The anticonvulsant effects shown by given doses of CBD (SYN) and CBD (BOT 0.02% THC) were analyzed by sigmoidal curve analyses as shown in FIG. 14. The $ED_{50}$ values were derived from these sigmoidal curves as CBD (SYN): 77.40 mg/kg and CBD (BOT 0.1% THC): 57.94 mg/kg.

These $ED_{50}$ values were statistically compared using the t test approach for two best best-fit values from one experiment. As a result, these $ED_{50}$ values were determined statistically different as described in Table 9.2 (p=0.0000015).

The mouse doses have been converted to human equivalent dose (HED) of 10 mg/kg, assuming 60 kg human, and the difference in HED using CBD (BOT 0.08% THC) over CBD (SYN) is 28.75%.

TABLE 9.2

Experiment 2—Analysis from the t-test approach to compare the $ED_{50}$ of CBD (SYN) versus CBD (BOT approx. 0.1% THC) and subsequent dose conversion to human equivalent dose (HED)

| Analysis | CBD (SYN) $ED_{50}$ (mg/kg) | CBD (BOT) $ED_{50}$ (mg/kg) | t-test (p value) | CBD (SYN) HED - mg | CBD (BOT) HED - mg | Diff. in HED (%) |
|---|---|---|---|---|---|---|
| Sigmoidal curve-constant top | 77.40 | 57.94 | 0.0000015 | 600.0 | 449.15 | 28.75 |

Conclusion

The data generated in this study indicates that treatment with botanically derived purified CBD is more efficacious than treatment with synthetic CBD in the maximal electroshock model of epilepsy.

Such data are significant as they demonstrate that such a CBD composition may be useful in the treatment of epilepsy.

Example 10: Comparison of Botanically Derived Purified CBD and Synthetic CBD in an Animal Model of Schizophrenia The effect of PCP in the novel object recognition (NOR) test is a model of visual recognition memory deficits similar to those observed in schizophrenia. The atypical antipsychotics, clozapine and risperidone, can attenuate the deficit. The study was designed to determine if botanically derived purified CBD and/or synthetic CBD could attenuate the deficits in novel object recognition caused by administration of PCP.

Methods

Female hooded-Lister rats were used for this experiment. Rats were housed in groups of 5 under standard laboratory conditions under a 12 hr light: dark cycle, with lights on at 0700 hr. Testing was carried out in the light phase. Rats were randomly assigned to two treatment groups and treated with vehicle, n=20 (distilled water, i.p.) or Phencyclidine hydrochloride (PCP), n=100 (2 mg/kg, i.p. twice daily for 7-days). PCP was dissolved in distilled water. This was followed by a 7-day wash out period before the rats were tested following acute treatment with CBD, risperidone or vehicle.

Risperidone (0.1 mg/kg) was dissolved in a minimum volume of acetic acid, made up to volume with distilled water and pH adjusted to 6 with 0.1M NaOH and administered via the i.p. route in a volume of 1 ml/kg, 120 minutes prior to testing.

Botanically derived purified CBD was tested at 2, 10, 20 or 100 mg/kg and was dissolved in 2:1:17 (Ethanol:Cremofor:Saline 0.9%) and administered via the i.p. route in a volume of 5 ml/kg, 60 minutes prior to testing. The THC concentration in the botanically derived purified CBD was 0.03% (w/w) THC.

Synthetic CBD at 1, 2, 5, 10 or 20 mg/kg was dissolved in 2:1:17 (Ethanol:Cremofor:Saline 0.9%) and administered via the i.p. route in a volume of 5 ml/kg, 120 minutes prior to testing.

Rats were allowed to habituate to the empty test box and the behavioral test room environment for one hour on day 1. Prior to behavioral testing on day 2, rats were given a further 3 minute habituation.

Following the 3 minute habituation period, the rats are given two 3 minute trials (T1 and T2) which were separated by a 1 minute inter-trial interval in the home cage during which the objects were changed. Behavior in all trials was recorded on video for subsequent blind scoring.

In the acquisition trial (T1), the animals were allowed to explore two identical objects (A1 and A2) for 3 minutes. In the retention trial (T2), the animals were allowed to explore a familiar object (A) from T1 and a novel object (B) for 3 minutes. The familiar object presented during T2 was a duplicate of objects presented in T1 in order to avoid any olfactory trails.

Object exploration was defined by animals licking, sniffing, or touching an object with the forepaws while sniffing the object, but object exploration did not include an animal leaning against, turning around, standing on or sitting on an object. The exploration time(s) of each object (A, B, familiar and novel) in each trial were recorded using two stopwatches and the following factors were calculated: total exploration time of both objects in the acquisition trial, total exploration time of both objects in the retention trial. Habituation of exploratory activity included the exploration time, as measured by the number of lines crossed, for both trials.

All data were assessed for normality using D'Agostino and Pearson normality test. Data non-normally distributed were analyzed using Kruskal-Wallis followed by planned comparisons with Dunn's correction. Normally distributed data were analyzed using one-way ANOVA followed by planned comparisons with Sidak's correction. All analyses were carried out using GraphPad Prism V7.03.

Results

Figure 15:
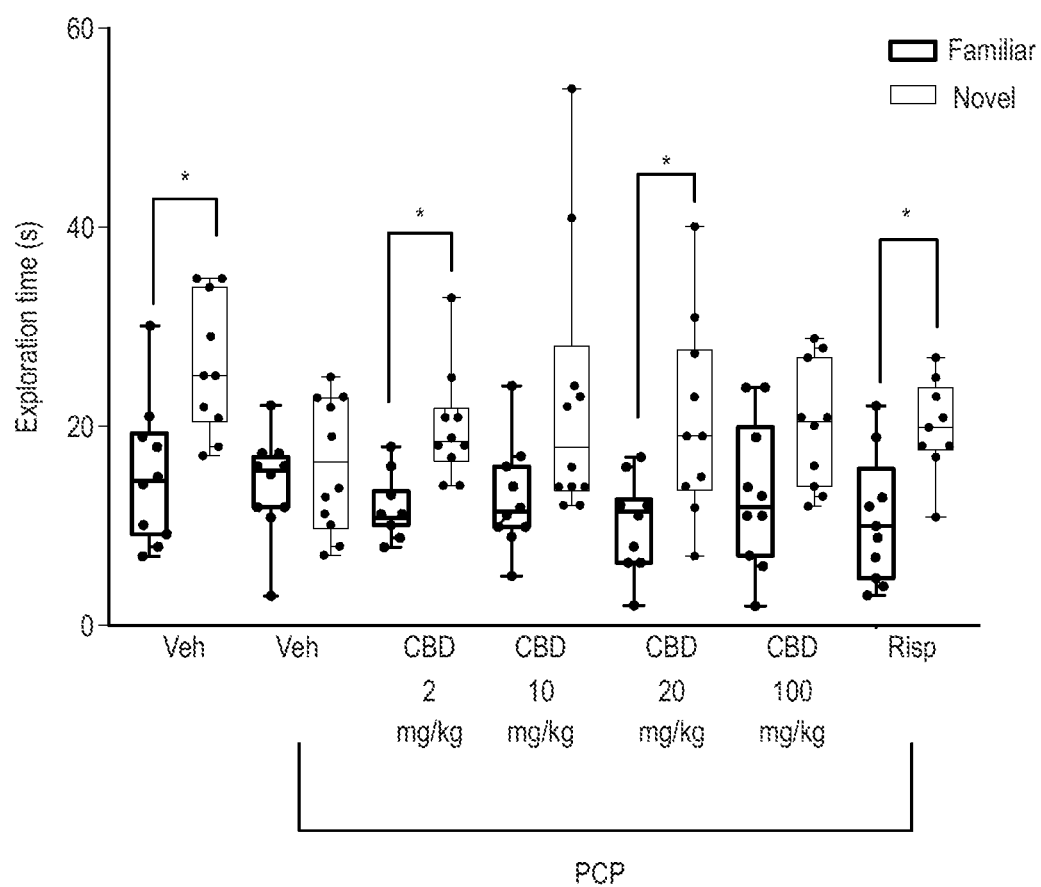
FIG. 15 depicts novel versus familiar exploration times in rats treated with botanically derived purified CBD.

As shown in FIG. 15, botanically derived purified CBD (2-100 mg/kg i.p., 120 min ppt) attenuated a sub-chronic PCP-induced deficit in novel object recognition in rats (n=9-10 per group), with a minimal effective dose (MED) of 2 mg/kg, (p=<0.05).

Figure 16:
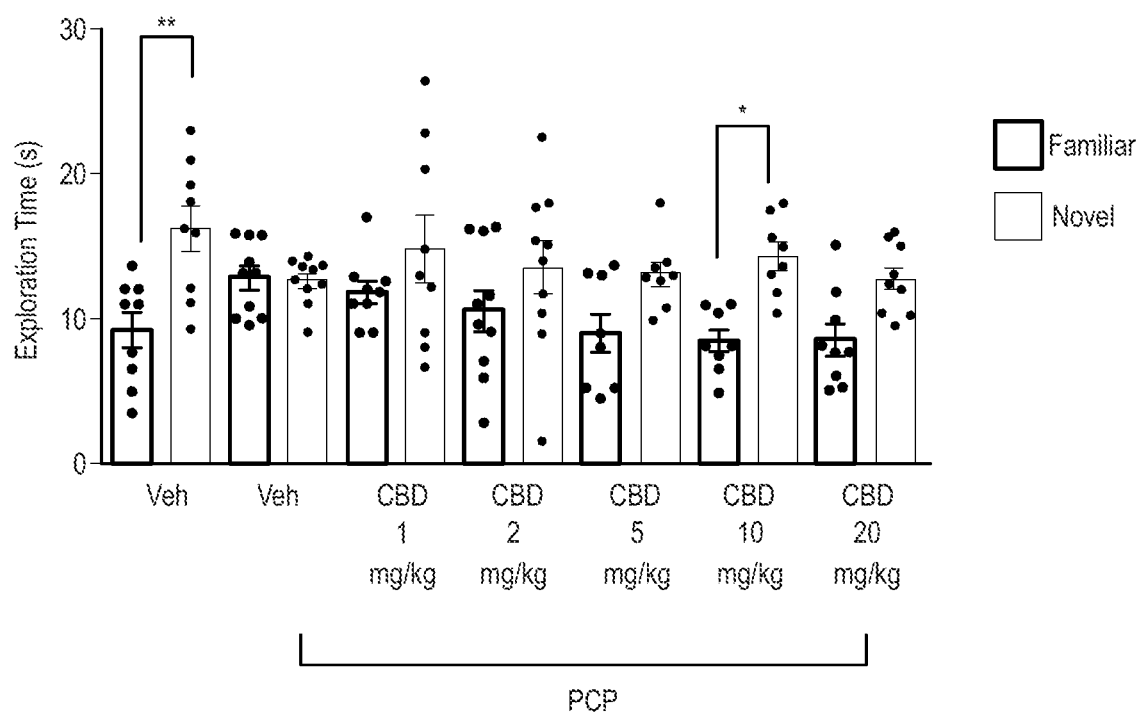
FIG. 16 depicts novel versus familiar exploration times in rats treated with synthetic CBD.

As shown in FIG. 16, synthetic CBD (2-100 mg/kg i.p., 120 min ppt) attenuated a sub-chronic PCP-induced deficit in novel object recognition in the rat (n=8-10 per group), with a minimal effective dose (MED) of 10 mg/kg (p=<0.01).

Interestingly, the difference in potency (minimal effective dose) between the synthetic CBD and botanically derived purified CBD means that in a 70 kg human being dosed at 20 mg/kg/day of CBD there is a significant difference in the amount of CBD required. As shown below:

Rat dose of 2 mg/kg/day=(2×0.16)=0.32 mg/kg/day in a human=(0.32×70)=22.4 mg/day for highly purified CBD of botanic origin.

Rat dose of 10 mg/kg/day=(10×0.16)=1.6 mg/kg/day in a human=(1.6×70)=112 mg/day for synthetic CBD Calculations are based on FDA dose conversion guidance from animal to human (to convert a mg/kg dose in a rat to a mg/kg human equivalent dose the rat dose is multiplied by 0.16).

Conclusion

Botanically derived purified CBD has been shown to be useful in attenuating the sub-chronic PCP-induced deficit in novel object recognition in rats at a much lower minimal effective dose (MED) than synthetic CBD suggesting it would be a useful treatment option in schizophrenia and associated conditions.

Given the difference in potency, using synthetic CBD in a human would require five times the amount of CBD than botanically derived purified CBD. Such a difference in potency is important given that CBD is an expensive compound to produce whether from a synthetic or botanic route.

Example 11: Comparison of High Concentrations of THC in Combination with Botanically Derived Purified CBD in an Animal Model of Schizophrenia The novel object recognition (NOR) test as described in Example 9 above is a model of visual recognition memory deficits similar to those observed in schizophrenia. The study was designed to determine if higher concentrations of THC, as are commonly found in vernacular CBD oil preparations would affect the ability of botanically derived purified CBD to attenuate the deficits in novel object recognition caused by administration of PCP in rats.

Vernacular CBD preparations typically comprise between 3 and 20% (w/w) THC.

Methods

The same method that is described in Example 10 above was employed in this experiment.

Botanically derived purified CBD was tested at 20 mg/kg with an addition of either 10% (w/w) or 20% (w/w) THC added to the CBD. Botanically derived purified CBD which comprised 0.08% THC was made up to 10% THC and 20% THC with purified botanically derived THC.

The cannabinoids were dissolved in 2:1:17 (Ethanol:Cremofor:Saline 0.9%) and administered via the i.p. route in a volume of 5 ml/kg, 120 minutes prior to testing.

The behavioral test was performed as described in Example 10 above.

All data were assessed for normality using D'Agostino and Pearson normality test. Data non-normally distributed were analyzed using Kruskal-Wallis followed by planned comparisons with Dunn's correction. Normally distributed data were analyzed using one-way ANOVA followed by planned comparisons with Sidak's correction. All analyses were carried out using GraphPad Prism V7.03.

Results

The animals treated with the botanically derived purified CBD comprising 20% (w/w) THC were found to be sedated and as such no data was generated with respect to the novel object recognition for this group.

Some of the animals treated with the botanically derived purified CBD comprising 10% (w/w) THC were also found to be sedated and as such data was only generated with five of the 15 test animals for this group.

Figure 17:
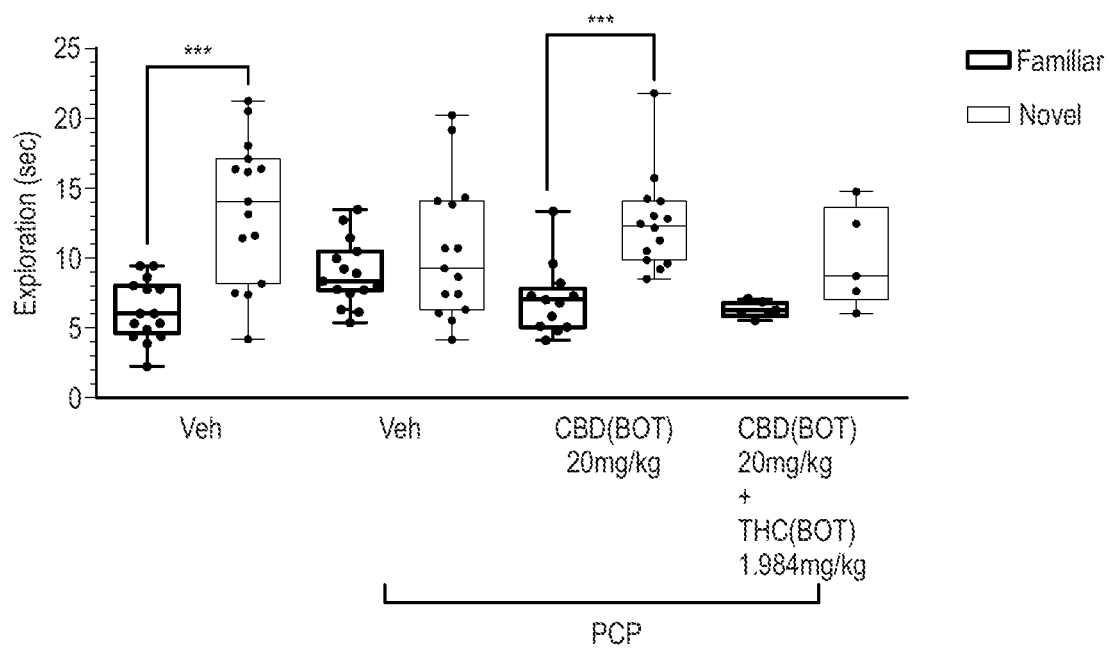
FIG. 17 depicts novel versus familiar exploration times in rats treated with botanically derived purified CBD supplemented with THC at 10 and 20% (w/w).
Figure 18:
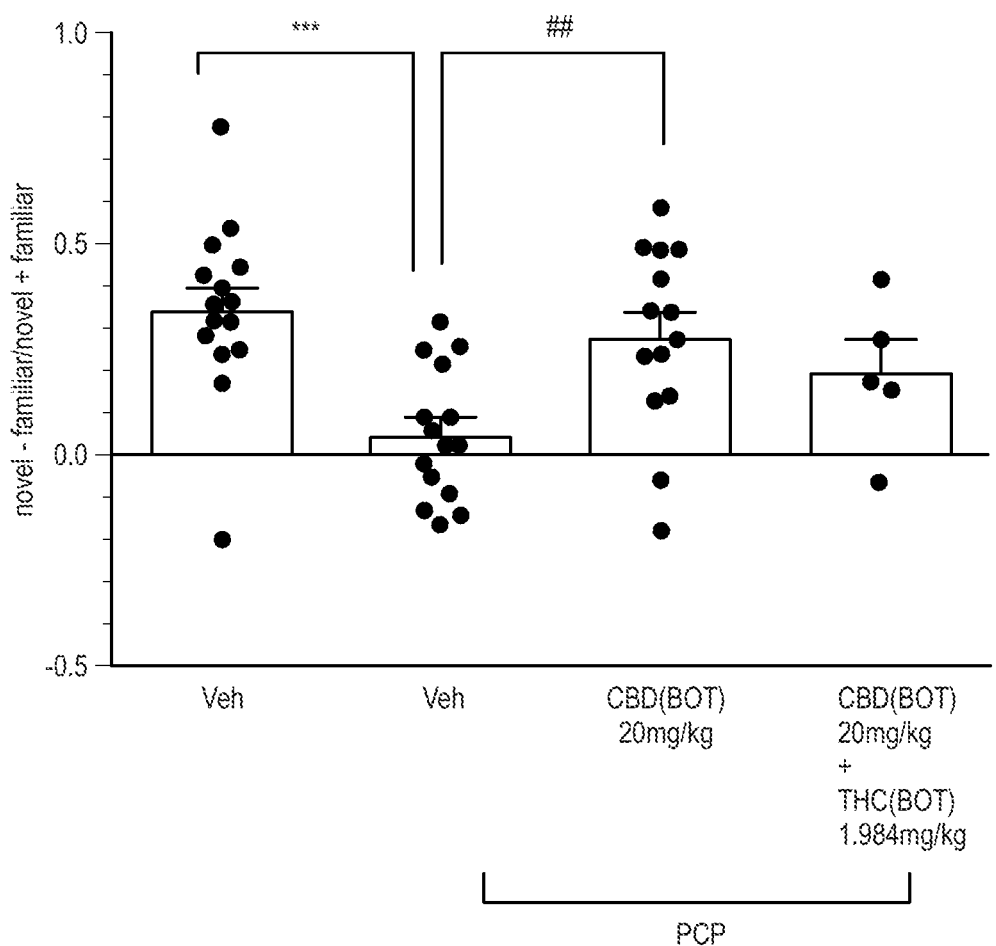
FIG. 18 depicts discrimination index in rats treated with botanically derived purified CBD supplemented with THC at 10 and 20% (w/w).
Figure 19:
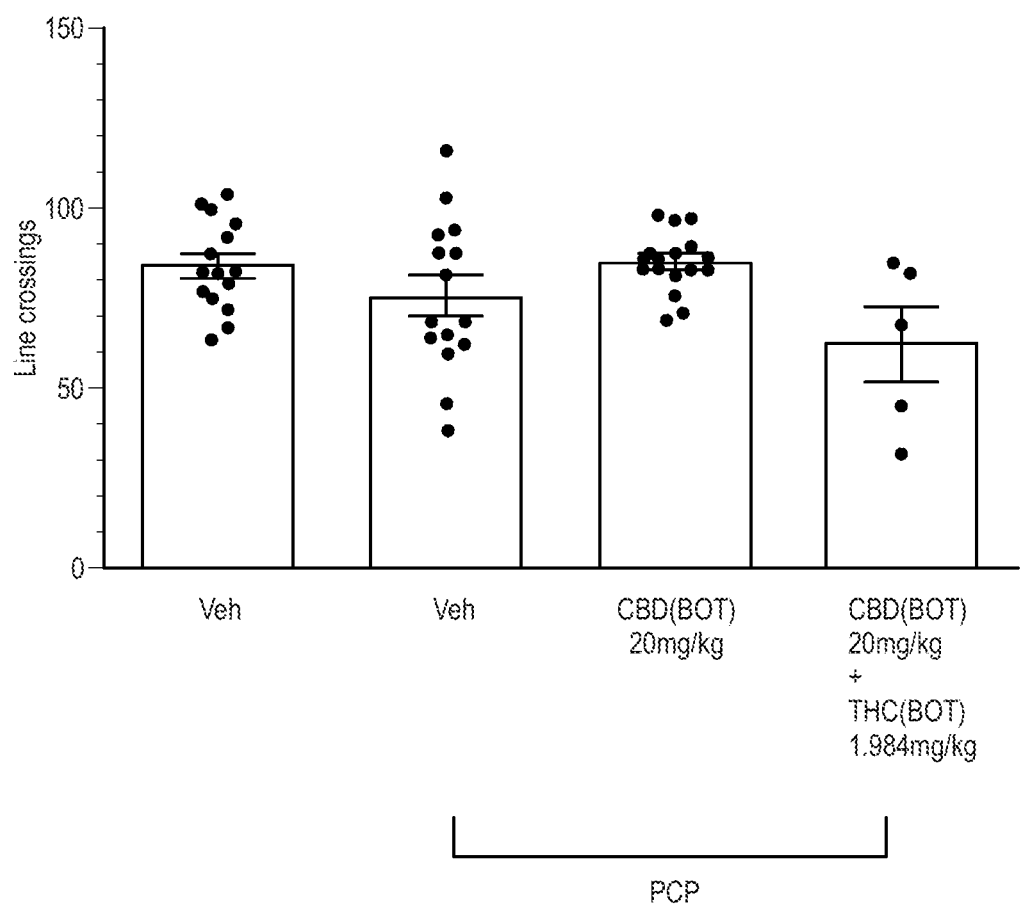
FIG. 19 depicts number of line crossings in rats treated with botanically derived purified CBD supplemented with THC at 10 and 20% (w/w).

As can be seen in FIGS. 17 to 19 animals treated with botanically derived purified CBD at 20 mg/kg were able to attenuate the sub-chronic PCP-induced deficit in novel object recognition. Interestingly, it was observed that this effect was removed in animals that were treated with botanically derived purified CBD comprising 10% (w/w) THC.

FIG. 17 demonstrates that botanically derived purified CBD (20 mg/kg i.p., 120 min ppt) attenuated a sub-chronic PCP-induced deficit in novel object recognition in rats (n=15 per group), (p=<0.001). Whereas in the group administered CBD (20 mg/kg) plus THC (1.984 mg/kg, i.p., 120 min ppt) this effect was lost (n=5). Effects similar to those observed in the vehicle treated PCP rats occurred.

FIG. 18 details the discrimination index (DI) in rats treated with botanically derived purified CBD supplemented with THC at 10 and 20% (w/w). Rats treated with botanically derived purified CBD (20 mg/kg i.p., 120 min ppt) had a DI which was similar to those rats untreated with PCP (n=15 per group), (p=<0.01). Whereas in the group administered CBD (20 mg/kg) plus THC (1.984 mg/kg, i.p., 120 min ppt) this effect was lost (n=5).

FIG. 19 details the number of line crossings in rats treated with botanically derived purified CBD supplemented with THC at 10 and 20% (w/w). Rats treated with CBD (20 mg/kg) plus THC (1.984 mg/kg, i.p., 120 min ppt) had a reduced number of line crossings (n=5).

Conclusion

As such it would appear that a small concentration of THC as is found in the botanically derived purified CBD is efficacious however increasing the concentration of THC to levels found in vernacular CBD preparations is detrimental to cognitive and social deficit.

Conclusion of Data Demonstrating Therapeutic Efficacy of Botanically Derived Purified CBD The data presented in Examples 8 to 11 above describe the pharmacological properties of the botanically derived purified CBD preparation that was produced from a high-CBD plant in comparison to synthetic CBD.

As we have determined in Examples 2 to 7 the botanically derived purified CBD used in these experiments has a precise composition which differs from that of synthetic CBD albeit the two compositions have the same concentration of CBD.

These data demonstrate in three different models that the botanically derived purified CBD is more efficacious than synthetic CBD. These data are surprising given that the difference in the composition between the two types of CBD tested lies only within what may be considered to be the impurities.

Such data are important in many respects. Firstly, when treating a patient with a disease or condition the medical practitioner is desirous of ensuring the most effective treatment possible. These data show that the botanically derived purified CBD is more effective than synthetic CBD and as such is a more valuable treatment option, particularly in patients that are suffering from difficult to treat conditions such as many of the epilepsy syndromes such as Dravet syndrome or Lennox-Gastaust syndrome.

Secondly, the findings from these experiments have demonstrated that botanically derived purified CBD is effective at a lower minimal effective dose than synthetic CBD. As such when administering the botanically derived purified CBD a smaller amount of the composition may be provided. This has many benefits including a lower cost of goods, potentially lower associated side effects and patient compliance.

Furthermore, these data also demonstrate that using an unrefined source of CBD such as that which is found from CBD oil retailers does not produce the same efficacious benefits as is observed with botanically derived purified CBD. The detrimental effects shown on cognition when the amount of THC in the CBD was increased to vernacular levels suggests that such compositions would not be suitable for the treatment of many diseases and conditions.

In summary, the precise composition of components within the botanically derived purified CBD are of great benefit. Such a composition may be reproduced using either CBD of botanical origin or components that are produced synthetically.

The invention claimed is:

1. A cannabidiol (CBD) preparation comprising greater than or equal to 90% (w/w) CBD based on total amount of cannabinoid in the preparation and the remainder comprises other cannabinoids, wherein the other cannabinoids comprise tetrahydrocannabinol (THC), wherein the THC is present as a mixture of trans-THC and cis-THC, and wherein the ratio of trans-THC to cis-THC is about 0.7:1.0 to about 5.0:1.0.

2. The CBD preparation of claim 1, comprising not more than 1.5% (w/w) THC based on total amount of cannabinoid in the preparation.

3. The CBD preparation of claim 1, comprising about 0.01% to about 0.1% (w/w) THC based on total amount of cannabinoid in the preparation.

4. The CBD preparation of claim 1, comprising about 0.02% to about 0.05% (w/w) THC based on total amount of cannabinoid in the preparation.

5. The CBD preparation of claim 1, wherein the ratio of trans-THC to cis-THC is about 0.7:1.0 to about 3.6:1.0.

6. The CBD preparation of claim 1, comprising about 0.1% to about 0.15% (w/w) CBD-C1 based on total amount of cannabinoid in the preparation.

7. The CBD preparation of claim 1, comprising about 0.2% to about 0.8% (w/w) CBDV based on total amount of cannabinoid in the preparation.

8. The CBD preparation of claim 1, comprising about 0.3% to about 0.4% (w/w) CBD-C4 based on total amount of cannabinoid in the preparation.

9. The CBD preparation of claim 1, wherein at least a portion of at least one of the cannabinoids present in the CBD preparation is isolated from cannabis plant material.

10. The CBD preparation as claimed in claim 1, wherein at least a portion of the CBD present in the CBD preparation is isolated from cannabis plant material.

11. The CBD preparation as claimed in claim 1, wherein at least a portion of the THC present in the CBD preparation is isolated from cannabis plant material.

12. The CBD preparation of claim 1, wherein the cannabinoids present in the CBD preparation are isolated from cannabis plant material.

13. The CBD preparation of claim 12, wherein the cannabis plant material is from a *Cannabis sativa, Cannabis indica*, or *Cannabis ruderalis* plant.

14. The CBD preparation of claim 13, wherein the cannabis plant is a high-CBD containing cannabis chemotype.

15. The CBD preparation of claim 1, wherein at least a portion of at least one of the cannabinoids present in the CBD preparation is prepared synthetically.

16. The CBD preparation of claim 1, wherein substantially all of at least one of the cannabinoids present in the CBD preparation is prepared synthetically.

17. The CBD preparation of claim 1, wherein the cannabinoids present in the CBD preparation are prepared synthetically.

18. A pharmaceutical composition comprising the CBD preparation of claim 1 and at least one pharmaceutically acceptable excipient.

19. The pharmaceutical composition of claim 18, wherein the pharmaceutical composition is a liquid dosage form.

20. The pharmaceutical composition of claim 18, wherein the ratio of trans-THC to cis-THC is about 0.7:1.0 to about 2.0:1.0.

21. A method of treating epilepsy in a subject in need thereof, comprising administering a therapeutically effective amount of the CBD preparation of claim 1, wherein the epilepsy is Dravet syndrome, Lennox Gastaut syndrome, Doose syndrome, or tuberous sclerosis complex (TSC).

22. The method of treating epilepsy of claim 21, wherein the therapeutically effective amount of the CBD preparation provides a dose of CBD ranging from about 5 mg/kg/day to about 50 mg/kg/day.

23. The method of treating epilepsy of claim 21, wherein the epilepsy is Dravet syndrome.

24. The method of claim 23, wherein the wherein the therapeutically effective amount of the CBD preparation provides a dose of CBD of 10 mg/kg/day or 20 mg/kg/day.

25. The method of treating epilepsy of claim 21, wherein the epilepsy is Lennox Gastaut syndrome.

26. The method of claim 25, wherein the wherein the therapeutically effective amount of the CBD preparation provides a dose of CBD of 10 mg/kg/day or 20 mg/kg/day.

27. The method of treating epilepsy of claim 21, wherein the epilepsy is Doose syndrome.

28. The method of treating epilepsy of claim 21, wherein the epilepsy is TSC.

29. The method of claim 28, wherein the wherein the therapeutically effective amount of the CBD preparation provides a dose of CBD of about 25 mg/kg/day.

30. The method of claim 27, wherein the wherein the therapeutically effective amount of the CBD preparation provides a dose of CBD of 10 mg/kg/day, 20 mg/kg/day, or 25 mg/kg/day.

* * * * *